US012653400B2

(12) United States Patent
Anwar et al.

(10) Patent No.: US 12,653,400 B2
(45) Date of Patent: Jun. 16, 2026

(54) IMPLANTABLE IMAGERS FOR IN VIVO IMAGING

(71) Applicant: The Regents of the University of California, Oakland, CA (US)

(72) Inventors: Mekhail Anwar, San Francisco, CA (US); Rozhan Rabbani, San Francisco, CA (US); Micah Roschelle, San Francisco, CA (US); Hossein Najafiaghdam, San Francisco, CA (US); Rikky Muller, Berkeley, CA (US); Mohammad Meraj Ghanbari, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 37 days.

(21) Appl. No.: 18/273,909

(22) PCT Filed: Jan. 28, 2022

(86) PCT No.: PCT/US2022/014394
§ 371 (c)(1),
(2) Date: Jul. 24, 2023

(87) PCT Pub. No.: WO2022/165234
PCT Pub. Date: Aug. 4, 2022

(65) Prior Publication Data
US 2025/0325186 A1 Oct. 23, 2025

Related U.S. Application Data

(60) Provisional application No. 63/253,444, filed on Oct. 7, 2021, provisional application No. 63/143,289, filed on Jan. 29, 2021.

(51) Int. Cl.
*A61B 5/00* (2006.01)

(52) U.S. Cl.
CPC .......... *A61B 5/0071* (2013.01); *A61B 5/0084* (2013.01); *A61B 5/686* (2013.01);
(Continued)

(58) Field of Classification Search
CPC ..... A61B 5/0071; A61B 5/0084; A61B 5/686; A61B 2560/0219; A61B 2560/0462; A61B 2562/046
See application file for complete search history.

(56) References Cited

U.S. PATENT DOCUMENTS

| | | | |
|---|---|---|---|
| 4,816,567 A | 3/1989 | Cabilly et al. | |
| 5,223,409 A | 6/1993 | Ladner et al. | |

(Continued)

FOREIGN PATENT DOCUMENTS

| | | |
|---|---|---|
| EP | 0404097 | 12/1990 |
| GB | 2276169 | 9/1994 |

(Continued)

OTHER PUBLICATIONS

Al-Rawhani, et al. (2013) "Design and Implementation of a Wireless Capsule Suitable for Autofluorescene Intensity Detection in Biological Tissues", IEEE Transactions on Biomedical Engineering, vol. 60, No. 1, Jan. 1, 2013, pp. 55-62.

(Continued)

*Primary Examiner* — Dixomara Vargas
(74) *Attorney, Agent, or Firm* — Edward J. Baba; Christian Hans; Bozicevic, Field & Francis LLP

(57) ABSTRACT

Devices, systems, and methods are provided for in vivo fluorescence imaging. Disclosed herein is an implantable miniature fluorescence imager on a chip having a custom imaging array with angle selective gratings, fiber optics, or microcollimators for image deblurring, and optical filters that can be tuned to image fluorescence from multiple fluorophores simultaneously. Power is supplied by an on- (Continued)

chip power source or transmitted to the chip from an external transducer such as an ultrasound transducer, electromagnetic transducer, inductive transducer, or radiofrequency transducer. Wireless communication may be provided by electromagnetic or ultrasound links to the device. The function of a fluorescence microscope is provided in a millimeter-scale device that can be readily implanted in tissue and used to image fluorescently labeled cells in vivo. The small size of the fluorescence imager makes possible sustained in vivo imaging with real-time monitoring of multiple cell types within Shifting the dynamic diseased tissue or a tumor.

36 Claims, 58 Drawing Sheets

(52) U.S. Cl.
CPC ................. *A61B 2560/0219* (2013.01); *A61B 2560/0462* (2013.01); *A61B 2562/046* (2013.01)

(56) References Cited

U.S. PATENT DOCUMENTS

| | | | |
|---|---|---|---|
| 5,438,119 | A | 8/1995 | Rutter et al. |
| 5,440,016 | A | 8/1995 | Blondelle et al. |
| 5,463,564 | A | 10/1995 | Agrafiotis et al. |
| 5,525,735 | A | 6/1996 | Gallop et al. |
| 5,541,061 | A | 7/1996 | Fodor et al. |
| 5,545,568 | A | 8/1996 | Ellman |
| 5,549,974 | A | 8/1996 | Holmes |
| 5,565,324 | A | 10/1996 | Still et al. |
| 5,571,698 | A | 11/1996 | Ladner et al. |
| 5,574,656 | A | 11/1996 | Agrafiotis et al. |
| 5,593,853 | A | 1/1997 | Chen et al. |
| 5,639,603 | A | 6/1997 | Dower et al. |
| 5,641,862 | A | 6/1997 | Rutter et al. |
| 5,684,711 | A | 11/1997 | Agrafiotis et al. |
| 5,688,696 | A | 11/1997 | Lebl |
| 5,688,997 | A | 11/1997 | Baldwin et al. |
| 5,698,673 | A | 12/1997 | Blondelle et al. |
| 5,708,153 | A | 1/1998 | Dower et al. |
| 5,721,099 | A | 2/1998 | Still et al. |
| 5,731,423 | A | 3/1998 | Kakarla et al. |
| 5,734,018 | A | 3/1998 | Rutter et al. |
| 5,741,713 | A | 4/1998 | Brown et al. |
| 2011/0149292 | A1* | 6/2011 | Himmelhaus ...... G01N 21/7746 356/454 |
| 2017/0021356 | A1* | 1/2017 | Dority ....................... B01L 7/52 |
| 2018/0085605 | A1 | 3/2018 | Maharbiz et al. |
| 2022/0297121 | A1* | 9/2022 | Appleyard ......... G01N 15/1459 |
| 2023/0120780 | A1* | 4/2023 | Blaicher ................ G02B 6/422 250/459.1 |
| 2023/0143102 | A1* | 5/2023 | Anwar .................. A61B 1/0684 382/128 |
| 2023/0160823 | A1* | 5/2023 | Hou .......................... B01L 7/52 435/6.12 |
| 2023/0184678 | A1* | 6/2023 | Schmid ................ C12Q 1/6869 250/458.1 |
| 2023/0204510 | A1* | 6/2023 | Cheah ................ G01N 21/6408 250/459.1 |
| 2024/0035802 | A1* | 2/2024 | Ma ..................... G01B 9/02051 |
| 2024/0042431 | A1* | 2/2024 | Hou .................. B01L 3/502715 |

FOREIGN PATENT DOCUMENTS

| | | |
|---|---|---|
| WO | WO1993/11161 | 6/1993 |
| WO | 2015052523 A1 | 4/2015 |
| WO | 2021016485 A1 | 1/2021 |

OTHER PUBLICATIONS

Chen, et al (2009) "A Wireless Capsule Endoscope System with Low-Power Controlling and Processing ASIC", IEEE Transactions on Biomedical Circuits and Systems, vol. 3, No. 1, Feb. 1, 2009, pp. 11-22.

Melino, et al (2020) "Capsule Endoscopy Compatible Fluorescence Imager Demonstrated Using Bowel Cancer Tumours", IEEE Sensors Journal, vol. 20, No. 17, Apr. 23, 2020, pp. 97633-9771.
Adamopoulos et al. (2019) "Electronic-Photonic Platform for Label-Free Biophotonic Sensing in Advanced Zero-Change CMOS-SOI Process", in Conference on Lasers and Electro-Optics, OSA Technical Digest.
Albota et al. (1998) "Two-photon fluorescence excitation cross sections of biomolecular probes from 690 to 960 nm", Applied Optics, 37: 7352-7356.
Ameri et al. (2019) "A 114GHz Biosensor with Integrated Dielectrophoresis for Single Cell Characterization", 3 pages.
Antaris et al. (2016) "A small-molecule dye for NIR-II imaging", Nature Materials, 15(2): 235-242.
Anwar et al. (2009) "A wireless-compatible optics-free fluorescent array reader", Applied Physics Letters, 94(11): 111102-1-111102-3.
Ayazian et al. (2011) "Delivering optical power to subcutaneous implanted devices", 2011 Annual International Conference of the IEEE Engineering in Medicine and Biology Society, pp. 2874-2877.
Backes et al. (2000) "Synthesis of positional-scanning libraries of fluorogenic peptide substrates to define the extended substrate specificity of plasmin and thrombin", Nature Biotechnology, 18: 187-193.
Biederman et al. (2013) "A Fully-Integrated, Miniaturized (0.125 mm2) 10.5 µW Wireless Neural Sensor", IEEE Journal of Solid-State Circuits, 48: 960-970.
Bindea et al. (2014) "The immune landscape of human tumors: Implications for cancer immunotherapy", OncoImmunology, 3(1): e27456-1-e27456-3.
Charthad et al. (2018) "A mm-Sized Wireless Implantable Device for Electrical Stimulation of Peripheral Nerves", IEEE Transactions on Biomedical Circuits and Systems, 12(2): 257-270.
Chien et al. (2018) "A high-throughput flow cytometry-on-CMOS for microwave-frequencies single-cell dielectric spectroscopy", Lab on a Chip, pp. 1-12.
Choi et al. (2020) "Fully Integrated Time-Gated 3D Fluorescence Imager for Deep Neural Imaging", IEEE Transactions on Biomedical Circuits and Systems, 14(4): 636-645.
Cox et al. (2001) "Automated Selection of Anti-Protein Aptamers", Bioorganic & Medicinal Chemistry, 9(10): 2525-2531.
Cox et al. (2002) "Automated selection of aptamers against protein targets translated in vitro: from gene to aptamer", Nucleic Acids Research, 30(20): e108(14 pages).
Cumber et al. (1992) "Comparative stabilities in vitro and in vivo of a recombinant mouse antibody FvCys fragment and a bisFvCys conjugate", The Journal of Immunology, 149(1): 120-126.
Desmet et al. (2014) "Structural basis of IL-23 antagonism by an Alphabody protein scaffold", Nature Communications, 5(5237): 1-12.
Duriseti et al. (2010) "Antagonistic Anti-urokinase Plasminogen Activator Receptor (uPAR) Antibodies Significantly Inhibit uPAR-mediated Cellular Signaling and Migration", Journal of Biological Chemistry, 285(35): 26878-26888.
Ebersbach et al. (2007) "Affilin-Novel Binding Molecules Based on Human γ-B-Crystallin, an All β-Sheet Protein", Journal of Molecular Biology, 372(1): 172-185.
Ehrlich et al. (1980) "Isolation of an Active Heavy-chain Variable Domain from a Homogeneous Rabbit Antibody by Cathepsin B Digestion of the Aminoethylated Heavy Chain", Biochemistry, 19(17): 4091-4096.
Emens et al. (2017) "Cancer immunotherapy: Opportunities and challenges in the rapidly evolving clinical landscape", European Journal of Cancer, 81: 116-129.
Escobedo et al. (2010) "NIR dyes for bioimaging applications", Current Opinion in Chemical Biology, 14(1): 64-70.
Fletcher et al. (2000) "Near-field infrared imaging with a microfabricated solid immersion lens", Applied Physics Letters, 77(14) : 2109-2111.
Frangioni, John V. (2008) "New Technologies for Human Cancer Imaging", Journal of Clinical Oncology, 26(24): 4012-4021.
Galli et al. (2020) "Relevance of immune cell and tumor microenvironment imaging in the new era of immunotherapy", Journal of Experimental and Clinical Cancer Research, 39(89): 1-21.

(56) References Cited

OTHER PUBLICATIONS

Gao et al. (2004) "In Vivo Cancer Targeting and Imaging with Semiconductor Quantum Dots", Nature Biotechnology, 22(8): 969-976.

Gao et al. (2010) "Near-Infrared Quantum Dots as Optical Probes for Tumor Imaging", Current Topics in Medicinal Chemistry, 10(12): 1147-1157.

Garon et al. (2019) "Five-Year Overall Survival for Patients with Advanced Non-Small-Cell Lung Cancer Treated with Pembrolizumab: Results from the Phase I KEYNOTE-001 Study", Journal of Clinical Oncology, 37(28): 2518-2527.

Ghanbari et al. (2020) "Optimizing Volumetric Efficiency and Backscatter Communication in Biosensing Ultrasonic Implants", IEEE Transactions on Biomedical Circuits and Systems, 14(6): 1381-1392.

Gharia et al. (2020) "Signal to Noise Ratio as a Cross-Platform Metric for Intraoperative Fluorescence Imaging", Molecular Imaging, 19(1536012120913693): 1-14.

Ghosh et al. (2011) "Miniaturized integration of a fluorescence microscope", Nature Methods, 8(10): 871-878.

Grabulovski et al. (2007) "A Novel, Non-immunogenic Fyn SH3-derived Binding Protein with Tumor Vascular Targeting Properties", The Journal of Biological Chemistry, 282(5): 3196-3204.

Haque et al. (2017) "Next Generation NIR Fluorophores for Tumor Imaging and Fluorescence-Guided Surgery: A review", Bioorganic and Medicinal Chemistry, 25(7): 2017-2034(47 pages).

Haslam et al. (2019) "Estimation of the Percentage of US Patients with Cancer Who Are Eligible for and Respond to Checkpoint Inhibitor Immunotherapy Drugs", JAMA Network Open, 2(5): e192535(9 pages).

Heymes et al. (2018) "Implantable CMOS Pixel Sensor for Positron Imaging in Rat Brain", Nuclear Instruments and Methods in Physics Research Section A: Accelerators, Spectrometers, Detectors and Associated Equipment, 911(24): 1-10.

Hilderbrand et al. (2010) "Near-infrared fluorescence: application to in vivo molecular imaging", Current Opinion in Chemical Biology, 14(1): 71-79.

Hodi et al. (2010) "Improved Survival with Ipilimumab in Patients with Metastatic Melanoma", The New England Journal of Medicine, 363(8): 711-723.

Holliger et al. (1993) ""Diabodies": Small bivalent and bispecific antibody fragments", Proc. Natl. Acad. Sci. U.S.A., 90: 6444-6448.

Hong et al. (2011) "Near-infrared-fluorescence-enhanced molecular imaging of live cells on gold substrates", Angewandte Chemie International Edition, 50(20): 4644-4648.

Huston et al. (1988) "Protein engineering of antibody binding sites: recovery of specific activity in an anti-digoxin single-chain Fv analogue produced in *Escherichia coli*", Proc. Natl. Acad. Sci. U.S.A., 85(16): 5879-5883.

Inbar et al. (1972) "Localization of Antibody-Combining Sites within the Variable Portions of Heavy and Light Chains", Proc. Natl. Acad. Sci. U.S.A., 69(9): 2659-2662.

Ito et al. (2017) "Near-Infrared Photochemoimmunotherapy by Photoactivatable Bifunctional Antibody-Drug Conjugates Targeting Human Epidermal Growth Factor Receptor 2 Positive Cancer", Bioconjugate Chemistry, 28(5): 1-39.

Johnson et al. (2012) "Sensitive Affimer and Antibody Based Impedimetric Label-Free Assays for C-Reactive Protein", Analytical Chemistry, 84(15): 6553-6560.

Kang et al. (2016) "Current clinical trials testing the combination of immunotherapy with radiotherapy", Journal for ImmunoTherapy of Cancer, 4(51): 1-20.

Karimi et al. (2021) "Wireless Power and Data Transmission for Implanted Devices via Inductive Links: A Systematic Review", IEEE Sensors Journal, 21(6): 7145-7161.

Kaufman et al. (2013) "The Society for Immunotherapy of Cancer consensus statement on tumour immunotherapy for the treatment of cutaneous melanoma", Nature Reviews Clinical Oncology, 10(10): 588-598.

Kenan et al. (1999) "In Vitro Selection of Aptamers from RNA Libraries", Methods in Molecular Biology, 118: 217-231.

Ko et al. (2018) "Radiotherapy and checkpoint inhibitors: a winning new combination?", Therapeutic Advances in Medical Oncology, 10: 1-11.

Kobayashi et al. (2016) "Optical communication with brain cells by means of an implanted duplex micro-device with optogenetics and Ca2+ fluoroimaging", Scientific Reports, 6(21247): 1-13.

Koide et al. (2007) "Monobodies: antibody mimics based on the scaffold of the fibronectin type III domain", Methods in Molecular Biology, 352: 95-109.

Krehenbrink et al. (2008) "Artificial Binding Proteins (Affitins) as Probes for Conformational Changes in Secretin PulD", Journal of Molecular Biology, 383(5): 1058-1068.

Lebeau et al. (2013) "Targeting uPAR with Antagonistic Recombinant Human Antibodies in Aggressive Breast Cancer", Cancer Research, 73(7): 2070-2081.

Lebeau et al. (2014) "Imaging the Urokinase Plasminongen Activator Receptor in Preclinical Breast Cancer Models of Acquired Drug Resistance", Theranostics, 4(3): 267-279.

Lyu et al. (2016) "Generating Cell Targeting Aptamers for Nanotheranostics Using Cell-SELEX", Theranostics, 6(9): 1440-1452.

Nanda et al. (2017) "Pembrolizumab plus standard neoadjuvant therapy for high-risk breast cancer (BC): Results from I-SPY 2", Journal of Clinical Oncology, 35(15_suppl): 506.

Nygren, P. (2008) "Alternative binding proteins: Affibody binding proteins developed from a small three-helix bundle scaffold", FEBS Journal, 275(11): 2668-2676.

Orlova et al. (2006) "Tumor Imaging Using a Picomolar Affinity HER2 Binding Affibody Molecule", Cancer Research, 66(8): 4339-4348.

Pack et al. (1992) "Miniantibodies: Use of Amphipathic Helices to Produce Functional, Flexibly Linked Dimeric Fv Fragments with High Avidity in *Escherichia coli*", Biochemistry, 31(6): 1579-1584.

Page et al. (2015) "Non-invasive imaging and cellular tracking of pulmonary emboli by near-infrared fluorescence and positron-emission tomography", Nature Communications, 6(8448): 1-11.

Pai et al. (2019) "Clonal Deletion of Tumor-Specific T Cells by Interferon-γ Confers Therapeutic Resistance to Combination Immune Checkpoint Blockade", Immunity, 50(2): 477-492.

Papageorgiou et al. (2016) "An angle-selective CMOS imager with on-chip micro-collimators for blur reduction in near-field cell imaging", MEMS, pp. 337-340.

Papageorgiou et al. (2017) "Chip-Scale Fluorescence Imager for In Vivo Microscopic Cancer Detection", 2017 Symposium on VLSI Circuits Digest of Technical Papers, pp. C106-C107.

Papageorgiou et al. (2018) "Angle-insensitive amorphous silicon optical filter for fluorescence contact imaging", Optics letters, 43(3): 354-357.

Papageorgiou et al. (2018) "Imaging of IR700DX Labeled Mouse Breast Tumor Using a Custom Angle-Selective Fluorescence Contact Imaging System", Annual International Conference of the IEEE Engineering in Medicine and Biology Society, pp. 1588-1591.

Papageorgiou et al. (2018) "Real-time cancer detection with an integrated lensless fluorescence contact imager", Biomedical Optics Express, 9(8): 3607-3623.

Papageorgiou et al. (2020) "Chip-Scale Angle-Selective Imager for In Vivo Microscopic Cancer Detection", IEEE Transactions on Biomedical Circuits and Systems, 14(1): 91-103.

Piech et al. (2020) "A wireless millimetre-scale implantable neural stimulator with ultrasonically powered bidirectional communication", Nature Biomedical Engineering, 4(2): 207-222.

Platella et al. (2016) Biochim. Biophys. Acta Nov. 16 pii: S0304-4165(16)30447-0.

Plückthun, A. (1993) "Antibodies from *Escherichia coli*", Handbook of Experimental Pharmacology, The Pharmacology of Monoclonal Antibodies(Rosenberg, M. and Moore, G. P., eds.), Springer-Verlag, Berlin, Heidelberg, 113: 269-315.

Qi et al. (2016) "Long-term intravital imaging of the multicolor-coded tumor microenvironment during combination immunotherapy", eLife, 5(e14756): 1-28.

(56) References Cited

OTHER PUBLICATIONS

Rabbani et al. (2021) "Towards an Implantable Fluorescence Image Sensor for Real-Time Monitoring of Immune Response in Cancer Therapy", EMBC, 5 pages.

Riechmann et al. (1988) "Reshaping human antibodies for therapy", The Journal of Immunology, 332: 323-327.

Rosenberg, Steven A. (2004) "Shedding Light on Immunotherapy for Cancer", New England Journal of Medicine, 350(14): 1461-1463.

Saad et al. (2015) "Transperineal implantation of gold fiducial markers (gold seeds) for prostate image-guided radiation therapy: a feasible technique associated with a low risk of complications", Journal of Medical Radiation Sciences, 62: 261-266.

Sawaby et al. (2018) "A Wireless Implantable Ultrasound Array Receiver for Thermoacoustic Imaging", 2018 Symposium on VLSI Circuits Digest of Technical Papers, pp. 189-190.

Seo et al. (2016) "Wireless Recording in the Peripheral Nervous System with Ultrasonic Neural Dus", Neuron, 91(3): 529-539.

Sharma et al. (2017) "Primary, Adaptive, and Acquired Resistance to Cancer Immunotherapy", Cell, 168(4): 707-723.

Silverman et al. (2005) "Multivalent avimer proteins evolved by exon shuffling of a family of human receptor domains", Nature Biotechnology, 23(12): 1556-1561.

Singh et al. (2010) "A CMOS/Thin-Film Fluorescence Contact Imaging Microsystem for DNA Analysis", IEEE Transactions on Circuits and Systems I: Regular Papers, 57(5): 1029-1038.

Skerra, A. (2008) "Alternative binding proteins: Anticalins—harnessing the structural plasticity of the lipocalin ligand pocket to engineer novel binding activities", FEBS Journal, 275(11): 2677-2683.

Stumpp et al. (2008) "DARPins: A new generation of protein therapeutics", Drug Discovery Today, 13(15-16): 695-701.

Sun et al. (2015) "Single-chip microprocessor that communicates directly using light", Nature, 528(7583): 534-538.

Sunaga et al. (2016) "Implantable imaging device for brain functional imaging system using flavoprotein fluorescence", Japanese Journal of Applied Physics, 55(3S2): 03DF02-1-03DF02-5.

Thimot et al. (2017) "Bioelectronic devices: Wirelessly powered implants", Nature Biomedical Engineering, 1: 1-2.

Truillet et al. (2018) "Imaging PD-L1 Expression with ImmunoPET", Bioconjugate Chemistry, 29(1): 96-103.

Vanpouille-Box et al. (2015) "TGFB Is a Master Regulator of Radiation Therapy-Induced Antitumor Immunity", Cancer Research, 75(11): 2232-2242.

Vats et al. (2017) "Near Infrared Fluorescence Imaging in Nano-Therapeutics and Photo-Thermal Evaluation", International Journal of Molecular Sciences, 18(5): 924(19 pages).

Verhoeyen et al. (1988) "Reshaping Human Antibodies: Grafting an Antilysozyme Activity", Science, 239(4847):1534-1536.

Victor et al. (2015) "Radiation and dual checkpoint blockade activate non-redundant immune mechanisms in cancer", Nature, 520(7547): 373-377.

Vincke et al. (2012) "Introduction to Heavy Chain Antibodies and Derived Nanobodies", Methods in Molecular Biology, 911: 15-26.

Wang et al. (2005) "Optical properties of Alexa 488 and Cy5 immobilized on a glass surface", Biotechniques, 38(1): 127-132.

Wang et al. (2016) "Nanobody-derived nanobiotechnology tool kits for diverse biomedical and biotechnology applications", International Journal of Nanomedicine, 11: 3287-3303.

Weber et al. (2018) "A Miniaturized Single-Transducer Implantable Pressure Sensor with Time-Multiplexed Ultrasonic Data and Power Links", IEEE Journal of Solid-State Circuits, 53(1): 1089-1101.

Winter et al. (1991) "Man-made antibodies", Nature, 349: 293-299.

Ye et al. (2019) "Tumor-Infiltrating Immune Cells Act as a Marker for Prognosis in Colorectal Cancer", Frontiers in Immunology, 10(2368): 1-12.

Yuan et al. (2013) "Far-red to near infrared analyte-responsive fluorescent probes based on organic fluorophore platforms for fluorescence imaging", Chemical Society Reviews, 42: 622-661.

Zhang et al. (2017) "Beyond the margins: Real-time detection of cancer using targeted fluorophores", Nature Reviews Clinical Oncology, 14(6): 347-364.

Zhao et al. (2018) "Near infrared quantum dots in biomedical applications: current status and future perspective", Wiley Interdisciplinary Reviews Nanomedicine and Nanobiotechnology, 10(3): e1483(16 pages).

* cited by examiner

Imaging of Isolated Cell Clusters

Imaging of Isolated Cell Clusters

Automated Image Analysis

Automated Image Analysis

FIG. 4E          anti-uPAR LabelsAggressive Cancers
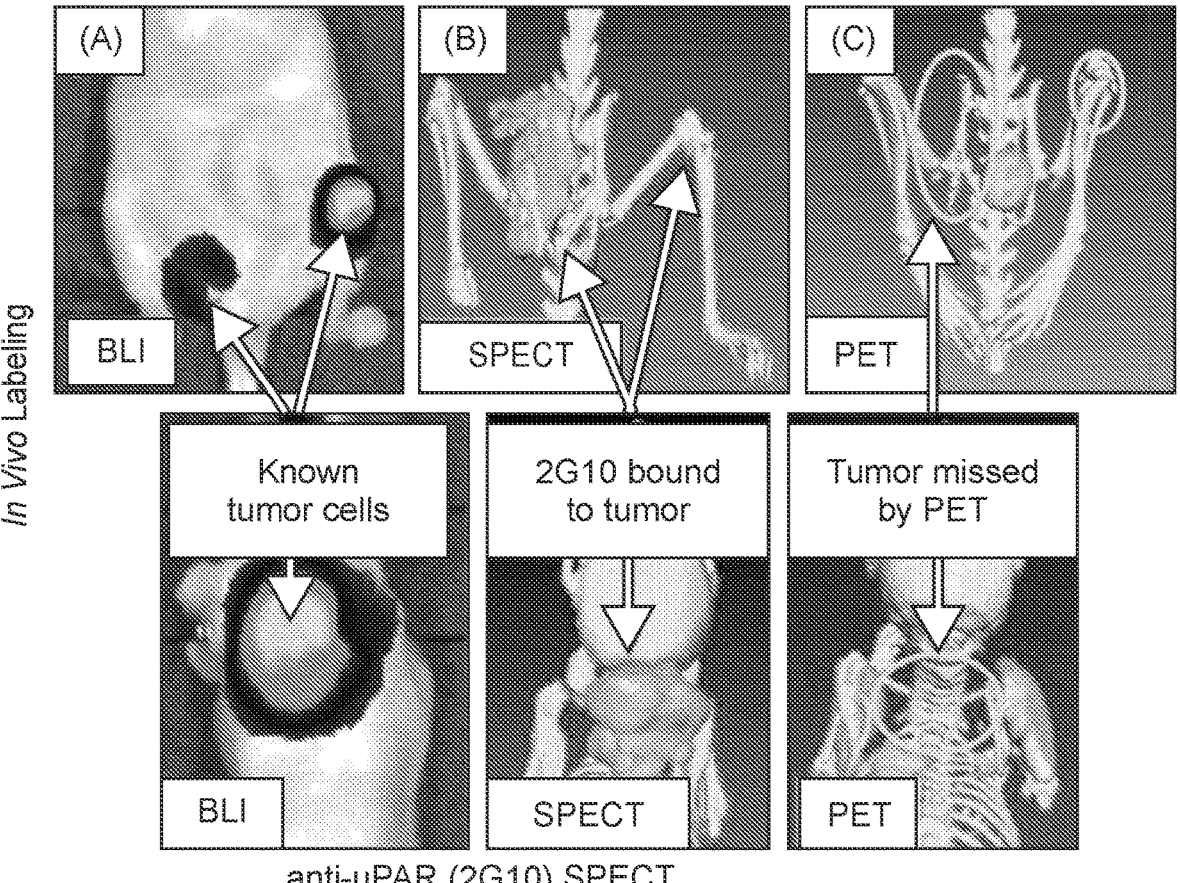
anti-uPAR (2G10) SPECT
Imaging
anti-uPAR Labels Aggressive Cancers
MDA-MB-231
FIG. 4F
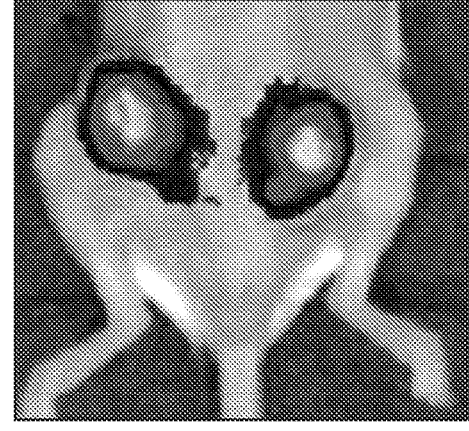
anti-uPAR (2G10)
-AF680 fluorescence imaging Conventional "RGB"
Color Imaging Multi-Fluorophore Imaging
with Amoprous Silicon Filters Sensor #1

Cell

~5-10 mm

Sensor #2

Drop-port
Photodetector

Waveguide

Microring
Modulator

Tuning
Controller
Frontend

Modulator
Driver
Circuit

50 μm

Transmitter

Digital Circuits
Backend and
Tuning Controller

Features:
- Highly flexible structured illumination
- 3D Imaging
- Multi-color/multi-cellular Imaging Laser Driver

ADC

Power Harvester and Backscattering Modulator

LDOs

FSM for Digital Control

Array Readout Control

Pixel Array 5 mm 2.5 mm

Die Photo

Block Diagram

Timing Diagram

Mouse Models - T-Cell Infiltration

Change in T-cell indicate immune response to treatment in cancer (pics taken with standard microscope)

Figure 18:
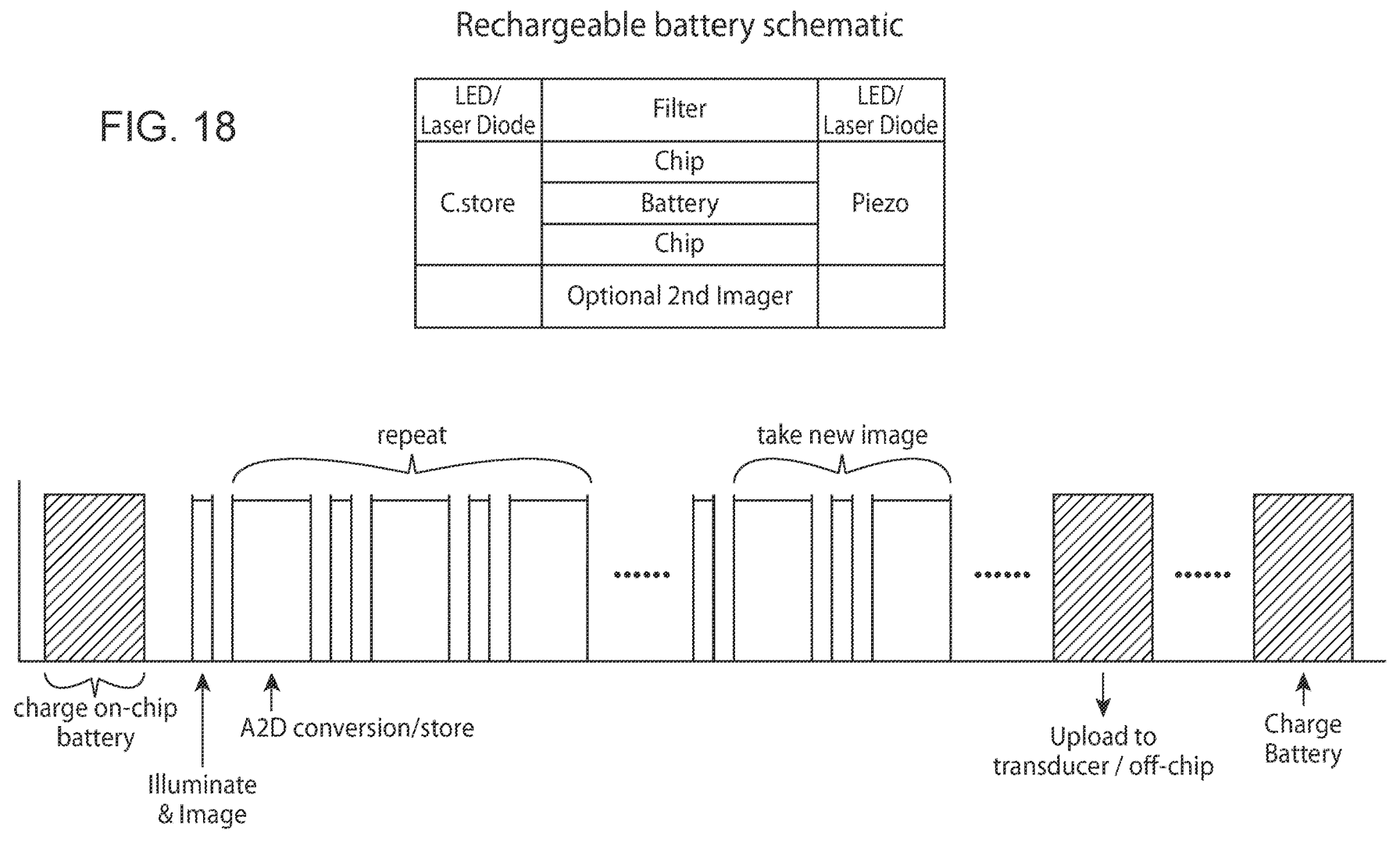

Rechargeable battery schematic

| LED/<br>Laser Diode | Filter | | LED/<br>Laser Diode |
| | Chip | | Piezo |
| C.store | Battery | | |
| | Chip | | |
| | Optional 2nd Imager | | |

Figure 19:
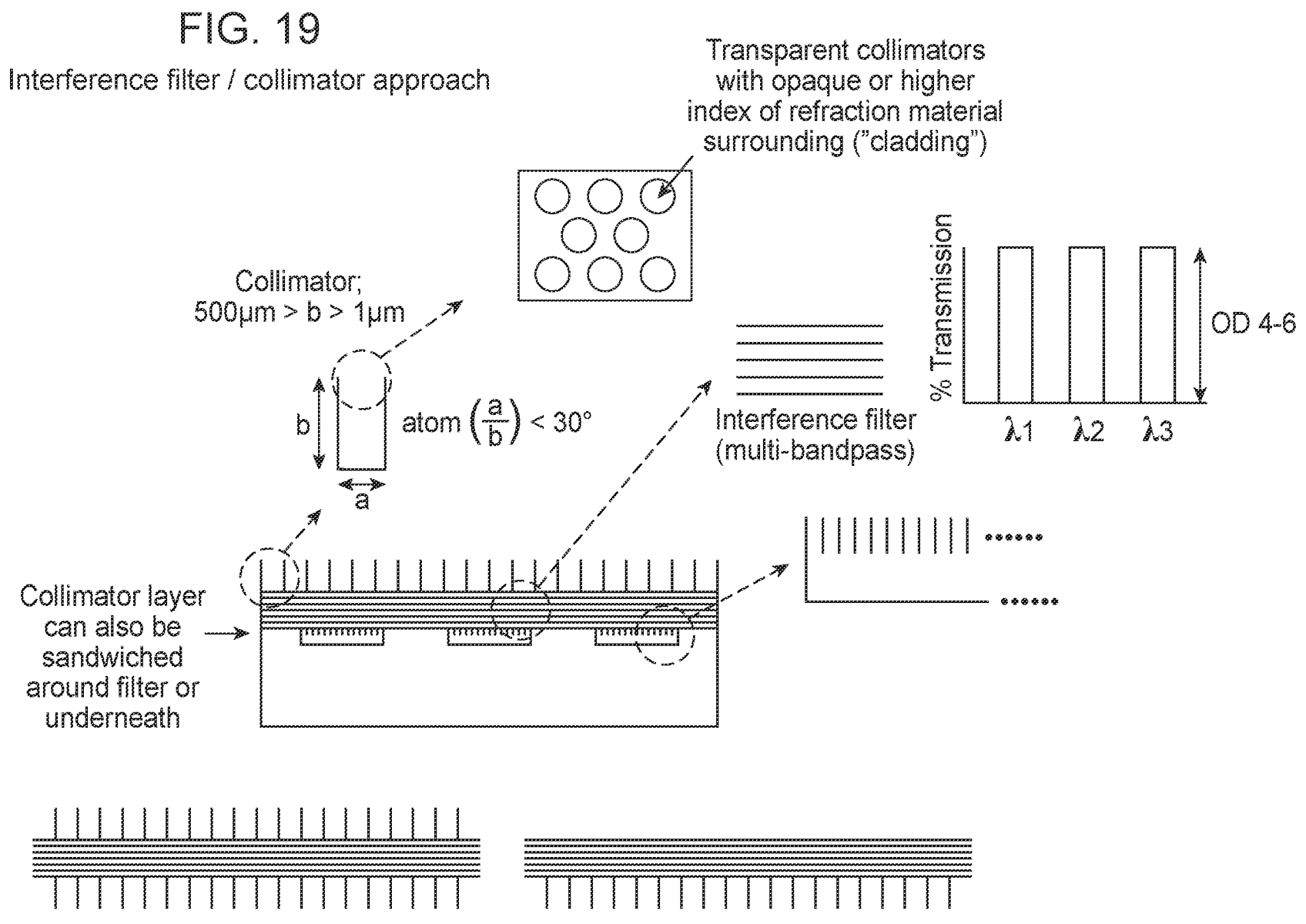

Interference filter / collimator approach

Transparent collimators with opaque or higher index of refraction material surrounding ("cladding")

Collimator; 500μm > b > 1μm atom $\left(\dfrac{a}{b}\right)$ < 30°

Interference filter (multi-bandpass)

% Transmission

λ1  λ2  λ3

OD 4-6

Collimator layer can also be sandwiched around filter or underneath

☐ Power Transfer

○ High power transfer density

○ Low tissue attenuation with depth

○ Small form factor

☐ Data communication

○ Ultrasound backscattering

○ Pulse-echo scheme

1) Power management unit

1) Power management unit
2) Digital control
3) Laser diode driver

1) Power management unit
2) Digital control
3) Laser diode driver
4) Image acquisition unit 2. The laser diode turns on to illuminate the target and the image is captured by the pixels

Figure 40:
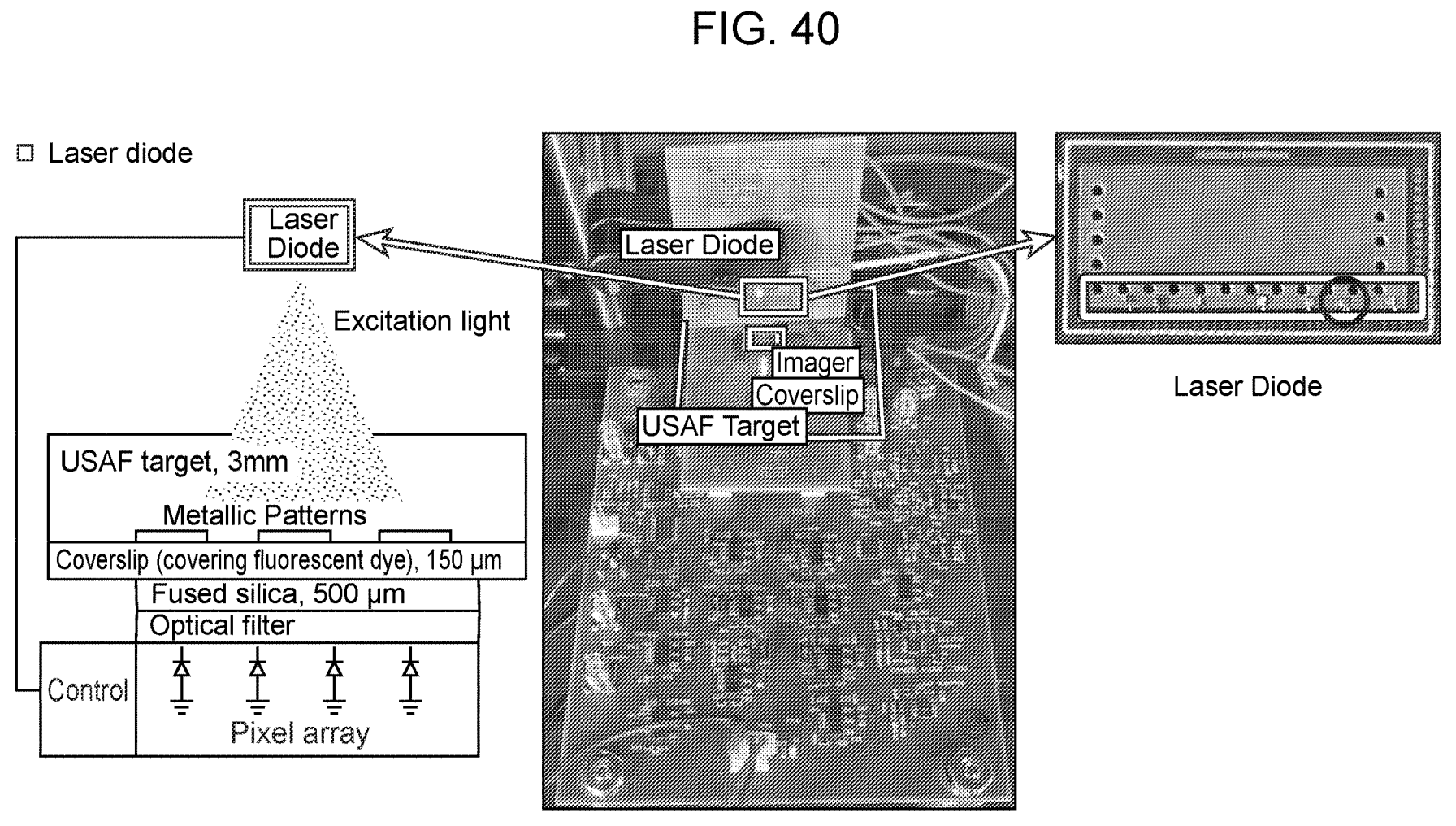

Laser Diode

Laser Diode

Imager
Coverslip
USAF Target

Laser diode

Laser Diode

Excitation light

USAF target, 3mm

Metallic Patterns

Coverslip (covering fluorescent dye), 150 μm

Fused silica, 500 μm

Optical filter

Pixel array

Control

| | [1] | [2] | [5] | This work |
|---|---|---|---|---|
| Imaging method | Fluorescence | Fluorescence | Thermoacoustic | Fluorescence |
| Multi-cellular resolution | Yes | Yes | No | Yes |
| Technology | 0.35 µm CMOS | 0.13 µm CMOS | 65 nm CMOS | 0.18 µm CMOS |
| Wireless | No | No | Yes | Yes |
| Power source | Power supply | Power supply | Ultrasound | Ultrasound |
| Array size | 120 x 268 | 8 x 64 | 1 x 16(a) | 36 x 40 |
| Pixel size | 7.5 x 7.5 µm² | 25.3 x 51.2 µm² | -- | 55 x 55 µm² |
| Excitation time | -- | 2 ns | 5 µs | 16-128 ms |
| Excitation source | µLED | Laser diode | RF | Laser diode |
| Excitation power | -- | -- | -- | 3.4 mW |
| Implant depth | -- | -- | 6 cm | 2 cm |
| Data transmitted per frame | Analog | Digital/ 3 kbits | Digital/ 72(b) kbits | Digital/ 11.5 kbits |
| Imager power | -- | 14.1 mW | 1.5 mW | 0.26 mW |
| System average power per frame (including excitation) | -- | -- | -- | 0.055 mW |

(a) Number of CMUT channels (b) Estimated 144 bits based on 9-bit ADC and 16 channels, 72 kbit based on memory size

IMPLANTABLE IMAGERS FOR IN VIVO IMAGING

STATEMENT REGARDING FEDERALLY SPONSORED RESEARCH OR DEVELOPMENT

This invention was made with government support under W81XWH-15-1-0531 awarded by the Defense Advanced Research Projects Agency, and R21 EB027238, and DE030713 awarded by the National Institutes of Health. The government has certain rights in the invention.

BACKGROUND OF THE INVENTION

The recent advent of immuno-oncology (IO) therapy—a powerful approach that unlocks the body's own immune system to fight cancer—is fundamentally changing how cancer is treated for the 1.7 million people diagnosed each year in the US, of which over 600,000 die. For example, in melanoma, immune checkpoint inhibitors nearly doubled overall survival (Hodi et al. N. Engl. J. Med. 363(8):711 (2010)), and similarly in metastatic kidney cancer 18-month survival was improved from 60% to 75%. Immunotherapy has promise in breast cancer, the most common cancer among women, with over 250,000 cases annually. In a trial of advanced breast cancer (Nanda et al. J. Clin. Oncol. 35(15_suppl):506 (2017)), pembrolizumab increased the rate of pathologic complete response, a surrogate for improved clinical outcomes threefold, compared to standard chemotherapy, motivating our demonstration in a model system of breast cancer. The promise of these therapies has led to an explosive growth in drug development, with over 3,000 agents in the clinical pipeline and over 800 active clinical trials. However, less than 50% of patients obtain a durable response to IO therapy, and considerable effort is focused on identifying who will respond.

For patients who do not respond initially to immuno-therapy, the opportunity for new combinations that synergize with immuno-oncology drugs is particularly exciting, shift-ing an unresponsive or "cold" immune microenvironment to a responsive or "hot" phenotype and a host of promising strategies are emerging accomplish this. Conventional meth-ods of imaging and blood-based biomarkers have made progress, but to date, do not provide a complete picture of immediate intratumoral response, and the gold-standard for response assessment remains a biopsy—impractical on a repeated basis. Significant progress aimed at characterizing tumor tissue for immune responsiveness still falls short of accurately predicting patient response. The complexity of the dynamic interplay between the tumor microenvironment and host immune system requires real-time intratumoral monitoring for treatment response. This internal response is robust to patient-to-patient heterogeneity, and circumvents our incomplete understanding of all factors in the immune response. Currently, clinical response to IO therapy is assessed by radiographic signs (iRESIST). Widely utilized in clinical practice, this large-scale radiographic change is only a proxy for true response, and takes months to manifest. Waiting during these critical months sacrifices the patients most precious commodity—time, and allows cancer to prog-ress, making cure less likely. This costly, delayed feedback loop, with no true knowledge of response, hinders rapid deployment of therapies that modulate the immune environ-ment. A platform capable of conveying immediate response within the tumor itself is critically needed.

SUMMARY OF THE INVENTION

Devices, systems, and methods are provided for in vivo fluorescence imaging. Disclosed herein is an implantable miniature fluorescence imager capable of single or multi-color imaging, on a chip having a custom imaging array with angle-selective structures such as microcollimators or angle selective gratings for image deblurring, and optical filters that can be tuned to image fluorescence from multiple fluorophores simultaneously. Power is supplied by an on-chip power source or transmitted to the chip from an external transducer, or a combination of both, whereby the on-chip power source is recharged periodically from an external transducer. Data can be wirelessly transmitted or stored in on-chip memory and then transmitted, or transmitted con-tinuously or at intervals of time. For example, an ultrasound transducer can be used to supply power wirelessly to the imager through a piezoelectric crystal/ceramic incorporated into the integrated circuit. Alternatively, electromagnetic power transfer can also be implemented from an external inductor coil worn outside the patient, to an internal inductor coil on the implant. Alternatively or additionally, power can be provided by an on-chip battery, which can be periodically charged by an external transducer, or power can be provided by an environmental source or other on-chip power source. Wireless communication may be provided by electromag-netic (e.g., radiofrequency, microwave, or infrared carrier wave) or ultrasound links to the device. The function of a fluorescence microscope is thus provided in a millimeter-scale device that can be readily implanted in tissue and used to image fluorescently labeled cells in vivo. The small size of the fluorescence imager makes possible sustained in vivo imaging with real-time monitoring of multiple cell types within diseased tissue or a tumor.

In one aspect, a fluorescence imager is provided, com-prising: a) an imaging array comprising a plurality of photodiodes arrayed on the surface of a chip, wherein each photodiode is coated with at least one layer of filter material that functions as an optical filter; b) a plurality of light emitting sources to provide excitation light, wherein the plurality of light emitting sources are located on the chip or externally; c) an on-chip or off-chip energy storage device to supply power for operation of the fluorescence imager; d) a data storage unit in communication with the imaging array, wherein the data storage unit stores imaging data from the imaging array; and e) an application-specific integrated circuit (ASIC) configured to control voltages and supply power from the on-chip or off-chip energy storage device to the imaging array, the plurality of light emitting sources on the chip, and the data storage unit. In some embodiments, the fluorescence imager has dimensions of less than or equal to 5 mm in length.

In certain embodiments, pixels are coated or covered with a layer of material that acts to deblur incoming light. In some embodiments, the layer of material comprises angle selec-tive gratings directly patterned on the pixels. In some embodiments, the layer of material comprises planar arrays of collimators or fiber optics that are positioned between the incoming light and the optical filter.

In certain embodiments, the light emitting sources are micro-laser diodes or light-emitting diodes (LEDs). These light sources may emit light of a single color (wavelength) or multiple colors (wavelengths) so as to illuminate multiple fluorophores. Multiple light sources of the same and/or different wavelength emissions may be arrayed on the chip, and used in parallel or serially to illuminate the tissue. In some embodiments, the LEDs further comprise emission filters. In other embodiments, LEDs having a tight full-width half maximum spread are used without emission filters.

In certain embodiments, the plurality of light emitting sources are located externally. In some embodiments, the external light emitting source is on a separate chip that is implantable in tissue. For example, a "micro-star" external light source can be used to illuminate tissue. In some embodiments, the micro-star comprises a laser diode emitting light at a single wavelength or multiple laser diodes emitting light at different wavelengths. For example, a micro-star may comprise two laser diodes emitting light at two different wavelengths, three laser diodes emitting light at three different wavelengths; etc. In certain embodiments, a micro-star comprises LEDs instead of laser diodes. When LEDs are used, an emission filter can be used to prevent wavelengths of light from being in the passband of the corresponding optical filter. Micro-stars can be designed such that the wavelength of the light emitted from each laser diode or LED overlaps an intended fluorophore and does not overlap the emission wavelength of a simultaneously imaged fluorophore. The same arrangement of LEDs or laser diodes that is used on a micro-star can also be incorporated onto a corresponding fluorescence imager chip.

In certain embodiments, the on-chip or off-chip energy storage device is a battery or a capacitor. In some embodiments, a battery and a capacitor are used to store the levels of power needed to operate the chip. In some embodiments, the battery is a rechargeable battery. In some embodiments, the fluorescence imager comprises an on-chip energy source comprising radionuclides, from which power is harvested directly or indirectly (through optical conversion and harvesting via photovoltaics). This power is then used to charge a battery or capacitor, or power the system directly. In some embodiments, the fluorescence imager comprises an on-chip photovoltaic system or a radionuclide in combination with a scintillator and photovoltaic energy harvester to provide power to the fluorescence imager chip.

In certain embodiments, the fluorescence imager further comprises a piezoelectric substrate attached to the surface of the chip, wherein the piezoelectric substrate is configured in the ASIC to receive ultrasound power from an external ultrasound transducer and supply power for operation of the fluorescence imager and the miniaturized illumination source, wherein electrical energy output from the piezoelectric substrate in response to receiving the ultrasound power is rectified and stored in the on chip-energy storage device. In some embodiments, the energy storage device (e.g., storage capacitor) is off chip. In some embodiments the piezoelectric substrate and/or other elements such as the storage capacitor are assembled on a solid support (e.g., flexible board) containing the chip. In some embodiments, the piezoelectric substrate is a piezoelectric crystal or piezoelectric ceramic (e.g., lead zirconate titanate (PZT), or other piezoelectric material as described further below).

In certain embodiments, the fluorescence imager further comprises an on-chip antenna configured to receive radiofrequency (RF) power from an external RF transducer and supply power for operation of the fluorescence imager, wherein electrical energy output from the on-chip antenna in response to receiving the RF power is stored in the on-chip energy storage device.

In certain embodiments, the fluorescence imager further comprises an on-chip antenna configured to receive electromagnetic power inductively transferred to a coil from an external transducer.

In certain embodiments, the off chip-energy storage device is a capacitor or rechargeable battery that stores electrical energy output from a piezoelectric substrate in response to receiving the ultrasound power or an antenna in response to receiving RF power or electromagnetic power, wherein the capacitor or a rechargeable battery supplies power to the plurality of light emitting sources and the imaging array. In certain embodiments the energy storage device is on-chip. In some embodiments the piezoelectric and/or energy storage device (e.g., battery or storage capacitor) are assembled on a solid support (e.g., flexible board) containing the chip In certain embodiments, the ASIC further comprises a rectifier, wherein the rectifier converts current generated by the piezoelectric substrate to direct current (DC). In some embodiments, the ASIC further comprises a DC voltage regulator configured to regulate output voltage from the rectifier. The DC voltage regulator may include, for example, a low dropout regulator. In certain embodiments the power harvesting circuitry charges a battery. This DC voltage then charges a capacitor. Multiple voltage sources at various levels can be generated on chip. For example, 3.3 V, 2.5 V, 2.1 V, 1.8 V and 1 V which can then directly power circuitry on chip.

In certain embodiments, the ASIC further comprises a reference voltage generator. In some embodiments, the reference voltage generator is a bandgap voltage reference generator. In some embodiments, due to the well-regulated body temperature, the on-chip reference voltage generator is proportional to absolute temperature (PTAT).

In certain embodiments, the fluorescence imager further comprises a power-on-reset (POR) circuit.

In certain embodiments, the fluorescence imager further comprises a data processing unit in communication with the data storage unit.

In certain embodiments, the fluorescence imager further comprises an analog to digital converter in communication with the data storage unit. In certain embodiments, the fluorescence imager further comprises multiple analog to digital converters which then feed data into a storage buffer or memory which is then transmitted. This data can be transmitted at the time of imaging, or stored for subsequent transmission. The data can be averaged with subsequent images taken near the same time point.

In certain embodiments, the fluorescence imager further comprises a backscattering modulator unit in communication with the imaging array. In other embodiments, active telemetry modulation schemes such as amplitude shift keying (ASK), phase shift keying (PSK), frequency shift keying (FSK), pulse width modulation amplitude shift keying (PWM-ASK), pulse position modulation (PPM) and spectrally efficient quadrature amplitude modulation (QAM) can be used for data communication. In other embodiments, power and data carrier frequencies are separated to maximize bandwidth for data communication while minimizing the tissue attenuation by lowering the frequency of external carrier waveforms during power transfer. In certain embodiments, the fluorescence imager comprises a precharged battery, and does not receive external power or recharge. After discharging it remains, until removed (for example in the case of neoadjuvant therapy prior to surgery). It will have the ability to wirelessly transmit data.

In certain embodiments, the fluorescence imager comprises an envelope detector for the AC input, the output of which controls a finite state machine (FSM). The FSM generates multiple control/timing signals for proper operation of the internal blocks of the imager such as sample and conversion times of the analog to digital converter. The FSM also performs packet scheduling and timing of data uplink. The output of the envelope detector also acts as a downlink data stream that is used to wirelessly configure the imager settings such as integration time. In other embodiments wherein a precharged battery replaces the AC input, an input control signal keeps track of the transitions of the FSM by overriding the output of the timer control module.

In certain embodiments, the fluorescence imager further comprises a first wireless communication unit in communication with the data storage unit and an external data receiving device comprising a second wireless communication unit. In some embodiments, the first wireless communication unit utilizes a wireless communication protocol using an electromagnetic carrier wave (e.g., a radio wave, microwave, or an infrared carrier wave) or ultrasound to transfer data from the data storage unit to the external data receiving device comprising the second wireless communication unit. In some embodiments, the first wireless communication unit utilizes a radio-frequency communication protocol or an ultrasound communication protocol to transfer data from the data storage unit to the external data receiving device comprising the second wireless communication unit. In some embodiments, the data receiving device is a computer or handheld device (e.g., a cell phone or tablet). In certain embodiments, the fluorescence imager periodically takes images and stores data in the data storage unit on the chip. At either set time points or upon interrogation, the stored data can be wirelessly transmitted from the fluorescence imager to the external data receiving device.

In certain embodiments, the optical filter is an absorption filter having a band gap and thickness suitable to allow light at a fluorescence emission wavelength of a fluorophore of interest to pass through to the photodiode.

In certain embodiments, the optical filter is an interference filter. In some embodiments, the interference filter is a single bandpass, dual bandpass, triple bandpass, or quadruple bandpass interference filter. In some embodiments, the interference filter further comprises a layer of absorption filter material on top of the interference filter or underneath the interference filter.

In certain embodiments, the interference filter further comprises one or more layers of material comprising a plurality of angle selective gratings, collimators, or fiber optic plates that block light that is not incident within 30° of an axis perpendicular to the plane of the chip. In some embodiments, fiber optic plates are used that block light that is not incident within 6° of an axis perpendicular to the plane of the chip (e.g., having a FWHM of 12 degrees). In some embodiments, angle selective gratings are used that block light that is not incident within 15° of an axis perpendicular to the plane of the chip.

In some embodiments, the one or more layers of material comprising the plurality of angle selective gratings, collimators, or fiber optics is on top of the layer of filter material (between the filter and cells), underneath the layer of filter material (between the filter and photodiodes), or both on top and underneath the layer of filter material. In some embodiments, the angle selective gratings, collimators, or fiber optic plate are in a layer of material on top of the layer of filter material and block light that is not incident within 10°-15° of an axis perpendicular to the plane of the chip. In some embodiments, this layer on top of the layer of filter material has a thickness of about 100 microns to about 500 microns. In some embodiments, the angle selective gratings, collimators, or fiber optics are in a layer of material underneath the layer of filter material and block light that is not incident within 5°-30° of an axis perpendicular to the plane of the chip. In some embodiments, this layer underneath the layer of filter material has a thickness of about 8 microns or less. Surrounding the collimators or fiber optics may be a material that is opaque to the incident light such that only light passing through the collimators or fiber optics may pass through the filter. This ensures proper operation of interference-based filters which have an angle-dependent response, and whose performance decays with oblique angles of incidence. In certain embodiments, the interference filter may be deposited on either one or both surfaces of the fiber optic plate or directly on the imager chip. The interference filter may have any of the following filter characteristics: long-pass, short-pass, notch, bandpass, or a combination of any number of these characteristics.

In certain embodiments, the filter material comprises or consists of amorphous silicon, crystalline silicon, gallium phosphide, cadmium selenide, gallium arsenide, or indium phosphide.

In certain embodiments, the thickness of the layer of filter material is less than 100 microns. For example, the thickness of the layer of filter material may range from 1 micron to 100 microns, including any thickness within this range, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, or 100 microns in thickness. In some embodiments, the thickness of the layer of filter material on at least two photodiodes is different. In other embodiments, the thickness of the layer of filter material on all the photodiodes is the same.

In certain embodiments, the thickness of the layer of filter material is varied on the plurality of photodiodes to allow selection of light at different fluorescence emission wavelengths to allow fluorescence imaging with multiple fluorophores having different fluorescence emission spectra.

In certain embodiments, the fluorophore of interest has a fluorescence emission in the near-infrared or visible region of the electromagnetic spectrum, and the band gap and the thickness of the layer of filter material is chosen to allow selection of near-infrared light or visible light at the fluorescence emission wavelength of the fluorophore.

In certain embodiments, the fluorescence imager further comprises a clock.

In certain embodiments, the fluorescence imager has no optical lens.

The fluorescence imager may use an on-chip power source or an external power source. In embodiments, where the fluorescence imager comprises an on-chip power source, such as a battery (for example measuring <5 mm³), several regulators may be used to generate on-chip voltages for circuit operation and on-chip clock generation. In embodiments where the power is transferred from an external transducer, the fluorescence imager may comprise a voltage rectifier and several regulators to generate the on-chip voltages for circuit operation, and the clock may be derived from the transducer signal. An analog to digital converter (ADC) can also be included on the chip. In certain embodiments the ADC is an 8-bit differential SAR ADC with 0.5 V or 1 V maximum range. In other embodiments, the ADC is a 10-bit SAR ADC with 0.5 V or 1 V maximum range.

In other embodiments, 4 ADCs run simultaneously to decrease the conversion time, and their digital outputs are stored in an on-chip storage unit. Storage of digital output of the ADC minimizes the effect of leakage as the pixels are being read out sequentially and transmitted according to the communication protocol. This approach won't change the overall power consumption for analog to digital conversion since the total number of pixels is the same.

In other embodiments, the in-pixel sampling switches are made of thicker oxide devices to limit the leakage current due to subthreshold conduction of the devices during hold times. Thicker oxide devices cut down the leakage current by more than 2 orders of magnitude. In other embodiments, the transient decay of the individual pixel's voltage due to leakage can be estimated and characterized by conducting a series of measurements on the same pixel at different time-points. The reconstructed transient voltage waveform for each pixel is used to estimate the initial value of the pixel voltage by extrapolation.

In other embodiments, in-pixel ADCs minimize the analog to digital conversion time for the pixel array and circumvent the leakage problem and enable expanding the size of the imager array without compromising the frame rate. Multiple ADC types or architectures can be used. One example, to maintain the fill factor of the pixels, is to use an oversampling Sigma-Delta.

In certain embodiments, the fluorescence imager further comprises a digital state machine that controls the stage of operation of the chip. For example, the stages may include i) power up, during which energy is stored for the sensing (imaging) operation, ii) illumination and imaging, which may last for 10 ms to 100 ms (but may be shorter or longer), and iii) data transmission. In some embodiments, during the illumination stage, a laser diode is used that is supplied by a 33 mA current for 50 ms. In some embodiments the voltage range and current output of the laser driver can be programmed on chip. Just prior to the illumination stage, pixels are reset, and any offset is measured and stored in pixels. During the illumination stage, the pixel is activated and integrates fluorescent light. At the end of illumination, the pixel value is sampled and held in an in-pixel storage capacitor. Both the offset value and the fluorescence value from each pixel are serially fed to the analog to digital converter. The analog to digital converter converts this analog signal to a digital value which is transmitted off chip. In other embodiments, these values are stored on chip and transmitted at a later time on demand. It is understood to those skilled in the art that a variety of circuit design approaches can be used to accomplish these stages of operation. These stages can be triggered from an external transducer or guided by an internal clock.

In another aspect, a kit comprising a fluorescence imager (with or without an on-chip light source) is provided. If the fluorescence imager does not comprise an on-chip light source, the kit may further comprise an external light source such as a micro-star light source, as described herein. In some embodiments, the kit comprises a plurality of light emitting sources comprising multiple light sources emitting light at different excitation wavelengths suitable for generating fluorescence from multiple fluorophore conjugates bound to different target markers on cells of interest. These light sources may be activated simultaneously, or serially. The kit may further comprise instructions for using the fluorescence imager for in vivo fluorescence imaging. In certain embodiments, the kit further comprises at least one fluorophore conjugated to a binding agent that specifically binds to a cellular marker of interest. In some embodiments, the binding agent is an antibody, an antibody mimetic, a peptide, a peptoid, an aptamer, or a small molecule ligand that selectively binds to the cellular marker of interest. Cellular markers of interest may include, without limitation, a tumor-specific antigen, a tumor-associated antigen, or an immune activation marker. In some embodiments the kit contains multiple fluorophore conjugates with different binding agents conjugated to different fluorophores to enable imaging of multiple targets. In some embodiments, the kit further comprises a portable transducer to transmit power and receive data. The transducer may be an ultrasound transducer or RF-transducer. In some embodiments, the kit further comprises a biopsy needle for implanting a fluorescence imager or external light source (e.g., micro-star).

In certain embodiments, cells are labeled with a fluorescent dye (fluorophore) that is excited by a laser diode or LED. The fluorophores of interest may include, without limitation, Alexa Flour 350, Alexa Fluor 405, Alexa Fluor 430, Alexa Fluor 488, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, Alexa Fluor 790, IRDye 650, IRDye 680LT, IRDye 680RD, IRDye 700DX, IRDye 750, IRDye 8000 W, IRDye 800RS, Cy2, Cy3, Cy3.5, Cy5, Cy5.5, and Cy7. Laser and LED excitation wavelengths may include, without limitation, 375 nm, 455 nm, 473 nm, 515 nm, 520 nm, 488 nm, 635 nm, 650 nm, 660 nm, 680 nm, 760 nm, and 780 nm. In certain embodiments, a multi-bandpass filter or color filter is used for multi-color imaging of up to 3 fluorophores. Any combination of the prior listed fluorophores and laser wavelengths, without limitation, may be used. Of particular interest for dual color imaging is Alexa Fluor 488 and IRDye 680LT or Alexa Fluor 647 excited at 455 nm or 488 nm and 635 nm, 650 nm, or 660 nm, respectively. Of particular interest for tri-color imaging is Alexa Fluor 488, IRDye 680LT or Alexa Fluor 647, and IRDye 8000 W excited at 455 nm or 488 nm; 635 nm, 650 nm, or 660 nm; and 760 nm or 780 nm, respectively.

In another aspect, a system is provided, the system comprising a fluorescence imager, as described herein, an external power source, and an external data receiving device.

In some embodiments, the external power source is an ultrasound transducer, an electromagnetic (EM) transducer, an inductive transducer, or a radiofrequency (RF) transducer. In some embodiments, the external power source is portable. The external power source may be used to charge an on-chip battery that provides power to the chip.

In certain embodiments, the external data receiving device comprises a wireless communication unit. In some embodiments, the wireless communication unit utilizes a wireless communication protocol using an electromagnetic carrier wave (e.g., a radio wave, microwave, or an infrared carrier wave) or ultrasound to receive data from the internal data storage unit of the fluorescence imager. In some embodiments, the external data receiving device further comprises a processor programmed to process data received from the fluorescence imager and display fluorescence images. For example, the external data receiving device can be a computer or handheld device such as a cell phone or tablet.

In certain embodiments, the system further comprises a display component, wherein the display component is connected to the external data receiving device.

In certain embodiments, the system further comprises at least one fluorophore conjugate comprising a fluorophore conjugated to a binding agent that specifically binds to a cellular marker of interest. In some embodiments, the binding agent is an antibody, an antibody mimetic, a peptide, a peptoid, an aptamer, or a small molecule ligand that selectively binds to the cellular marker of interest. The cellular markers of interest may include, without limitation, a tumor-specific antigen, a tumor-associated antigen, immune cell marker, or an immune activation marker. In some embodiments, the system comprises a plurality of light emitting sources comprising multiple light sources emitting light at different excitation wavelengths suitable for generating fluorescence from multiple fluorophore conjugates bound to different target markers on cells of interest.

In another aspect, a method of in vivo fluorescence imaging is provided, the method comprising: a) implanting at least one fluorescence imager, described herein, in tissue of a subject; b) contacting a cell of interest with at least one fluorophore conjugate, wherein the fluorophore conjugate comprises a fluorophore conjugated to a binding agent that selectively binds to a marker on the cell of interest; and c) providing power to the fluorescence imager, wherein the plurality of light emitting sources located on the chip or externally provides excitation light at an excitation wavelength of the fluorophore, and the imaging array detects fluorescent light emitted from the fluorophore. In some embodiments, power is provided from an on-chip battery, an on-chip photovoltaic system, an on-chip radionuclide in combination with a scintillator and photovoltaic energy harvester, an external ultrasound transducer, an external electromagnetic (EM) transducer, an external inductive transducer, or an external radiofrequency (RF) transducer.

In certain embodiments, the method further comprises implanting a plurality of light emitting sources externally in the tissue of the subject. In some embodiments, a network of fluorescence imagers is implanted together with a "constellation" of external light emitting sources (e.g., micro-star light sources) in tumor tissue to illuminate the tissue from different angles (see, e.g., FIG. 11).

In some embodiments machine learning techniques are employed to improve image quality.

In certain embodiments, the tissue is diseased tissue or cancerous tissue.

In certain embodiments, the binding agent is an antibody, an antibody mimetic, a peptide, a peptoid, an aptamer, or a small molecule ligand that selectively binds to the cellular marker of interest. The cellular markers of interest may include, without limitation, a tumor-specific antigen, a tumor-associated antigen, or an immune activation marker. Exemplary cellular markers include, without limitation, urokinase plasminogen activator receptor (uPAR), urokinase plasminogen activator (uPA), PD-1, PD-L1, CTLA-4 CD4, Ly6G, CD8, CD69, CD25, perforin, granzyme b, granzyme k, alphafetoprotein (AFP), carcinoembryonic antigen (CEA), CA-125, MUC-1, epithelial tumor antigen (ETA), ras, and p53.

In certain embodiments, the tissue is contacted with at least two different fluorophore conjugates, wherein each fluorophore conjugate comprises a different fluorophore that emits fluorescent light at a different emission wavelength, and each fluorophore conjugate comprises a different binding agent that selectively binds to a different marker. In some embodiments, the different binding agents of the fluorophore conjugates selectively bind to markers that are selectively expressed on cells of the same cell-type or different cell-types. In some embodiments, a plurality of light emitting sources are used, wherein the plurality of light emitting sources comprises multiple light sources emitting light at different excitation wavelengths suitable for generating fluorescence from multiple fluorophore conjugates bound to different target markers on cells of interest.

BRIEF DESCRIPTION OF THE DRAWINGS

(FIG. 2A) Real time feedback drives rapidly optimized treatments for each patient. (FIG. 2B) Patients are injected with fluorescently tagged, targeted antibodies. Immediately detected poor response allows iteration of new agents—guiding selection of optimal regimens.

(FIG. 3A) On chip illumination with micro light emitting diodes (LED) or micro laser diodes and custom IC imager [21] with angle selective gratings (ASG) over each pixel for image deblurring. (FIG. 3B) Custom optical filter tuned to different fluorophores by varying thickness (IR700DX, ICG shown).

FIGS. 4A-4G. Chip-Based Imaging (FIG. 4A) 3D cell culture of fluorescently labeled tumor cells. (FIG. 4B) Chip image. (FIGS. 4C-4D) Automated cell cluster recognition quantifies sensitivity and specificity (>92%) (1). In Vivo Labeling (FIG. 4E) $^{111}$In-labeled anti-uPAR antibodies specifically target metastatic lesions in the MDA-MB-231 mouse tumor model Immunoreceptors. anti-uPAR labels tumors not visible by PET, demonstrating sensitivity. (FIG. 4F) Fluorescently tagged anti-uPAR (2G10) labeled triple negative breast cancer in vivo (29). (FIG. 4G) C4 labels PDL1 expressing melanoma (B16) in a black6 mice model (Craik Evans (9)).

(FIG. 6A) Focal illumination at the pixel level, similar in principle to confocal imaging, allows deconvolution of the image for increased resolution. (FIG. 6B) A similar principle can be applied to two sensors facing each other. (FIG. 6C) Example of Global Foundries silicon nanophotonics, with micron-scale photonics integrated with on-chip circuitry (from (12, 13)).

FIG. 18. Schematic of a chip-based fluorescence imager with a rechargeable battery. A miniaturized battery can be integrated into the system to provide multimodal operation of the imager with AC input (e.g., ultrasound, electromagnetic, or inductive interrogation) and a DC supply (battery). With use of a battery for on-chip energy storage, multiple images can be taken, averaged, processed, and saved on-chip, and data can be transferred to an external processor at either set time points or upon interrogation (e.g., from an external ultrasound or electromagnetic transducer). Multiple images can be taken after a full charging cycle of the battery, and recharging can be done when imaging is over. The battery can be recharged (e.g., via ultrasound, electromagnetic, or inductive power transfer) during rest hours when imaging is not needed (e.g., overnight).

FIG. 19. Schematic of a chip-based fluorescence imager illustrating an interference filter/collimator approach.

(FIG. 22A) Circuit block diagram of the IC (FIG. 22B) timing diagram of the Finite State Machine and the corresponding critical signals (FIG. 22C) detailed backscattering protocol.

(FIG. 24A) setup for measuring optical power of the laser diode driven by the on-chip laser driver (FIG. 24B) I-V characterization of the laser diode and its nominal operating point (FIG. 24C) voltage of the photodiode in PM100D power meter during a 96 ms illumination interval (d) 50% duty-cycled, 50 kHz photodetector output voltage.

Figure 38:
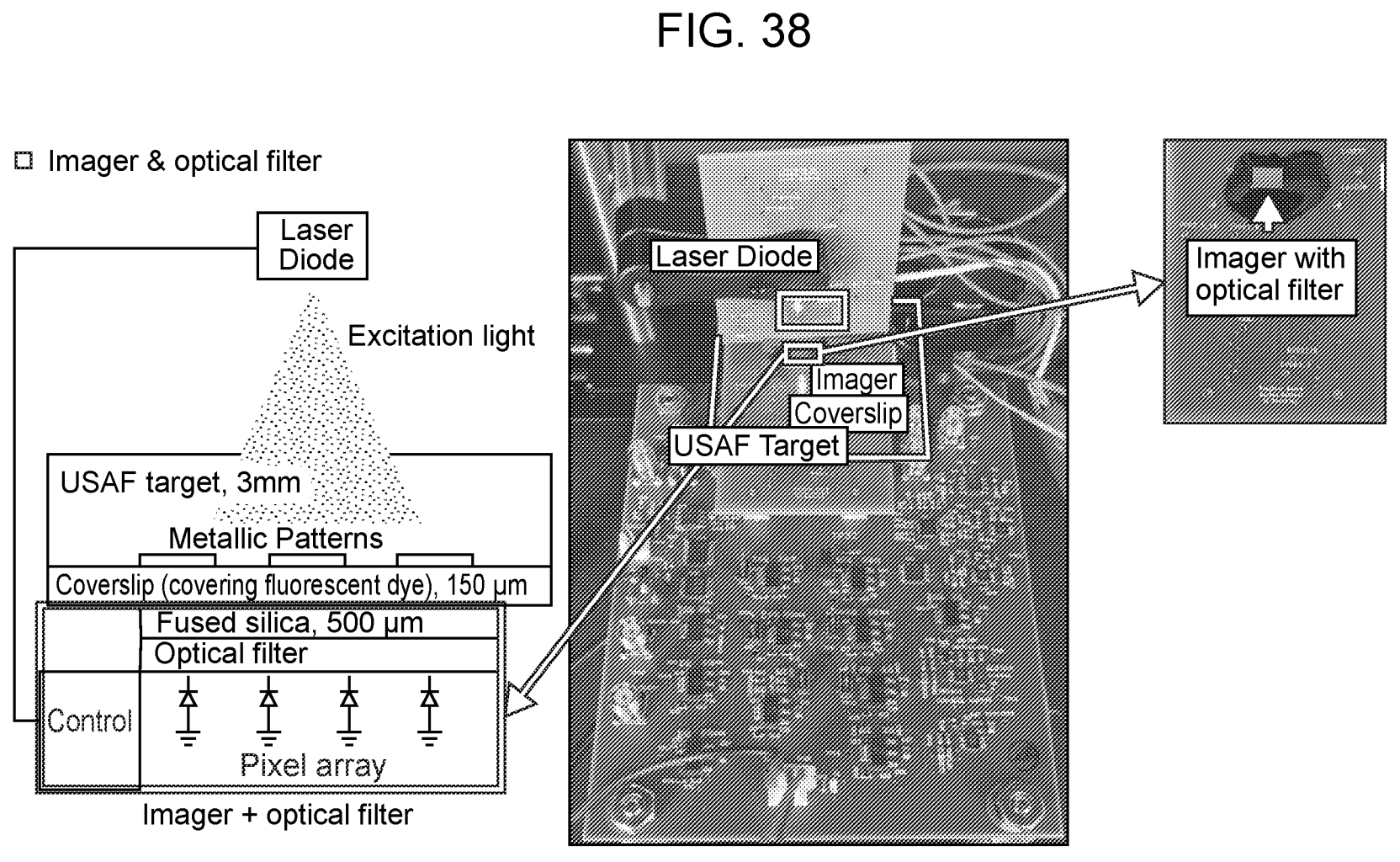

FIG. 38. Imager with optical filter. An optical filter deposited on fused silica covers the imager to reject band light from the excitation source and the background.

Figure 39:
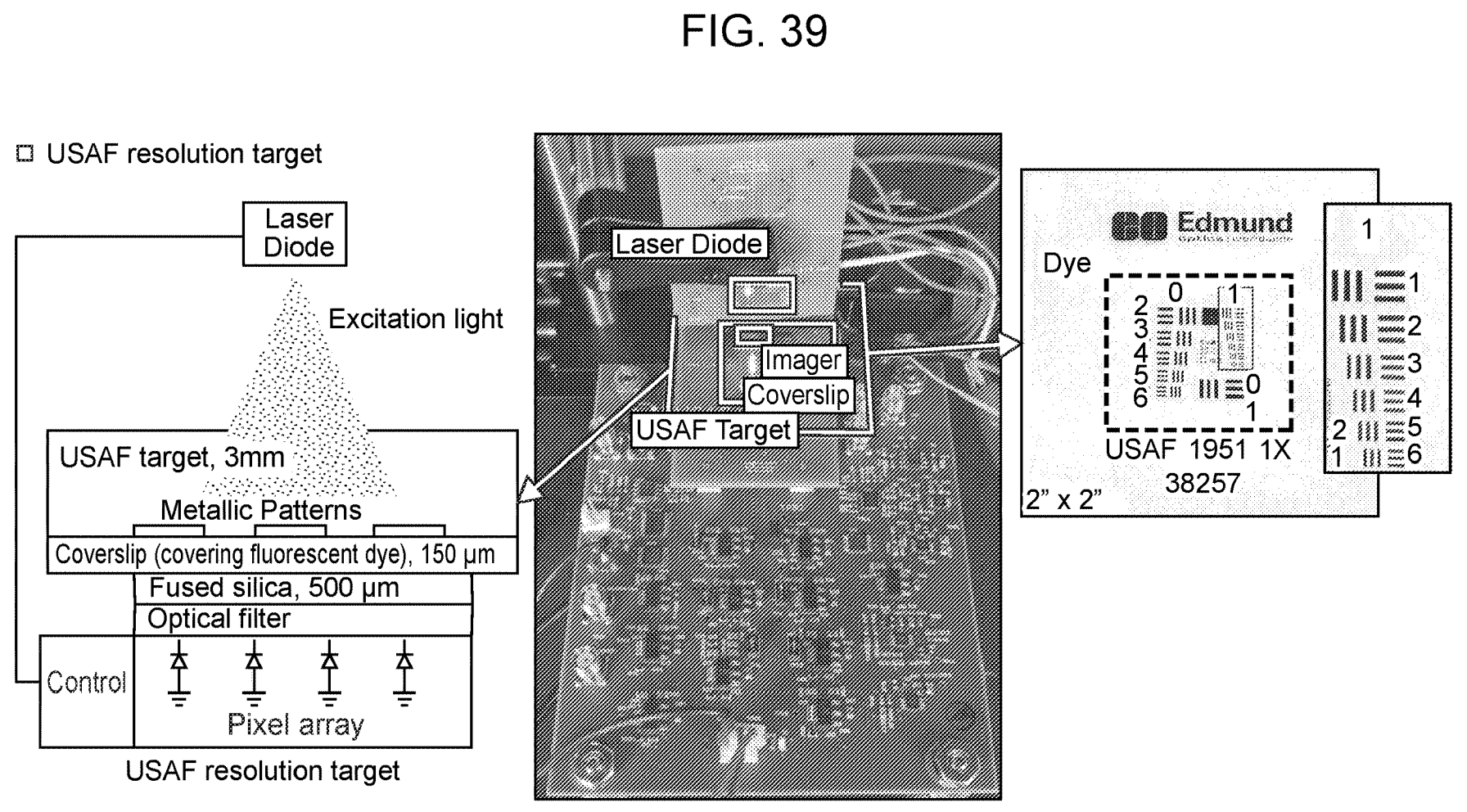

FIG. 39. USAF resolution target. A coverslip contains the cyanin-5.5 dye and is placed in contact with the USAF resolution target. The region of interest is magnified on the target on the right.

FIG. 40. Laser diode. The sub-mm sized laser diode is bonded to the board and is controlled from the imager chip. The resulting images and the corresponding areas are marked on the target. Each frame is captured after a 20s charge-up period with a 64 ms illumination interval and a 400 ms data communication state.

(FIG. 42A) Conceptual system diagram of the implant (FIG. 42B) fluorescence microscopy for fluorescently labeled cells.

FIG. 43A-43B. A schematic (FIG. 43A) and timing diagram of the ASIC (FIG. 43B).

(FIG. 44A) State transition diagram and detailed ADC and Backscatter state transition per pixel (FIG. 44B) P-I-V characterization of the laser diode (FIG. 44C) Optical power variation for repeated measurements.

FIG. 47. Comparison table.

DETAILED DESCRIPTION OF THE INVENTION

Figure 1:
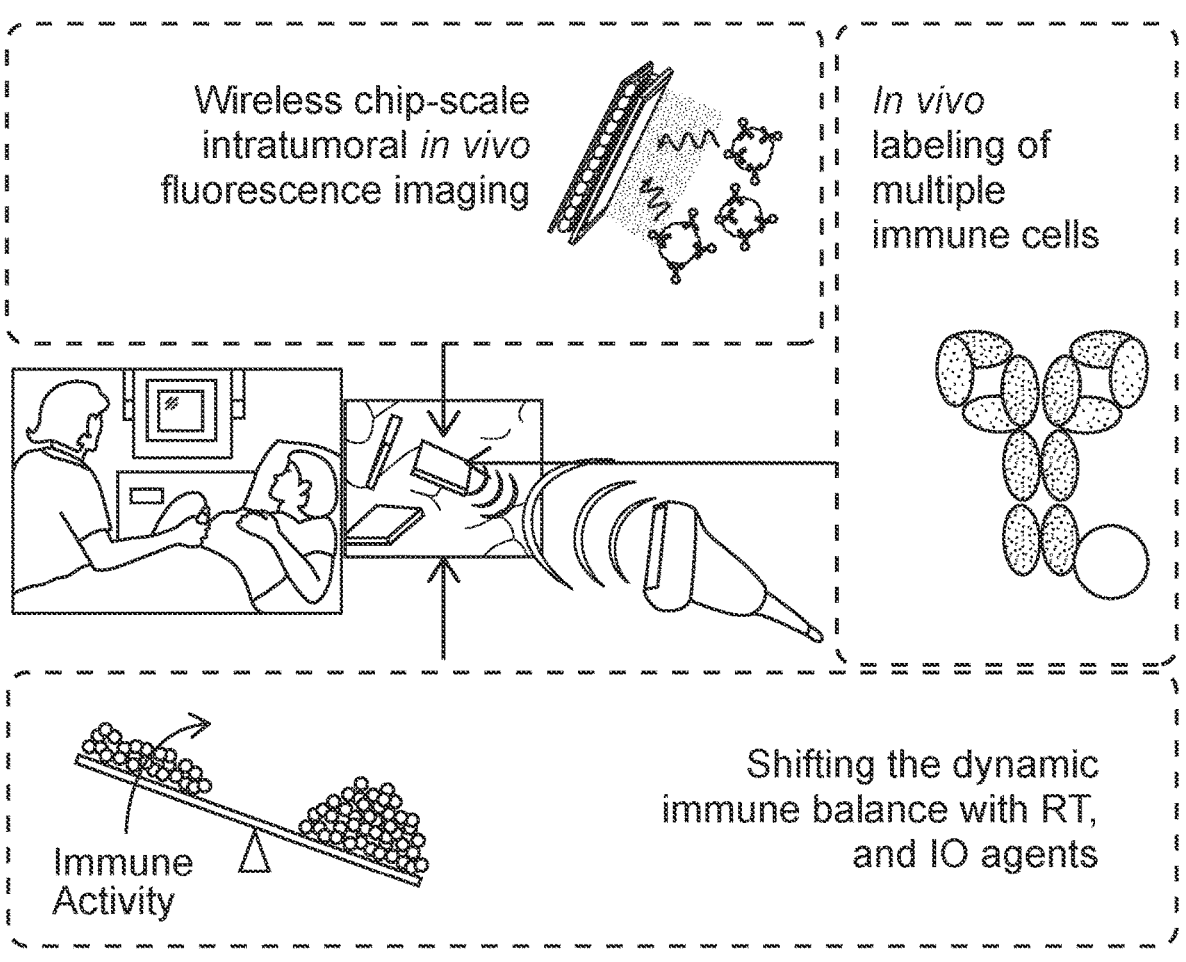
FIG. 1. Implantable Nanophotonic Sensors for Immunoresponse in the Tumor microenvironment (INSITE) Overview: "Smart fiducials" perform multi-color fluorescence imaging, which are implanted into the tumor, wirelessly communicating real-time findings.

Devices, systems, and methods are provided for in vivo fluorescence imaging. Disclosed herein is an implantable miniature fluorescence imager on a chip having a custom imaging array with microcollimators, fiber optics, or angle selective gratings for image deblurring, and optical filters that can be tuned to image fluorescence from multiple fluorophores simultaneously. Power is supplied by an on-chip power source or transmitted to the chip from an external transducer. Wireless communication may be provided by electromagnetic (e.g., radiofrequency, microwave, or infrared carrier wave) or ultrasound links to the device. The function of a fluorescence microscope is provided in a millimeter-scale device that can be readily implanted in tissue and used to image fluorescently labeled cells in vivo. The small size of the fluorescence imager makes possible sustained in vivo imaging with real-time monitoring of multiple cell types within diseased tissue or a tumor.

Before the present devices, systems, and methods are described, it is to be understood that this invention is not limited to particular methods or compositions described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the fluorophore" includes reference to one or more fluorophores and equivalents thereof, e.g. fluorescent dyes, fluorescent labels, and the like, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "about", particularly in reference to a given quantity, is meant to encompass deviations of plus or minus five percent.

The terms "peptide", "oligopeptide", "polypeptide", and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymers. Both full-length proteins and fragments thereof are encompassed by the definition. The terms also include post-expression modifications of the polypeptide, for example, phosphorylation, glycosylation, acetylation, hydroxylation, oxidation, and the like as well as chemically or biochemically modified or derivatized amino acids and polypeptides having modified peptide backbones. The terms also include fusion proteins, including, but not limited to, fusion proteins with a heterologous amino acid sequence, fusions with heterologous and homologous leader sequences, with or without N-terminal methionine residues; immunologically tagged proteins; and the like. The terms include polypeptides including one or more of a fatty acid moiety, a lipid moiety, a sugar moiety, and a carbohydrate moiety.

By "isolated" is meant, when referring to a protein, polypeptide, or peptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

"Substantially purified" generally refers to isolation of a substance (compound, protein, nucleic acid, nanoparticles) such that the substance comprises the majority percent of the sample in which it resides. Typically in a sample, a substantially purified component comprises 50%, preferably 80%-85%, more preferably 90-95% of the sample. Techniques for purifying substances of interest are well-known in the art and include, for example, ion-exchange chromatography, affinity chromatography and sedimentation according to density.

The terms "tumor," "cancer" and "neoplasia" are used interchangeably and refer to a cell or population of cells whose growth, proliferation or survival is greater than growth, proliferation or survival of a normal counterpart cell, e.g., a cell proliferative, hyperproliferative or differentiative disorder. Typically, the growth is uncontrolled. The term "malignancy" refers to invasion of nearby tissue. The term "metastasis" or a secondary, recurring or recurrent tumor, cancer or neoplasia refers to spread or dissemination of a tumor, cancer or neoplasia to other sites, locations or regions within the subject, in which the sites, locations or regions are distinct from the primary tumor or cancer.

Neoplasia, tumors, and cancers include benign, malignant, metastatic and non-metastatic types, and include any stage (I, II, Ill, IV or V) or grade (G1, G2, G3, etc.) of neoplasia, tumor, or cancer, or a neoplasia, tumor, cancer or metastasis that is progressing, worsening, stabilized or in remission. In particular, the terms "tumor," "cancer" and "neoplasia" include carcinomas, such as squamous cell carcinoma, adenocarcinoma, adenosquamous carcinoma, anaplastic carcinoma, large cell carcinoma, and small cell carcinoma, and include cancers such as, but are not limited to, pancreatic cancer, lung cancer (non-small cell lung cancer, small cell lung cancer), gastric cancer, ovarian cancer, endometrial cancer, colorectal cancer, oral cancer, skin cancer, cholangiocarcinoma, head and neck cancer, breast cancer, ovarian cancer, melanoma, peripheral neuroma, glioblastoma, adrenocortical carcinoma, AIDS-related lymphoma, anal cancer, bladder cancer, meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, malignant mesothelioma, medulloblastoma, Merkel cell carcinoma, metastatic squamous neck cell carcinoma, multiple myeloma and other plasma cell neoplasms, mycosis fungoides and the Sezary syndrome, myelodysplastic syndromes, nasopharyngeal cancer, neuroblastoma, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilm's tumor and other childhood kidney tumors.

A "ligand" or "binding agent" is any molecule that can be used to target a fluorophore to a cell or other target. In certain embodiments, the ligand is a molecule that selectively binds to a target analyte of interest (e.g., cellular marker) with high binding affinity. By high binding affinity is meant a binding affinity of at least about $10^{-4}$ M, usually at least about $10^{-6}$ M or higher, e.g., $10^{-9}$ M or higher. The ligand may be any of a variety of different types of molecules, as long as it exhibits the requisite binding affinity for the target analyte when conjugated to a fluorophore. In certain embodiments, the ligand has medium or even low affinity for its target analyte, e.g., less than about $10^{-4}$ M. As such, the ligand may be a small molecule or large molecule ligand. By small molecule ligand is meant a ligand having a size of less than 10,000 daltons, usually ranging in size from about 50 to about 5,000 daltons, and more usually from about 100 to about 1000 daltons in molecular weight. By large molecule is meant a ligand having a size of more than 10,000 daltons in molecular weight.

A small molecule ligand may be any molecule, as well as binding portion or fragment thereof, that is capable of binding with the requisite affinity to the target analyte of interest (e.g., cellular marker). Generally, the small molecule is a small organic molecule that is capable of binding to the target analyte of interest. The small molecule will include one or more functional groups necessary for structural interaction with the target analyte, e.g., groups necessary for hydrophobic, hydrophilic, electrostatic or even covalent interactions. Where the target analyte is a protein, the drug moiety will include functional groups necessary for structural interaction with proteins, such as hydrogen bonding, hydrophobic-hydrophobic interactions, electrostatic interactions, etc., and will typically include at least an amine, amide, sulfhydryl, carbonyl, hydroxyl or carboxyl group, preferably at least two of the functional chemical groups. The small molecule will also comprise a region that may be modified and/or participate in conjugation to a fluorophore, without substantially adversely affecting the small molecule's ability to bind to its target analyte.

Small molecule ligands may comprise cyclical carbon or heterocyclic structures and/or aromatic or polyaromatic structures substituted with one or more of the above functional groups. Small molecule ligands may also include organic compounds comprising alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracylines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Small molecules may include structures found among biomolecules, including peptides, carbohydrates, fatty acids, vitamins, steroids, purines, pyrimidines, derivatives, structural analogs or combinations thereof.

The small molecule may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known small molecules may be subjected to directed or random chemical modifications, such as acylation, alkylation, esterification, amidification, etc. to produce structural analogs.

As such, the small molecule may be obtained from a library of naturally occurring or synthetic molecules, including a library of compounds produced through combinatorial means, i.e., a compound diversity combinatorial library. When obtained from such libraries, the small molecule employed will have demonstrated some desirable affinity for the protein target in a convenient binding affinity assay. Combinatorial libraries, as well as methods for the production and screening, are known in the art and described in: U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

Small molecule ligands may also include known drugs that selectively bind to receptors on cells, including, without limitation, growth factor receptors, receptor tyrosine kinases, receptor protein serine/threonine kinases, G-protein coupled receptors, cytokine receptors, lectin receptors, and folate receptors. For example, anti-cancer drugs that bind to such cellular receptors may be used as ligands to target fluorophores to cancer cells. Exemplary drugs that may be used as ligands to target cancer cells include, without limitation, Acitinib, Afatinib, Axitinib, Erlotinib, Cabozantinib, Crizotinib, Gefitinib, Imatinib, Ibrutinib, Lapatinib, Neovastat, Nilotinib, Pazopanib, Perifosine, Ponatinib, Regorafenib, Sorafenib, Sunitinib, Trametinib, and Vandetenib.

As pointed out, the ligand can also be a large molecule. Of particular interest as large molecule ligands are antibodies, as well as binding fragments and mimetics thereof. Also suitable for use as binding agents are peptoids and aptamers. The ligand or binding agent may include a domain or moiety that can be covalently attached to a fluorophore without substantially abolishing the binding affinity for its target analyte (e.g., cellular marker).

The term "antibody" encompasses monoclonal antibodies as well as hybrid antibodies, altered antibodies, chimeric antibodies, and humanized antibodies. The term antibody includes: hybrid (chimeric) antibody molecules (see, for example, Winter et al. (1991) *Nature* 349:293-299; and U.S. Pat. No. 4,816,567); F(ab')₂ and F(ab) fragments; Fᵥ molecules (noncovalent heterodimers, see, for example, Inbar et al. (1972) *Proc Natl Acad Sci USA* 69:2659-2662; and Ehrlich et al. (1980) *Biochem* 19:4091-4096); single-chain Fv molecules (scFv) (see, e.g., Huston et al. (1988) *Proc Natl Acad Sci USA* 85:5879-5883); nanobodies or single-domain antibodies (sdAb) (see, e.g., Wang et al. (2016) *Int J Nanomedicine* 11:3287-3303, Vincke et al. (2012) *Methods Mol Biol* 911:15-26; dimeric and trimeric antibody fragment constructs; minibodies (see, e.g., Pack et al. (1992) *Biochem* 31:1579-1584; Cumber et al. (1992) *J Immunology* 149B:120-126); diabodies, tetrabodies, affibodies, camelid antibodies, humanized antibody molecules (see, e.g., Riechmann et al. (1988) *Nature* 332:323-327; Verhoeyan et al. (1988) *Science* 239:1534-1536; and U.K. Patent Publication No. GB 2,276,169, published 21 Sep. 1994); and, any functional fragments obtained from such molecules, wherein such fragments retain specific-binding properties of the parent antibody molecule.

"Fv" is an antibody fragment which contains an antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although often at a lower affinity than the entire binding site.

"Single-chain Fv" or "scFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv see, for example, Pluckthun, A. in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) on the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Holliger et al., (1993) Proc. Natl. Acad. Sci. USA, 90: 6444-6448.

The term "affibody molecule" refers to a molecule that consists of three alpha helices with 58 amino acids and has a molar mass of about 6 kDa. A monoclonal antibody, for comparison, is 150 kDa, and a single-domain antibody, the smallest type of antigen-binding antibody fragment, 12-15 kDa. See, for exemplary details of affibody structures and uses, Orlova, A; Magnusson, M; Eriksson, T L; Nilsson, M; Larsson, B; Hoiden-Guthenberg, I; Widstrom, C; Carlsson, J et al. (2006). "Tumor imaging using a picomolar affinity HER2 binding affibody molecule", Cancer Res. 66 (8): 4339-48. Exemplary Affibody. Molecules are commercially available from Abcam Corp. Cambridge Mass.

The phrase "specifically (or selectively) binds" with reference to binding of an antibody or other binding agent to an antigen or analyte (e.g., cellular marker such as a tumor-marker or immune activation marker) refers to a binding reaction that is determinative of the presence of the antigen or analyte in a heterogeneous population of proteins and other biologics. Thus, under designated assay conditions, the specified antibodies or other binding agents bind to a particular antigen or analyte at at least two times the background and do not substantially bind in a significant amount to other molecules present in the sample. Specific binding to an antigen or analyte under such conditions may require an antibody or other binding agent that is selected for its specificity for a particular antigen or analyte. For example, antibodies raised to an antigen from specific species such as rat, mouse, or human can be selected to obtain only those antibodies that are specifically immunoreactive with the antigen and not with other proteins, except for polymorphic variants and alleles. This selection may be achieved by subtracting out antibodies that cross-react with molecules from other species. A variety of immunoassay formats may be used to select antibodies specifically immunoreactive with a particular antigen. For example, solid-phase ELISA immunoassays are routinely used to select antibodies specifically immunoreactive with a protein (see, e.g., Harlow & Lane. Antibodies, A Laboratory Manual (1988), for a description of immunoassay formats and conditions that can be used to determine specific immunoreactivity). Typically, a specific or selective reaction will be at least twice background signal or noise and more typically more than 10 to 100 times background.

The term "conjugated" refers to the joining by covalent or noncovalent means of two compounds or agents (e.g., binding agent specific for a tumor marker or immune activation marker conjugated to a fluorophore).

The terms "subject", "individual" or "patient" are used interchangeably herein and refer to a vertebrate, preferably a mammal. By "vertebrate" is meant any member of the subphylum Chordata, including, without limitation, humans and other primates, including nonhuman primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

Miniature Fluorescence Imager on a Chip

An implantable millimeter-scale fluorescence imager on a chip is provided herein. Miniaturization of the fluorescence imager is achieved, in part, by eliminating conventional optics, which is made possible because the fluorescence imager is placed directly in tissue. The micron to millimeter-proximity of the fluorescence imager to cells allow capture of light before it diverges—preserving spatial resolution and increasing sensitivity. Therefore, difficult to miniaturize lenses are not needed.

The fluorescent imager has a custom imaging array with angle-selective structures such as angle selective gratings or microcollimators for image deblurring, and optical filters that can be tuned to image fluorescence from multiple fluorophores simultaneously. Power is supplied by an on-chip power source or transmitted to the chip from an external transducer such as, but not limited to, an ultrasound transducer, an electromagnetic (EM) transducer, an inductive transducer, or a radiofrequency (RF) transducer. For example, an ultrasound transducer can be used to supply power wirelessly to the imager through a piezoelectric substrate (e.g., piezoelectric crystal or ceramic) incorporated into the integrated circuit. Alternatively, the imager may further comprise an on-chip antennae configured to receive radiofrequency (RF) power from an external RF transducer or electromagnetic power from an EM or inductive transducer. Power supplied by an external transducer can be used to power the chip operation directly or stored in a capacitor for later use. In some embodiments, power from an external transducer is used to charge a rechargeable on-chip battery, which can be used to power chip operations. Data can be wirelessly transmitted or stored and then transmitted.

The imaging array comprises a plurality of photodiodes arrayed on the surface of the chip, wherein each photodiode is coated with a layer of material (or multiple materials) that functions as an optical filter (e.g., an absorption filter or an interference filter). In certain embodiments, multiple layers of filter material are used in combination with micro-collimators to block illumination light and allow fluorescence light to pass through to the imager chip.

In certain embodiments, the optical filter comprises an absorption filter having a band gap and thickness suitable to allow light at a fluorescence emission wavelength of a fluorophore of interest to pass through to the photodiode. Exemplary absorption filter materials include, without limitation, amorphous silicon, crystalline silicon, gallium phosphide, cadmium selenide, gallium arsenide, and indium phosphide. Different fluorophores with different emission spectra (colors) can be imaged by using absorption filter materials with different band gaps in the imaging array. In addition, the absorption filters in the imaging array can be tuned by varying the thickness of the layer of absorption filter material on individual photodiodes. In certain embodiments, the band gap and/or thickness of the layer of absorption filter material is varied on the plurality of photodiodes to allow selection of light at different fluorescence emission wavelengths to allow fluorescence imaging with the imaging array of multiple fluorophores having different fluorescence emission spectra. In some embodiments, the thickness of the layer of absorption filter material on at least two photodiodes is different. In other embodiments, the thickness of the layer of absorption filter material on all the photodiodes is the same.

In certain embodiments, the thickness of the layer of absorption filter material on a photodiode is less than 100 microns. For example, the thickness of the layer of absorption filter material may range from 1 micron to 100 microns, including any thickness within this range, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, or 100 microns in thickness. In some embodiments, the thickness of the layer of absorption filter material ranges from about 5 microns to about 30 microns In certain embodiments, the optical filter is an interference filter. In some embodiments, the interference filter is a single bandpass, dual bandpass, triple bandpass, or quadruple bandpass interference filter. In some embodiments, the interference filter further comprises a layer of absorption filter material on top of the interference filter or underneath the interference filter.

In certain embodiments, the interference filter further comprises one or more layers of material comprising a plurality of angle selective gratings, collimators, or fiber optic plates that block light that is not incident within 30° of an axis perpendicular to the plane of the chip. In some embodiments, fiber optic plates are used that block light that is not incident within 6° of an axis perpendicular to the plane of the chip (e.g., having a FWHM of 12 degrees). In some embodiments, angle selective gratings are used that block light that is not incident within 15° of an axis perpendicular to the plane of the chip.

In some embodiments, the one or more layers of material comprising the plurality of angle selective gratings, collimators, or fiber optics is on top of the layer of filter material (between the filter and cells), underneath the layer of filter material (between the filter and photodiodes), or both on top and underneath the layer of filter material. In some embodiments, the angle selective gratings, collimators, or fiber optic plate are in a layer of material on top of the layer of filter material and block light that is not incident within 10°-15° of an axis perpendicular to the plane of the chip. In some embodiments, this layer on top of the layer of filter material has a thickness of about 100 microns to about 500 microns. In some embodiments, the angle selective gratings, collimators, or fiber optics are in a layer of material underneath the layer of filter material and block light that is not incident within 5°-30° of an axis perpendicular to the plane of the chip. In some embodiments, this layer underneath the layer of filter material has a thickness of about 8 microns or less. Surrounding the collimators or fiber optics may be a material that is opaque to the incident light such that only light passing through the collimators or fiber optics may pass through the filter. This ensures proper operation of interference-based filters which have an angle-dependent response, and whose performance decays with oblique angles of incidence. In certain embodiments, the interference filter may be deposited on either one or both surfaces of the fiber optic plate or directly on the imager chip. The interference filter may have any of the following filter characteristics: long-pass, short-pass, notch, bandpass, or a combination of any number of these characteristics.

Figure 20:
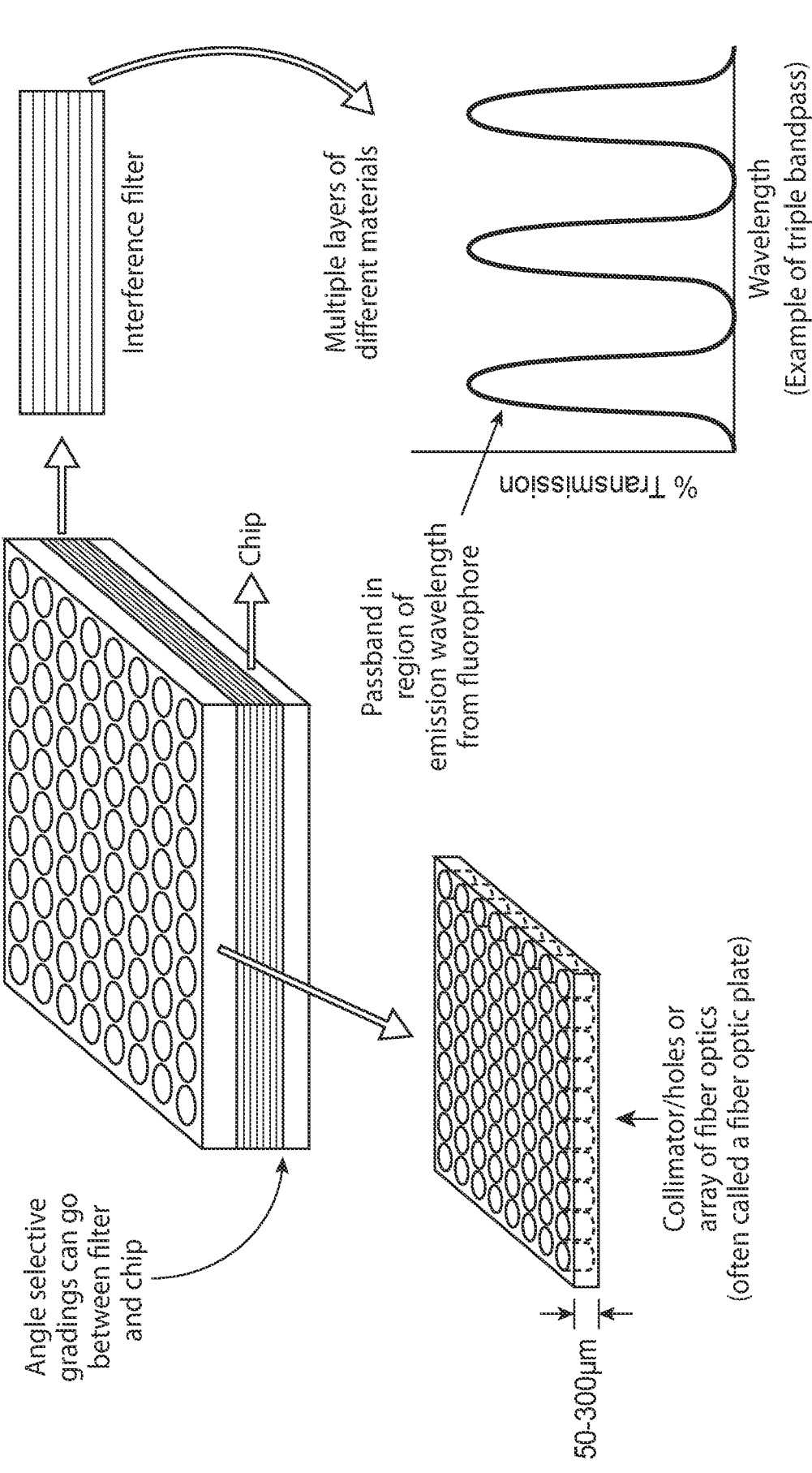
FIG. 20. Schematic of a chip-based fluorescence imager illustrating a fiber optic collimator approach.

In some embodiments, the optical filter comprises an interference filter with an array of micro-collimators (or micro-channels) affixed to the "top" surface (between the filter and cells), or the "bottom" surface (between the filter and photodiodes), or both (see, e.g., FIG. 19). The purpose of the layer of collimators is to eliminate light incident at oblique ("off-axis" or non-perpendicular) angles, that may bleed through the interference filter. The collimator array blocks light at oblique angles (for example >30 degrees of the perpendicular axis) while allowing light that is incident perpendicularly (for example from 0-10 degrees) to pass through. The microcollimators can be made of transparent material separated by a cladding or material that is either opaque, or of a higher index of refraction such that light is trapped in the collimator and the critical angle is less than 30 degrees. Light >30 degrees can be extinguished by at least 1, 2, 3, 4, 5, or 6 orders of magnitude relative to light entering at <10 degrees). Alternatively, a fiber optic array or fiber optic plate (see, e.g., FIG. 20) can be used on top of the interference filter layer to reject fluorescent light emitted incident at oblique/off perpendicular angles that will not be adequately rejected by the filter—since it has an angle dependent response. In addition, angle selective gratings can be placed between the filter and the imaging chip. An additional layer of absorption filter can be affixed either on top of the filter or underneath the filter to absorb any illumination light that may penetrate through the interference filters when light incidence is off axis. The interference filter may include, without limitation, a single bandpass, dual bandpass, triple bandpass, or quadruple bandpass filter to allow for multicolor imaging of tissue using the same image sensor.

The fluorescence imager further comprises a plurality of light emitting sources, which may be located on the chip or externally (e.g., implanted in tissue in proximity to the imager). The light emitting sources can include, without limitation, micro-laser diodes or light-emitting diodes (LEDs). LEDs may be used with emission filters. Alternatively, LEDs having a tight enough full-width half maximum spread can be used without emission filters. The light sources may emit light of a single color (wavelength) or multiple colors (wavelengths) so as to illuminate multiple fluorophores. Multiple light sources of the same and/or different wavelength emissions may be arrayed on chip, and used in parallel or serially to illuminate the tissue. In some embodiments, an external light emitting source is on a separate chip that is implantable in tissue. The internal and/or external light sources can be activated together or sequentially.

Figure 11:
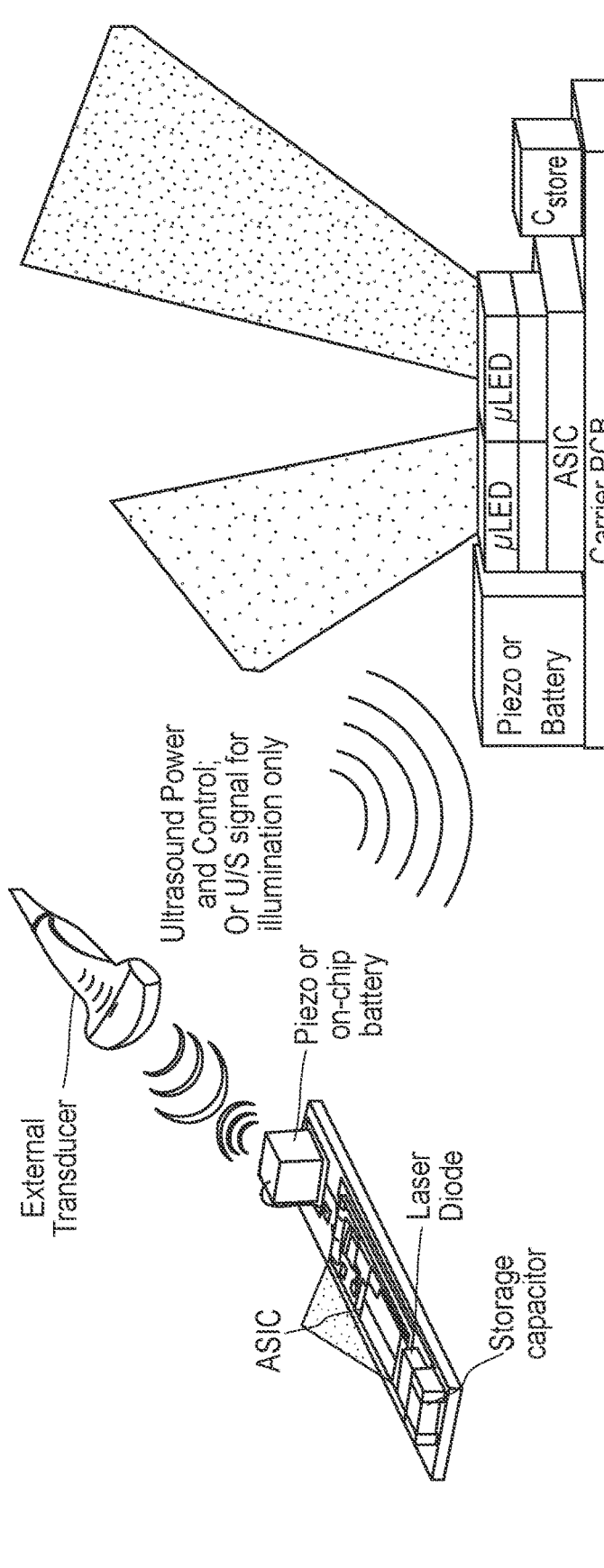
FIG. 11. Implantable imaging constellation with an external ultrasound transducer.
Figure 12:
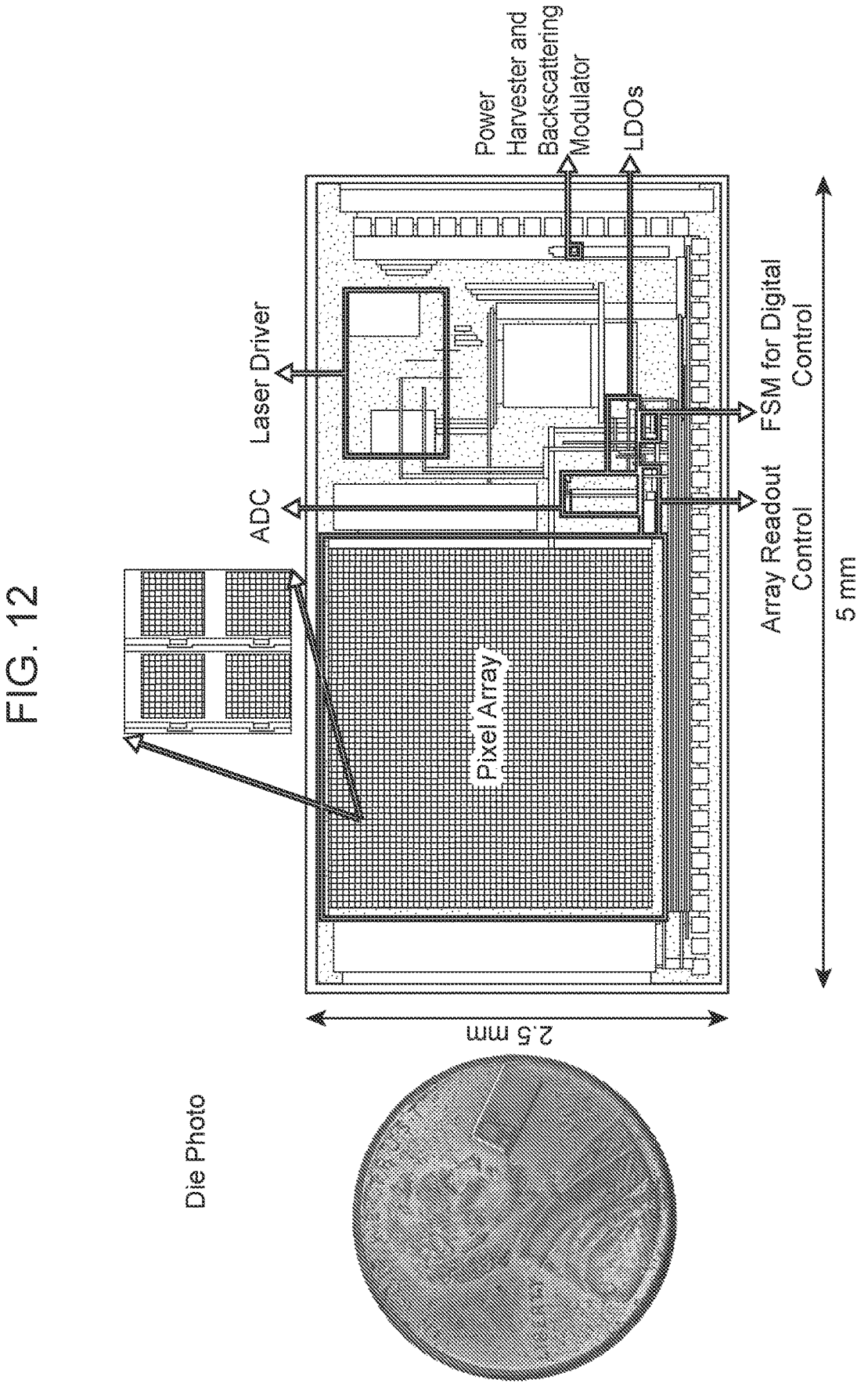
FIG. 12. Prototype of chip-based fluorescence imager. The fluorescence imager is miniaturized having dimensions of 5 mm in length and 2.5 mm in width. A penny with the prototype on top of it is shown to provide a sense of scale.
Figure 13:
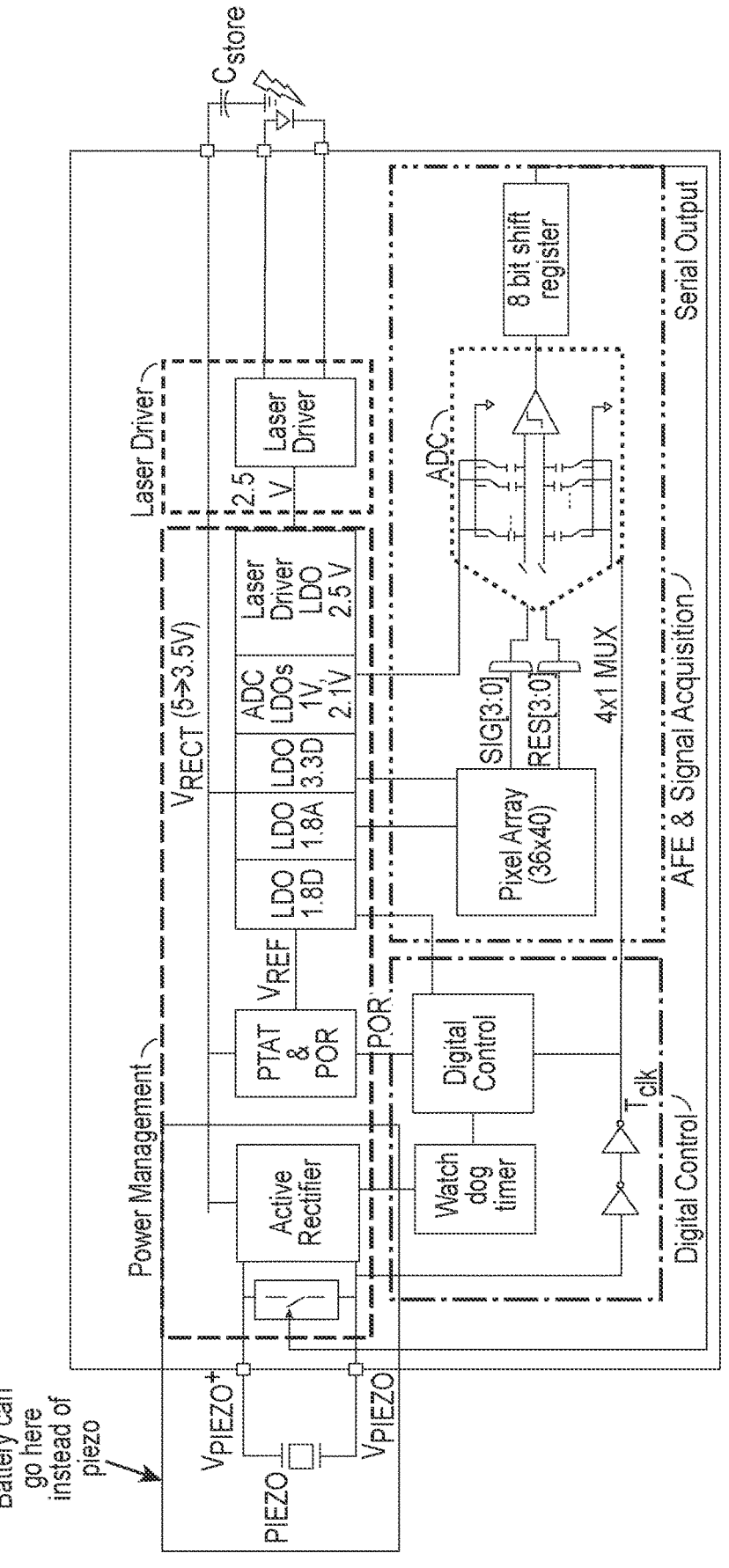
FIG. 13. Block diagram of the circuitry for the fluorescence imager.
Figure 14:
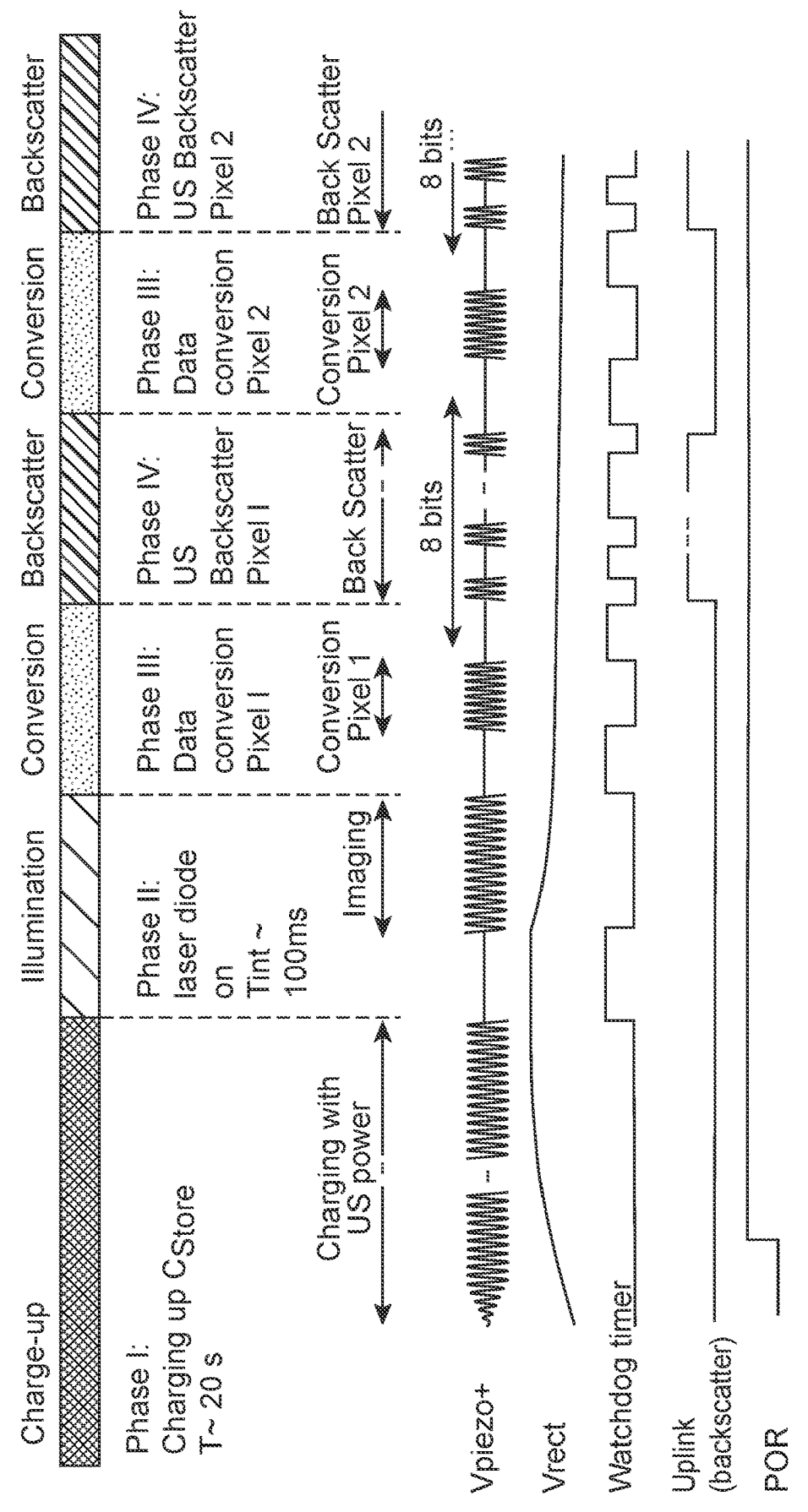
FIG. 14. Timing diagram, including timing for charge-up, illumination, data conversion, and backscattering modulation.
Figure 15:
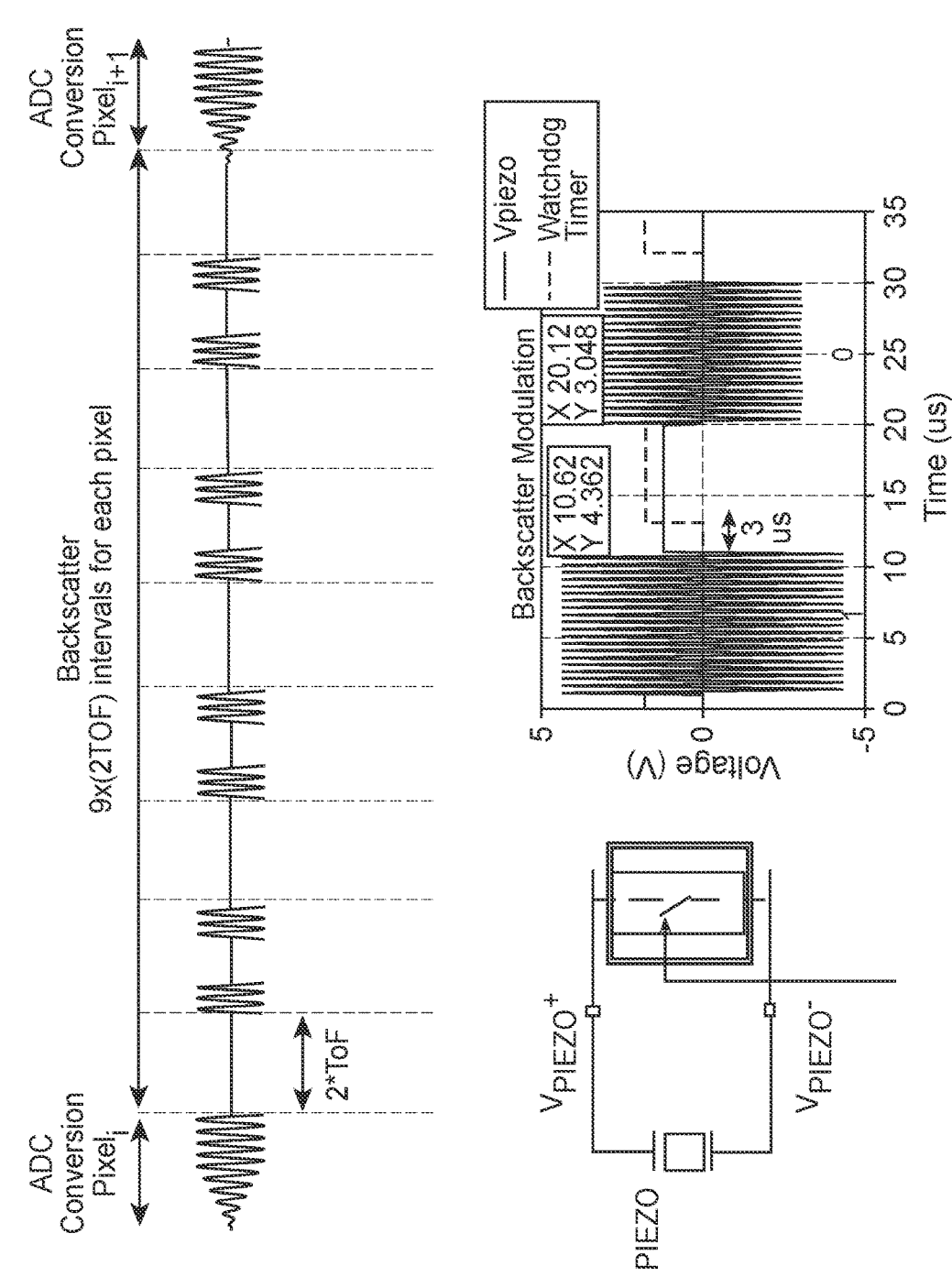
FIG. 15. Backscattering modulation using an analog-to-digital converter (ADC).
Figure 16:
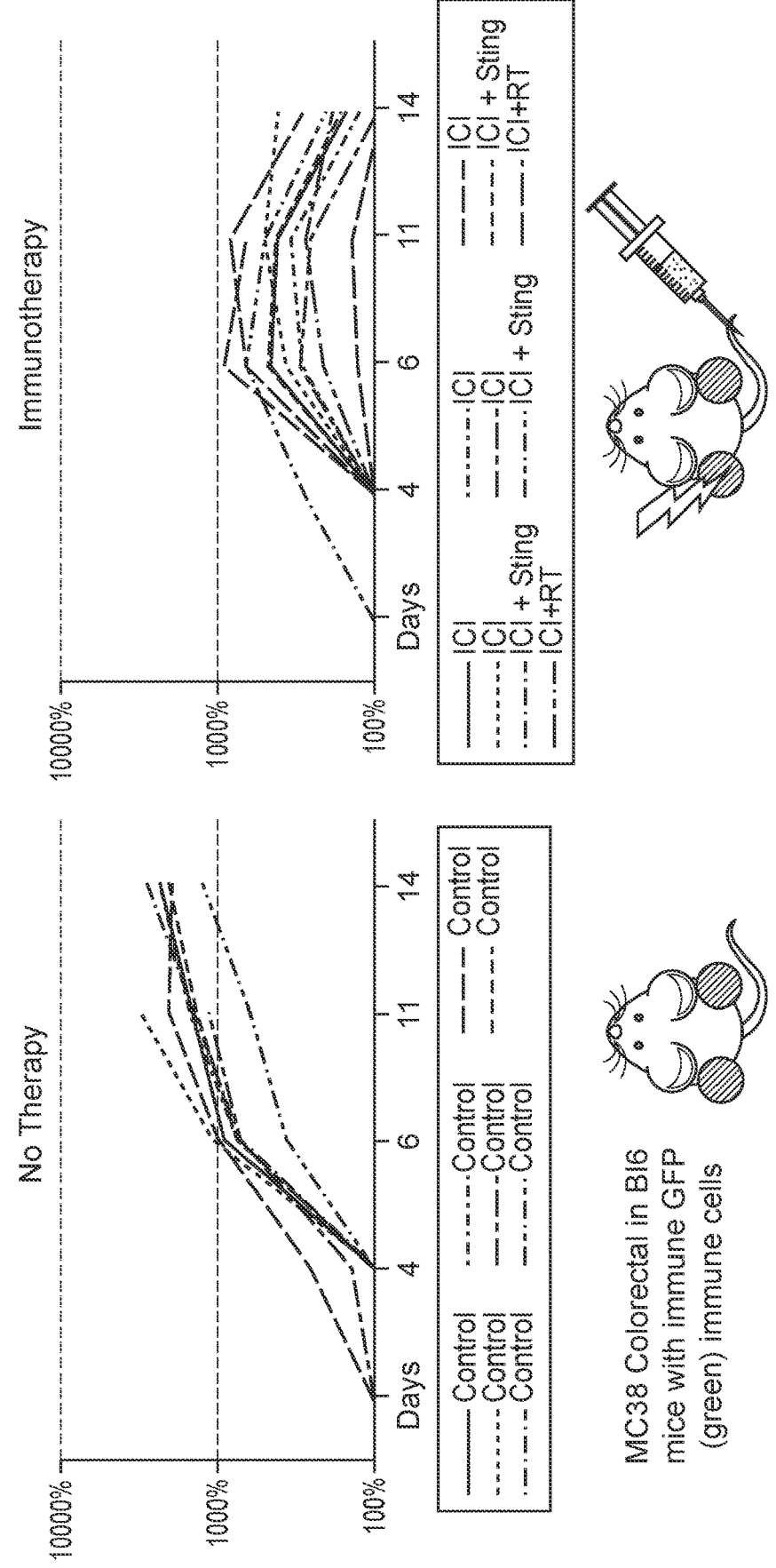
FIG. 16. Use of the chip-based fluorescence imager to determine early kinetics of an immune response to a tumor using an imaging biomarker in a mouse model. A MC38 colorectal tumor in BI6 mice was imaged with GFP-labeled (green) immune cells.
Figure 17:
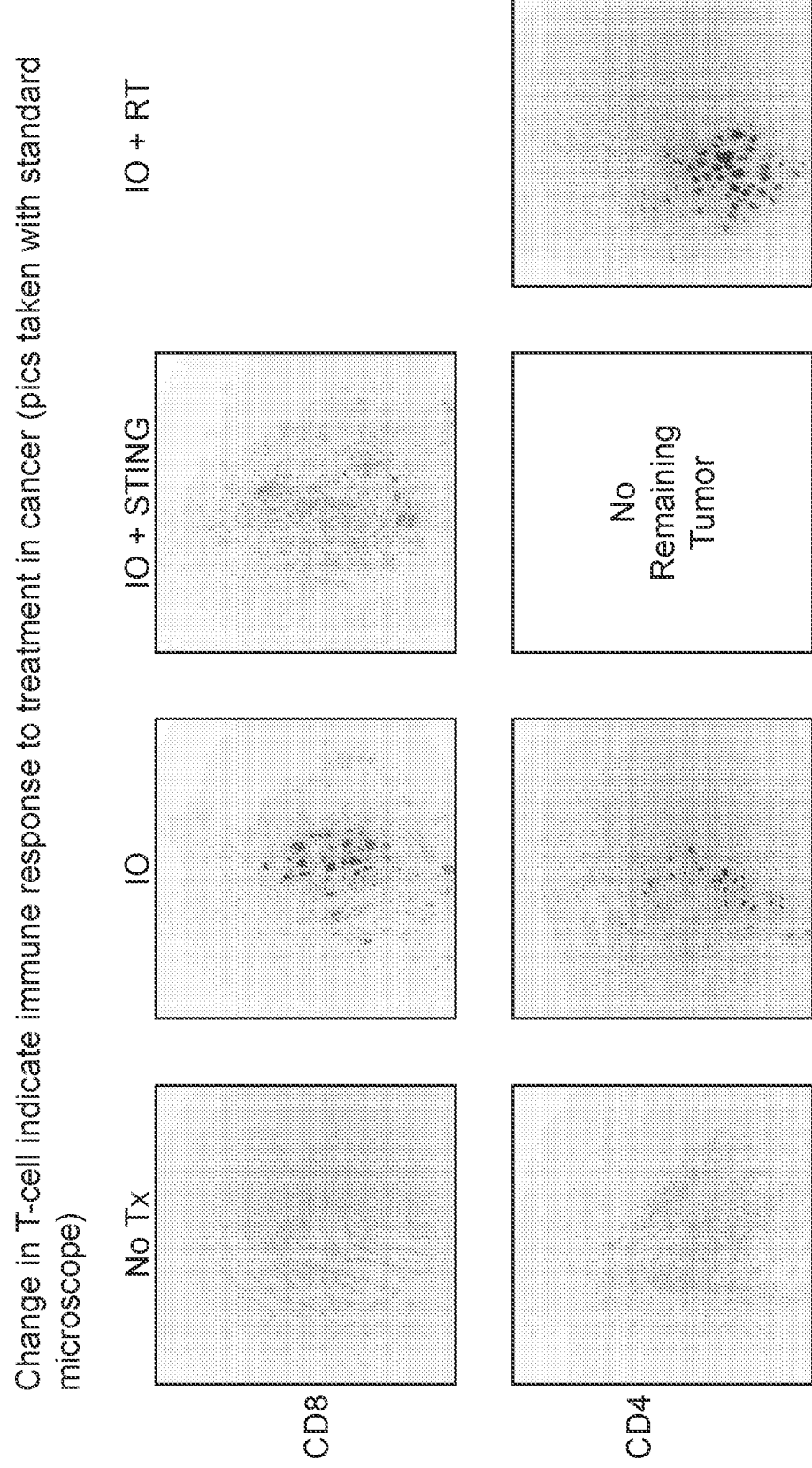
FIG. 17. Mouse Models—T-Cell Infiltration. Change in T-cells indicate an immune response to treatment in cancer.

In certain embodiments, a plurality of light emitting sources are located externally. In some embodiments, the external light emitting source is on a separate chip that is implantable in tissue. For example, a "micro-star" external light source can be used to illuminate tissue (see FIG. 11). A micro-star comprises a chip similar to that used for a fluorescence imager except that the chip does not have an imaging array with photodiodes and does not transmit imaging data. The primary purpose of a micro-star is to illuminate tissue. The micro-star chip may comprise, for example, a single wavelength, laser diode; two laser diodes of different wavelengths; three laser diodes of different wavelengths; etc. Alternatively, the micro-star chip may comprise one or more LEDs instead of laser diodes. LEDs tend to be more power efficient than laser diodes, but have a broader wavelength spread. Therefore, emission filters may be used with the LEDs to prevent wavelengths of light from being in the passband of the corresponding optical filter. The wavelength of the light emitted from each laser diode or LED should overlap the excitation wavelength of an intended fluorophore and not overlap with the emission wavelengths of simultaneously imaged fluorophores or fall into the any of the emission pass bands of the filter. The same arrangement of LEDs or laser diodes that is used on a micro-star can also be incorporated onto a corresponding fluorescence imager chip. Similarly to the fluorescence imager, power can be supplied to the micro-star by an on-chip power source or transmitted to the chip from an external transducer. In some embodiments, the micro-star chip comprises an on chip-energy storage device (e.g., battery or capacitor) to supply power for operation of one or more light-emitting sources on the chip. An on-chip driver circuit will provide power to the light-emitting sources. (Alternatively the driver circuit may be located off chip.) This driver may be capable of supplying a wide range of bias currents, may be tolerant of a wide range of required on voltages of the light sources, and can be configurable to the each of the above ends. The micro-star chip may further comprise a piezoelectric substrate (e.g., piezoelectric crystal or ceramic) incorporated into the integrated circuit to receive power from an external transducer, such as an ultrasound transducer. In some embodiments, the same ultrasound transducer that is used to supply power wirelessly to the fluorescence imager is used to supply power to the micro-star to turn on the light emitting sources on the micro-star to provide illumination. In some embodiments the platform comprises a network of sensors comprising multiple fluorescence imagers integrated with light emitting sources, and multiple independent light sources (e.g., micro-stars). Each mote is powered by an on chip-energy storage device: either a battery or energy storing capacitor which is charged up from an external power source (such as ultrasound transducer or RF transducer). In the case of ultrasound power transfer, an ultrasound transducer is used to supply power wirelessly through a piezoelectric crystal/ceramic incorporated into the integrated circuits of the imager and/or micro-stars.

In certain embodiments, the fluorescence imager comprises an on-chip power source or energy storage device such as a capacitor or battery (for example measuring <5 mm$^3$) to supply power for operation of the fluorescence imager. The on-chip power source or energy storage device can include, without limitation, lithium ion batteries, silver oxide batteries, or chip-type electric double layer capacitors. In one embodiment, the battery has dimensions of 3.6 mm×5.5 mm×1 mm with an energy capacity of 300 μA hours. In some embodiments, the battery is rechargeable. In some embodiments, a battery and a capacitor are used to store the levels of power needed to operate the chip.

In other embodiments, the on-chip power source comprises radionuclides, from which power is harvested directly or indirectly. For example, power can be harvested from radionuclides through direct interaction of emitted radionuclides with on-chip diodes, or indirectly through conversion of emitted radionuclide particles (such as an electron or alpha particle) to light via a scintillating material, and then captured by a photovoltaic. The power derived from the radionuclides can be used to charge a battery or capacitor, or power the system directly. In some embodiments, the fluorescence imager comprises an on-chip photovoltaic system or a nuclear battery or a radionuclide in combination with a scintillator and photovoltaic energy harvester to provide power to the fluorescence imager chip.

In some embodiments, power is transmitted to the chip from an external transducer such as, but not limited to, an ultrasound transducer, an electromagnetic (EM) transducer, an inductive transducer, or a radiofrequency (RF) transducer.

In some embodiments, the fluorescence imager further comprises a piezoelectric substrate that generates piezoelectricity in response to exposure to ultrasound from an external ultrasound transducer. Any suitable piezoelectric crystal or ceramic may be used in the imager. Exemplary piezoelectric crystals include, without limitation, langasite ($La_3Ga_5SiO_{14}$), gallium orthophosphate ($GaPO_4$), lithium niobate (LiNbO$_3$), lithium tantalate (LiTaO$_3$), quartz, berlinite (AlPO$_4$), Rochelle salt, topaz, tourmaline-group minerals, and lead titanate (PbTiO$_3$). Exemplary piezoelectric ceramics include, without limitation, ceramics with perovskite, tungsten-bronze, lead zirconate titanate (Pb[Zr$_x$T$_{1-x}$]O$_3$, potassium niobate (KNbO$_3$), sodium tungstate (Na$_2$WO$_3$), Ba$_2$NaNb$_5$O$_5$, Pb$_2$KNb$_5$O$_{15}$, and zinc oxide (ZnO). In certain embodiments that the piezoelectric ceramic/crystal is made of toxic material, a biocompatible layer of Parylene C is used to encapsulate the piezoceramic without impacting its power harvesting and data communication capabilities. In some embodiments the piezoelectric substrate and/or other elements such as a storage capacitor are off-chip. For example, the piezoelectric substrate and the storage capacitor may be assembled on a board containing the chip.

In some embodiments, the fluorescence imager further comprises an on-chip antenna configured to receive power from an external transducer and supply power for operation of the fluorescence imager, wherein electrical energy output from the on-chip antenna in response to receiving the power is stored in the on chip-energy storage device. In some embodiments, the antenna is configured to receive RF power from an external RF transducer and supply power for operation of the fluorescence imager, wherein electrical energy output from the on-chip antenna in response to receiving the RF power is stored in the on chip-energy storage device. In other embodiments, the antenna is configured to receive electromagnetic power inductively transferred to a coil from an external transducer.

In certain embodiments, an energy storage device such as a capacitor or a rechargeable battery is used to store electrical energy output from a piezoelectric substrate in response to receiving ultrasound power or an antenna in response to receiving RF power or electromagnetic power, wherein the capacitor or rechargeable battery supplies power to the plurality of light emitting sources and the imaging array. In certain embodiments this energy storage device is on-chip or off-chip. In some embodiments the piezoelectric substrate and/or battery or storage capacitor are assembled on a solid support (e.g., board) containing the chip. In certain embodiments, the fluorescence imager comprises a pre-charged battery, and does not receive external power or recharge. After discharging the battery remains until it is removed.

The fluorescence imager may further comprise several regulators to generate the on-chip voltages for circuit operation and on-chip clock generation. In embodiments where power is transferred from an external transducer, the fluorescence imager further comprises a voltage rectifier and several voltage regulators to generate the on-chip voltages for circuit operation. Multiple voltage sources at various levels can be generated on-chip. For example, 3.3 V, 2.5 V, 2.1 V, 1.8 V and 1 V can be generated, which can then directly power circuitry on the chip. The imager may further comprise a clock, which can be derived from the transducer signal. An analog to digital converter (ADC) can also be included on the chip. In certain embodiments the ADC is an 8-bit differential SAR ADC with a 0.5 V or 1 V maximum range. In other embodiments, the ADC is a 10-bit SAR ADC with a 0.5 V or 1 V maximum range.

In some embodiments, 4 ADCs run simultaneously to decrease the conversion time, and their digital outputs are stored in an on-chip storage unit. Storage of digital output of the ADC minimizes the effect of leakage as the pixels are being read out sequentially and transmitted according to the communication protocol. This approach won't change the overall power consumption for analog to digital conversion since the total number of pixels is the same.

In some embodiments, the in-pixel sampling switches are made of thicker oxide devices to limit the leakage current due to subthreshold conduction of the devices during hold times. Thicker oxide devices cut down the leakage current by more than 2 orders of magnitude. In other embodiments, the transient decay of the individual pixel's voltage due to leakage can be estimated and characterized by conducting a series of measurements on the same pixel at different time-points. The reconstructed transient voltage waveform for each pixel is used to estimate the initial value of the pixel voltage by extrapolation.

In some embodiments, in-pixel ADCs minimize the analog to digital conversion time for the pixel array and circumvent the leakage problem and enable expanding the size of the imager array without compromising the frame rate. Multiple ADC types or architectures can be used. One example, to maintain the fill factor of the pixels, is to use an oversampling Sigma-Delta.

In certain embodiments, the ASIC further comprises a reference voltage generator. In some embodiments, the reference voltage generator is a bandgap voltage reference generator. In some embodiments, due to the well-regulated body temperature, the on-chip reference voltage generator is proportional to absolute temperature (PTAT). In certain embodiments, the fluorescence imager further comprises a power-on-reset (POR) circuit.

In some embodiments, the fluorescence imager further comprises a data storage unit in communication with the imaging array, wherein the data storage unit stores imaging data from the imaging array. The data storage component may be of any type capable of storing information, and may utilize, e.g., FLASH memory, metal-oxide-semiconductor (MOS) memory, random-access memory (RAM), dynamic random-access memory (DRAM), static random-access memory (SRAM), synchronous dynamic random-access memory (SDRAM), or any other write-capable memory.

In some embodiments, the fluorescence imager further comprises a data processing unit in communication with the data storage unit. Image processing may include local background subtraction, whereby values from neighboring pixels are used to measure the background. Image processing may include averaging multiple sequential images to improve the signal to noise ratio within the image. The images are taken within a time span such that the cell positions do not appreciably change (for example within a few minutes). Images taken with different wavelengths of light in rapid succession can be used to (1) calibrate out non-uniformities in illumination, and (2) autofluorescence background and (3) dark current, offsets and low frequency noise processes, such as flicker noise. In some embodiments, machine learning techniques are employed in processing imaging data to improve image quality. Machine learning algorithms may also be used to automate analysis of imaging data and for classification of cells. Any suitable machine learning algorithm may be used in processing imaging data including, without limitation, convolutional neural networks (CNNs) and deep learning algorithms.

In some embodiments, the fluorescence imager further comprises an edge computing device connected to the data storage unit, wherein the edge computing device receives data from the data storage unit. An on-chip edge computing device may be programmed to partially process fluorescence imaging data, which is subsequently transmitted to an external data processing unit to complete data processing.

In certain embodiments, the fluorescence imager further comprises a first wireless communication unit in communication with the data storage unit and an external data receiving device comprising a second wireless communication unit. In some embodiments, the first wireless communication unit utilizes a wireless communication protocol using an electromagnetic carrier wave (e.g., radio wave, microwave, or infrared) or ultrasound to transfer data from the data storage unit to the external data receiving device comprising the second wireless communication unit. For example, the first wireless communication unit may utilize a radio-frequency communication protocol or an ultrasound communication protocol to transfer data from the data storage unit to the external data receiving device comprising the second wireless communication unit. The data receiving device may include, without limitation, a computer or hand-held device, such as a cell phone or tablet. In certain embodiments, the fluorescence imager periodically takes images and stores data in the data storage unit on the chip. At either set time points or upon interrogation, the stored data can be wireless transmitted from the fluorescence imager to the external data receiving device.

In certain embodiments, the fluorescence imager further comprises an analog to digital converter in communication with the data storage unit. In certain embodiments, the fluorescence imager further comprises multiple analog to digital converters which then feed data into a storage buffer or memory which is then transmitted. This data can be transmitted at the time of imaging, or stored for subsequent transmission. The data can be averaged with subsequent images taken near the same time point.

In certain embodiments, the fluorescence imager further comprises a backscattering modulator unit in communication with the imaging array. In other embodiments, active telemetry modulation schemes such as amplitude shift keying (ASK), phase shift keying (PSK), frequency shift keying (FSK), pulse width modulation amplitude shift keying (PWM-ASK), pulse position modulation (PPM) and spectrally efficient quadrature amplitude modulation (QAM) can be used for data communication. In other embodiments, power and data carrier frequencies are separated to maximize bandwidth for data communication while minimizing the tissue attenuation by lowering the frequency of external carrier waveforms during power transfer. It may also have the ability to wirelessly transmit data. See, e.g., M. J. Karimi, A. Schmid and C. Dehollain, "Wireless Power and Data Transmission for Implanted Devices via Inductive Links: A Systematic Review," in IEEE Sensors Journal, vol. 21, no. 6, pp. 7145-7161, 15 Mar. 15, 2021; herein incorporated by reference in its entirety).

In certain embodiments, the fluorescence imager further comprises a digital state machine that controls the stage of operation of the chip. For example, the stages may include i) power up, during which energy is stored in the energy storage device for chip operation, ii) illumination and imaging, which may last for 10 ms to 100 ms (but may be shorter or longer), iii) data conversion and iv) transmission. During the illumination stage, the light-emitting sources (e.g., laser diodes or LEDs) are turned on. In some embodiments, during the illumination stage, a laser diode is used that is supplied by a 33 mA current for 50 ms. In some embodiments, the chip can be programed to supply a set voltage and current to the light source. In some embodiments, multiple light sources are placed on chip, each with a different voltage supply and current supply requirement. Just prior to the illumination stage, pixels are reset, and any offset is measured and stored in pixels. During the illumination stage, the pixel is activated and integrates fluorescent emitted light. At the end of illumination, the pixel value is sampled and held in an in-pixel storage capacitor. Both the offset value and the fluorescence value from each pixel are serially fed to the analog to digital converter. The analog to digital converter converts this analog signal to a digital value which is transmitted off chip. In other embodiments, these values are stored on-chip and transmitted at a later time on demand. In some embodiments multiple wavelengths of light are used, and images are sequentially taken as described, each using a single wavelength light source. In some embodiments, multiple light sources are used (such as light sources on the imager and separate micro-stars). In these cases, the light sources of the same wavelength on different chips can be used simultaneously or sequentially. These stages can be triggered from an external transducer or guided by an internal clock. It is understood to those skilled in the art that a variety of circuit design approaches can be used to accomplish these stages of operation. In order to obtain semi-continuous monitoring (every minute, hour, day, etc.) over long periods of time (hours to days to months), without having the patient tethered to an external device to provide continuous power and data transfer, an on-chip rechargeable battery and on-chip memory storage may be added to the fluorescence imager.

The frequency of sensing (fluorescence imaging) is determined by the biologic process and the signal-to-noise ratio needed for accuracy. The sampling frequency (i.e., how many sensing operations per second) depends on the speed of the biological process. Preferably, the sampling frequency is at least two times faster than any significant biological change to accurately sample the environment. Sampling may be every second, minute, hour, day, or week depending on the process (or any time interface in between). The signal to noise ratio can be improved by acquiring multiple images that can be averaged together. Each image in this scenario must be taken before a significant change in the environment has occurred (see, e.g., Gharia et al. (2020) Mol Imaging 19:1536012120913693), herein incorporated by reference). To obtain the power necessary to accomplish this without tethering the patient to an external transducer continuously, an on-chip rechargeable battery can be used.

A clock can be added to the chip if the clock is not derived from an external source. The on-chip battery charges an on-chip capacitor to provide the high instantaneous currents needed for optical illumination and chip operation (which exceed those that the battery can provide). Once the capacitor is charged, chip operation proceeds as above, with illumination and image capture, and then analog to digital conversion. In some embodiments the power is supplied by an on-chip rechargeable battery. The digital output is then stored on chip by a data storage unit. For images that are averaged to improve SNR, on chip averaging and then storage of the averaged image can be performed on chip. Images are obtained at predefined intervals, and the process is repeated. This interval (and the number of averages) can be programed on chip or transmitted to the chip. At periodic intervals, an external transceiver interrogates the chip and signals for data upload. Data upload is performed either using US or RF back-scatter or active uplink. The battery is then recharged using ultrasound-based power transfer or RF based power transfer, and the memory is reset. The process repeats again. Other power sources can also be used. This includes energy harvesting, momentum harvesting, and nuclear power harvesting. The above process can also be used on the micro-stars (illumination only) without the imager and requisite data storage and upload.

In certain embodiments, the fluorescence imager further comprises an envelope detector for the AC input, the output of which controls a finite state machine (FSM). The FSM generates multiple control/timing signals for proper operation of the internal blocks of the imager such as sample and conversion times of the analog to digital converter. The FSM also performs packet scheduling and timing of the data uplink. The output of the envelope detector also acts as a downlink data stream that is used to wirelessly configure the imager settings such as integration time. In other embodiments wherein a precharged battery replaces the AC input, an input control signal keeps track of the transitions of the FSM by overriding the output of the timer control module.

Fluorescence Imaging

In vivo fluorescence imaging is performed by implanting at least one fluorescence imager in tissue of a subject. The tissue may be any type of tissue where imaging is desired such as diseased or damaged tissue, cancerous tissue, inflamed tissue, or tissue at risk of future disease requiring periodic or continuous monitoring (i.e. precancers tissue, transplanted tissue, tissue at high risk for tumor or disease development due to underlying genetic abnormality or mutation, such as breast tissue in a BRCA mutation carrier). Any suitable method may be used for implanting imagers in tissue. For example, the fluorescence imager can be implanted during a tissue biopsy using a biopsy needle. Multiple fluorescence imagers may be implanted in tissue to allow imaging of more cell types and extend the range of tissue imaged. The miniature size of the fluorescence imager allows it to remain in tissue longer than conventional medical probes and imaging devices, which allows the fluorescence imager to provide continuous in vivo imaging of multiple cell types in real-time for sustained periods of time.

Before performing fluorescence imaging, cells of interest in the tissue can be fluorescently labeled with one or more fluorophore conjugates. A fluorophore conjugate comprises a fluorophore conjugated to a binding agent that selectively binds directly or indirectly to a marker on a cell of interest in the tissue. An on-chip power source or external transducer is used to provide power to the fluorescence imager, wherein the on-chip light emitting sources (e.g., micro-laser diodes or LEDs) of the imager are turned on to provide excitation light to the fluorophore conjugates bound to the tissue. Alternatively, external light sources such as micro-stars implanted in the tissue can be used for illumination, which may be powered by an internal or external power source that is switched on. In some embodiments, multiple light sources are used that emit light at different excitation wavelengths suitable for generating fluorescence from multiple fluorophore conjugates bound to different target markers on cells of interest. The imaging array of the fluorescence imager detects the fluorescent light emitted from the fluorophores and records a fluorescence image of the tissue.

Power is provided to the fluorescence imager by an internal and/or external power source. In some embodiments, power is provided from an on-chip battery, a radionuclide, an on-chip photovoltaic system, or an on-chip radionuclide in combination with a scintillator and photovoltaic energy harvester for fluorescence imaging. Power may also be provided by an external power source such as, but not limited to, an ultrasound transducer, an electromagnetic (EM) transducer, an inductive transducer, or a radiofrequency (RF) transducer. Any suitable acoustic transducer such as an ultrasound or RF transducer may be used to provide power to the fluorescence imager for fluorescence imaging. Exemplary ultrasound transducers that can be used in the practice of the subject methods include, without limitation, linear transducers, convex transducers, and phased array transducers.

In certain embodiments, fluorescence imaging with the fluorescence imager is performed with one or more fluorophores having a fluorescence emission in the near-infrared (NIR) region of the light spectrum, which ranges from about 700 nm to 1700 nm. The use of NIR fluorophores is advantageous in minimizing interference from tissue autofluorescence and enhancing tissue penetration compared to other fluorophores. Preferably, the fluorescent emission wavelength is in a region of the spectrum where blood and tissue absorb minimally, and tissue penetration is maximal, such as in the range from 700 nm to 1000 nm. Any NIR fluorophore with an emission in the NIR region of the spectrum may be used with the fluorescence imager, including, but not limited to, fluorophores with fluorescence emissions at about 700, 720, 740, 760, 780, 800, 820, 840, 860, 880, 900, 920, 940, 960, 980, or 1000 nm, or any wavelength in between.

Exemplary NIR fluorophores include, without limitation, IRDye dyes (e.g., IRDye 8000 W, IRDye 680RD, IRDye 700, IRDye 750, and IRDye 800RS), CF dyes (e.g., CF680, CF680R, CF750, CF770, and CF790), Tracy dyes (e.g., Tracy 645 and Tracy 652), Alexa dyes (e.g., Alexa Fluor®660 dye, Alexa Fluor®700 dye, Alexa Fluor®750 dye, and Alexa Fluor®790), cyanine dyes (e.g., Cy7 and Cy7.5), thienothiadiazole dyes, phthalocyanine dyes, squaraine dyes, rhodamine dyes and analogues (e.g., Si-pyronine, Si-rhodamine, Te-rhodamine, and Changsha), borondipyrromethane (BODIPY) dyes, seminaphthofluorone xanthene dyes, benzo[c]heterocycle dyes (e.g., isobenzofuran dyes), and quantum dots. For a review of NIR fluorophores and their use in fluorescence imaging, see, e.g., Escobedo et al. (2010) Curr. Opin. Chem. Biol. 14(1):64-70, Hilderbrand et al. (2010) Curr. Opin. Chem. Biol. 14(1):71-79, Yuan et al. (2013) Chem. Soc. Rev. 42(2):622-661, Vats et al. (2017) Int. J. Mol. Sci. 18(5), Zhang et al. (2017) Nat. Rev. Clin. Oncol. 14(6):347-364, Gao et al. (2010) Curr. Top. Med. Chem. 10(12):1147-1157, Zhao et al. (2018) Wiley Interdiscip Rev Nanomed Nanobiotechnol. 10(3): e1483, and Haque et al. (2017) Bioorg. Med. Chem. 25(7): 2017-2034; herein incorporated by reference in their entireties.

Fluorescence imaging with the fluorescence imager may also be performed with one or more fluorophores having a fluorescence emission in the visible, NIR, or IR region of the light spectrum, which ranges from about 380 nm to 750 nm, 750 nm-1100 nm, and 1100 nm to 1500 nm. Preferred imaging wavelengths are within the optical window of tissue, extending from approximately 500 nm to 900 nm. Exemplary fluorophores with emissions in the visible region of the light spectrum include, without limitation, SYBR green, SYBR gold, a CAL Fluor dye such as CAL Fluor Gold 540, CAL Fluor Orange 560, CAL Fluor Red 590, CAL Fluor Red 610, and CAL Fluor Red 635, a Quasar dye such as Quasar 570, Quasar 670, and Quasar 705, an Alexa Fluor such as Alexa Fluor 488, Alexa Fluor 546, Alexa Fluor 555, Alexa Fluor 594, Alexa Fluor 647, and Alexa Fluor 784, a cyanine dye such as Cy3, Cy3.5, Cy5, Cy5.5, and Cy7, fluorescein, 2', 4', 5', 7'-tetrachloro-4-7-dichlorofluorescein (TET), carboxyfluorescein (FAM), fluorescein isothiocyanate (FITC), 6-carboxy-4',5'-dichloro-2',7'-dimethoxyfluorescein (JOE), hexachlorofluorescein (HEX), rhodamine, carboxy-X-rhodamine (ROX), tetramethyl rhodamine (TAMRA), and Texas Red.

Fluorophores may be conjugated to any agent that specifically binds to a marker of interest (e.g., tumor marker or immune activation marker). In some embodiments, the binding agent binds to a marker of interest with high affinity. Examples of binding agents include, without limitation, antibodies, antibody fragments, antibody mimetics, and aptamers as well as small molecules, peptides, peptoids, or ligands that bind selectively to cellular markers. The conjugates used in the subject methods include at least one fluorophore attached to the binding agent. In some embodiments, a fluorophore conjugate is used in fluorescence imaging that comprises a binding agent that selectively binds to a cell-specific marker. In some embodiments, multiple fluorophore conjugates are used, wherein the different fluorophore conjugates bind to different markers on cells of the same cell-type or different cell-types.

In certain embodiments, the binding agent comprises an antibody that specifically binds to the marker of interest. Any type of antibody may be used in fluorophore conjugates, including, without limitation, monoclonal antibodies, polyclonal antibodies, as well as hybrid antibodies, altered antibodies, chimeric antibodies, and humanized antibodies. Antibodies may include hybrid (chimeric) antibody molecules (see, for example, Winter et al. (1991) *Nature* 349: 293-299; and U.S. Pat. No. 4,816,567); F(ab')$_2$ and F(ab) fragments; F$_v$ molecules (noncovalent heterodimers, see, for example, Inbar et al. (1972) *Proc Natl Acad Sci USA* 69:2659-2662; and Ehrlich et al. (1980) *Biochem* 19:4091-4096); single-chain Fv molecules (scFv) (see, e.g., Huston et al. (1988) *Proc Natl Acad Sci USA* 85:5879-5883); nanobodies or single-domain antibodies (sdAb) (see, e.g., Wang et al. (2016) *Int J Nanomedicine* 11:3287-3303, Vincke et al. (2012) *Methods Mol Biol* 911:15-26; dimeric and trimeric antibody fragment constructs; minibodies (see, e.g., Pack et al. (1992) *Biochem* 31:1579-1584; Cumber et al. (1992) *J Immunology* 149B:120-126); diabodies, tetrabodies, affibodies, camelid antibodies, humanized antibody molecules (see, e.g., Riechmann et al. (1988) *Nature* 332:323-327; Verhoeyan et al. (1988) *Science* 239:1534-1536; and U.K. Patent Publication No. GB 2,276,169, published 21 Sep. 1994); and, any functional fragments obtained from such molecules, wherein such fragments retain specific-binding properties of the parent antibody molecule.

In other embodiments, the binding agent comprises an aptamer that specifically binds to the marker of interest. Any type of aptamer may be used, including a DNA, RNA, xeno-nucleic acid (XNA), or peptide aptamer that specifically binds to the tumor antigen. Such aptamers can be identified, for example, by screening a combinatorial library. Nucleic acid aptamers (e.g., DNA or RNA aptamers) that bind selectively to a target tumor antigen can be produced by carrying out repeated rounds of in vitro selection or systematic evolution of ligands by exponential enrichment (SELEX). Peptide aptamers that bind to a marker of interest may be isolated from a combinatorial library and improved by directed mutation or repeated rounds of mutagenesis and selection. For a description of methods of producing aptamers, see, e.g., *Aptamers: Tools for Nanotherapy and Molecular Imaging* (R. N. Veedu ed., Pan Stanford, 2016), *Nucleic Acid and Peptide Aptamers: Methods and Protocols* (Methods in Molecular Biology, G. Mayer ed., Humana Press, 2009), *Nucleic Acid Aptamers: Selection, Characterization, and Application* (Methods in Molecular Biology, G. Mayer ed., Humana Press, 2016), *Aptamers Selected by Cell-SELEX for Theranostics* (W. Tan, X. Fang eds., Springer, 2015), Cox et al. (2001) Bioorg. Med. Chem. 9(10):2525-2531; Cox et al. (2002) Nucleic Acids Res. 30(20): e108, Kenan et al. (1999) Methods Mol. Biol. 118:217-231; Platella et al. (2016) Biochim. Biophys. Acta Nov 16 pii: S0304-4165(16)30447-0, and Lyu et al. (2016) Theranostics 6(9):1440-1452; herein incorporated by reference in their entireties.

In other embodiments, the binding agent comprises an antibody mimetic. Any type of antibody mimetic may be used, including, but not limited to, affibody molecules (Nygren (2008) FEBS J. 275 (11):2668-2676), affilins (Ebersbach et al. (2007) J. Mol. Biol. 372 (1):172-185), affimers (Johnson et al. (2012) Anal. Chem. 84 (15):6553-6560), affitins (Krehenbrink et al. (2008) J. Mol. Biol. 383 (5): 1058-1068), alphabodies (Desmet et al. (2014) Nature Communications 5:5237), anticalins (Skerra (2008) FEBS J. 275 (11):2677-2683), avimers (Silverman et al. (2005) Nat. Biotechnol. 23 (12):1556-1561), darpins (Stumpp et al. (2008) Drug Discov. Today 13 (15-16):695-701), fynomers (Grabulovski et al. (2007) J. Biol. Chem. 282 (5):3196-3204), and monobodies (Koide et al. (2007) Methods Mol. Biol. 352:95-109).

In other embodiments, the binding agent comprises a small molecule ligand. Small molecule ligands encompass numerous chemical classes, e.g., small organic compounds having a molecular weight of less than about 10,000 daltons, less than about 5,000 daltons, or less than about 2,500 daltons. The small molecule will include one or more functional groups necessary for structural interaction with the target analyte, e.g., groups necessary for hydrophobic, hydrophilic, electrostatic or even covalent interactions. Where the target analyte is a protein (e.g., cellular marker), the ligand will include functional groups necessary for structural interaction with proteins, such as hydrogen bonding, hydrophobic-hydrophobic interactions, electrostatic interactions, etc., and will typically include at least an amine, amide, sulfhydryl, carbonyl, hydroxyl or carboxyl group, or preferably at least two of the functional chemical groups. The small molecule may also comprise a region that may be modified and/or participate in conjugation to a fluorophore, without substantially adversely affecting the small molecule's ability to bind to its target analyte.

Small molecule ligands can comprise cyclical carbon or heterocyclic structures and/or aromatic or polyaromatic structures substituted with one or more of the above functional groups. Small molecule ligands may also include organic compounds comprising alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracylines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Small molecule ligands are also found among biomolecules including peptides, carbohydrates, fatty acids, steroids, purines, pyrimidines, derivatives, structural analogs, or combinations thereof. The small molecule may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known small molecules may be subjected to directed or random chemical modifications, such as acylation, alkylation, esterification, amidification, etc. to produce structural analogs.

As such, the small molecule may be obtained from a library of naturally occurring or synthetic molecules, including a library of compounds produced through combinatorial means, i.e., a compound diversity combinatorial library. When obtained from such libraries, the small molecule employed will have demonstrated some desirable affinity for the protein target in a convenient binding affinity assay. Combinatorial libraries, as well as methods for the production and screening, are known in the art and described in: U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

Small molecule ligands may also include known drugs that selectively bind to receptors on cells, including, without limitation, growth factor receptors, receptor tyrosine kinases, receptor protein serine/threonine kinases, G-protein coupled receptors, cytokine receptors, lectin receptors, folate receptors, prostate-specific membrane antigen (PSMA), carbonic anhydrase IX receptor, and biotin receptors. For example, anti-cancer drugs that bind to such cellular receptors may be used as ligands to target fluorophores to cancer cells. Exemplary drugs that may be used as ligands to target cancer cells include, without limitation, Acitinib, Afatinib, Axitinib, Erlotinib, Cabozantinib, Crizotinib, Gefitinib, Imatinib, Ibrutinib, Lapatinib, Neovastat, Nilotinib, Pazopanib, Perifosine, Ponatinib, Regorafenib, Sorafenib, Sunitinib, Trametinib, and Vandetenib.

In other embodiments the binding agent comprises a membrane-targeted cleavable probe that becomes activated when it encounters a protease. Such probes comprise a synthetic peptide substrate comprising a protease cleavage site coupled to a fluorophore and a membrane targeting domain. Upon cleavage by a protease, the fluorophore is deposited in cell membranes. For a description of such protease-activated peptide probes, see, e.g., Page et al. (2015) Nature Communications 6 (8448), Backes et al. (2000) Nat. Biotechnol. 18:187-193; herein incorporated by reference.

Fluorophores may be conjugated to binding agents by any suitable method. In some instances, the fluorophore and binding agent may be directly linked, e.g., via a single bond, or indirectly linked e.g., through the use of a suitable linker, e.g., a polymer linker, a chemical linker, or one or more linking molecules or moieties. In some instances, attachment of the fluorophore and binding agent may be by way of one or more covalent interactions. In some instances, the fluorophore or binding agent may be functionalized, e.g., by addition or creation of a reactive functional group. Functionalized fluorophores or binding agents may be modified to contain any convenient reactive functional group for conjugation such as an amine functional group, a carboxylic functional group, a sulfhydryl group, a thiol functional group, and the like.

Any convenient method of bioconjugation may be used including, but not limited to, glutaraldehyde crosslinking, carbodiimide crosslinking, succinimide ester crosslinking, imidoester, crosslinking, maleimide crosslinking, iodoacetamide crosslinking, benzidine crosslinking, periodate crosslinking, isothiocyanate crosslinking, and the like. Such conjugation methods may optionally use a reactive sidechain group of an amino acid residue of the binding agent (e.g., a reactive side-chain group of a Lys, Cys, Ser, Thr, Tyr, His or Arg amino acid residue of the protein, i.e., a polypeptide linking group may be amino-reactive, thiol-reactive, hydroxyl-reactive, imidazolyl-reactive or guanidinyl-reactive). In some cases, a chemoselective reactive functional group may be utilized. Other conjugation reagents that can be used include, but are not limited to, e.g., homobifunctional conjugation reagents (e.g., (bis(2-[succinimidooxycarbonyloxy]ethyl) sulfone, I,4-Di-(3'-[2'pyridyldithio]-propionamido) butane, disuccinimidyl suberate, disuccinimidyl tartrate, sulfodisuccinimidyl tartrate, dithiobis(succinimidyl propionate), 3,3'-dithiobis(sulfosuccinimidyl propionate), ethylene glycol bis(succinimidyl succinate), and the like), heterobifunctional conjugation reagents (e.g., m-maleimidobenzoyl-N-hydroxysuccinimide ester, m-maleimidobenzoyl-N-hydroxysulfosuccinimide ester, N-γ-maleimidobutyryloxysuccinimide ester, N-γ-maleimidobutyryloxysulfosuccinimide ester, N-(8-maleimidocaproic acid) hydrazide, N-(ε-maleimidocaproyloxy) succinimide ester, N-(8-maleimidocaproyloxy) sulfo succinimide ester, N-(p-maleimidophenyl) isocyanate, N-succinimidyl(4-iodoacetyl)aminobenzoate, succinimidyl 4-(N-maleimidomethyl) cyclohexane-1-carboxylate, succinimidyl 4-(p-maleimidophenyl) butyrate, N-sulfosuccinimidyl(4-iodoacetyl)aminobenzoate, sulfosuccinimidyl 4-(N-maleimidomethyl) cyclohexane-1-carboxylate, sulfo succinimidyl 4-(p-maleimidophenyl) butyrate, I-ethyl-3-(3-dimethylaminopropyl) carbodiimide hydrochloride, I-ethyl-3-(3-dimethylaminopropyl) carbodiimide hydrochloride, maleimide PEG N-hydroxysuccinimide ester, and the like), photoreactive conjugation reagents (e.g., p-azidobenzoyl hydrazide, N-5-azido-2-nitrobenzyloxysuccinimide, p-azidophenyl glyoxal monohydrate, N-(4-[p-azidosalicylamido] butyl)-3'-(2'-pyridyldithio) propionamide, bis(P-[4-azidosalicylamido]-ethyl) disulfide, N-hydroxysuccinimideyl-4-azidosalicyclic acid, N-hydroxysulfosuccinimidyl-4-azidobenzoate, sulfosuccinimidyl 2-(7-azido-4-methylcoumarin-3-acetamide)ethyl-1,3-dithiopropionate, azido phenyl 2-(m-azido-o-nitrobenzamido)-ethyl-1,3'-propionate, sulfosuccinimidyl 6-(4'-azido-2'-nitrophenylamino) hexanoate, sulfosuccinimidyl (4-azidophenyl dithio)propionate, sulfosuccinimidyl-2-(p-azidosalicylamido)ethyl-1,3-dithiopropionate, and the like).

In some instances, attachment of a fluorophore to a binding agent of interest is mediated by one or more functional linkers. A functional linker, as used herein, refers to any suitable linker that has one or more functional groups for the attachment of one molecule to another. For example, in some instances the functional linker comprises an amino functional group, a thiol functional group, a hydroxyl functional group, an imidazolyl functional group, a guanidinyl functional group, an alkyne functional group, an azide functional group, or a strained alkyne functional group. Further exemplary functional groups and methods of crosslinking and conjugation are described in, e.g., Hermanson *Bioconjugate Techniques* (Academic Press, 3$^{rd}$ edition, 2013), herein incorporated by reference in its entirety.

In some embodiments, the fluorescence imager is embedded in a tumor and used in combination with fluorophores conjugated to cancer targeted binding agents for imaging cancerous cells. The cancer-targeting agent may comprise an antibody, an antibody mimetic, a peptide, a peptoid, an aptamer, or a small molecule ligand that selectively binds to a tumor-specific antigen or a tumor-associated antigen on cancerous cells. As discussed above, the imaging array of the fluorescence imager can be designed to simultaneously detect fluorescence at multiple wavelengths and can be used for detection of fluorescence from multiple fluorophores that emit fluorescence at different wavelengths. In some embodiments, two or more fluorophore conjugates targeting different tumor antigens are used to allow imaging of multiple cell types in tumors.

Fluorescence imaging with fluorophores conjugated to cancer targeted binding agents can be used in assessing the efficacy of therapeutic drugs in treating the cancer. For example, fluorescence imaging with fluorophores conjugated to cancer targeted binding agents can be performed after treatment with a therapy to determine if the individual is responding to treatment. Fluorescence imaging by itself or combined with other medical imaging methods can be used to evaluate whether a tumor is shrinking or growing. Further, the extent of cancerous disease (how far and where the cancer has spread) can be determined to aid in determining prognosis.

Exemplary tumor-specific antigens and tumor-associated antigens include, without limitation, oncogene protein products, mutated or dysregulated tumor suppressor proteins, oncovirus proteins, oncofetal antigens, mutated or dysregulated differentiation antigens, overexpressed or aberrantly expressed cellular proteins (e.g., mutated or aberrantly expressed growth factors, mitogens, receptor tyrosine kinases, cytoplasmic tyrosine kinases, serine/threonine kinases and their regulatory subunits, G proteins, and transcription factors), and altered cell surface glycolipids and glycoproteins on cancerous cells. For example, tumor-specific antigens and tumor-associated antigens may include without limitation, dysregulated or mutated RAS, WNT, MYC, ERK, TRK, CTAG1B, MAGEA1, Bcr-Abl, p53, c-Sis, epidermal growth factor receptor (EGFR), platelet-derived growth factor receptor (PDGFR), vascular endothelial growth factor receptor (VEGFR), HER2/neu, Src-family, Syk-ZAP-70 family proteins, and BTK family of tyrosine kinases, AbI, Raf kinase, cyclin-dependent kinases, alphafetoprotein (AFP), carcinoembryonic antigen (CEA), CA-125, MUC-1, epithelial tumor antigen (ETA), tyrosinase, melanoma-associated antigen (MAGE), and other abnormal or dysregulated proteins expressed on cancerous cells. In some embodiments, the cancer-targeted binding agent binds to a tumor antigen of interest with high affinity.

In certain embodiments, the tumor marker targeted by a binding agent is the urokinase plasminogen activator receptor (uPAR) or urokinase plasminogen activator (uPA). A number of anti-uPAR antibodies are available including the 2G10 antibody, which inhibits the uPAR interaction with urokinase plasminogen activator, and anti-uPAR antibody, 3C6, which inhibits the association of uPAR with $\beta 1$ integrin (see, e.g., LeBeau et al. (2013) Cancer Res. 73(7):2070-2081). Anti-PAR and anti-uPA antibodies can be conjugated to fluorophores for use in fluorescence imaging, according to the methods described herein, for detection of cancerous cells expressing uPAR or uPA, respectively, including, without limitation, those of breast cancer including triple negative breast cancer, pancreas cancer, prostate cancer, and melanoma.

In certain embodiments, the tumor marker targeted by a binding agent is PD-L1. A number of anti-PD-L1 antibodies are commercially available including durvalumab, pembrolizumab, atezolizumab and avelumab. Other anti-PD-L1 antibodies include C4 and DFO-C4 (see, e.g., Truillet C et al. (2018) Bioconjug. Chem. 29(1):96-103). Such anti-PD-L1 antibodies can be conjugated to fluorophores for use in fluorescence imaging, according to the methods described herein, for detection of cancerous cells expressing PD-L1, including, without limitation, those of melanoma, lung cancer, including non-small cell lung cancer (NSCLC) and small cell lung cancer (SCLC), head and neck cancer, Hodgkin lymphoma, stomach cancer, prostate cancer, bladder cancer, urothelial carcinoma, breast cancer including triple-negative breast cancer (TNBC), hepatocellular carcinoma (HCC), Merkel cell carcinoma, and renal cell carcinoma.

In certain embodiments, the tumor marker targeted by a binding agent is the epidermal growth factor receptor (EGFR). A number of anti-EGFR antibodies are available including panitumumab, cetuximab, zalutumumab, nimotuzumab, and matuzumab, which can be conjugated to fluorophores for use in fluorescence imaging, according to the methods described herein, for detection of cancerous cells expressing EGFR, including, without limitation, those of head and neck cancer, colorectal cancer, lung cancer, ovarian cancer, breast cancer, endometrial cancer, cervical cancer, bladder cancer, gastric cancer, and esophageal cancer. A number of small molecule drugs are also available that target EGFR including, without limitation, Gefitinib, Erlotinib, Lapatinib, Sorafenib, and Vandetenib, which can be conjugated to fluorophores for use in fluorescence imaging of cancerous cells expressing EGFR, according to the methods described herein.

In other embodiments, the tumor marker targeted by a binding agent is HER2. A number of anti-HER2 antibodies are also available including trastuzumab, pertuzumab, and margetuximab, which can be conjugated to fluorophores for use in fluorescence imaging, according to the methods described herein, for detection of cancerous cells expressing HER2, including, without limitation, those of breast cancer, ovarian cancer, stomach cancer, lung cancer, uterine cancer, gastric cancer, colon cancer, head and neck cancer, and salivary duct carcinoma. A number of small molecule drugs are also available that target HER2 including, without limitation, Lapatinib and Neratinib, which can be conjugated to fluorophores for use in fluorescence imaging of cancerous cells expressing HER2, according to the methods described herein.

In other embodiments, the tumor marker targeted by a binding agent is the epithelial cell adhesion molecule (EpCAM) 17-1A. A number of anti-EpCAM 17-1 $\mu$A antibodies are also available including edrecolomab, catumaxomab, and nofetumomab, which can be conjugated fluorophores for use in fluorescence imaging of cancerous cells expressing EpCAM 17-1 $\mu$A to detect cancerous cells in epithelial-derived neoplasms and various carcinomas, such as lung cancer, gastrointestinal cancer, breast cancer, ovarian cancer, pancreatic cancer, renal cancer, cervical cancer, colorectal cancer, and bladder cancer.

In other embodiments, the tumor marker targeted by a binding agent is CD20. A number of anti-CD20 antibodies are also available including rituximab, tositumomab, ocrelizumab, obinutuzumab, ocaratuzumab, ofatumumab, ibritumomab tiuxetan, ublituximab, and veltuzumab, which can be conjugated to fluorophores for use in fluorescence imaging, according to the methods described herein, for detection of cancerous cells expressing CD20, including, without limitation, those of lymphoma such as, but not limited to, marginal zone lymphoma, Hodgkins lymphoma, non-Hodgkins lymphoma; leukemia such as, but not limited to, chronic lymphocytic leukemia, acute lymphoblastic leukemia, myelogenous leukemia, and chemotherapy-resistant hairy cell leukemia; and thyroid cancer.

In other embodiments, the tumor marker targeted by a binding agent is CD52. A number of anti-CD52 antibodies are also available including alemtuzumab, which can be conjugated fluorophores for use in fluorescence imaging, according to the methods described herein, for detection of cancerous cells expressing CD52, including, without limitation, those of lymphoma such as, but not limited to, cutaneous T-cell lymphoma (CTCL) and T-cell lymphoma and chronic lymphocytic leukemia (CLL).

In other embodiments, the tumor marker targeted by a binding agent is CD22. A number of anti-CD22 antibodies are also available including inotuzumab, which can be conjugated to fluorophores for use in fluorescence imaging, according to the methods described herein, for detection of cancerous cells expressing CD22, including, without limitation, those of leukemia such as, but not limited to, lymphoblastic leukemia and hairy cell leukemia; lymphoma, and lung cancer.

In other embodiments, the tumor antigen targeted by a binding agent is CD19. A number of anti-C19 antibodies are also available including blinatumomab, MEDI-551 and MOR-208, which can be conjugated to fluorophores for use in fluorescence imaging, according to the methods described herein, for detection of cancerous cells expressing CD19, including, without limitation, those of B-cell neoplasms, non-Hodgkin lymphoma (NHL), chronic lymphocytic leukemia (CLL), acute lymphoblastic leukemia (ALL), and multiple myeloma (MM).

In certain embodiments, the tumor marker targeted by a binding agent is carcinoembryonic antigen (CEA). A number of anti-CEA antibodies are available including arcitumomab, which can be conjugated to fluorophores for use in fluorescence imaging, according to the methods described herein, for detection of cancerous cells expressing CEA, including, without limitation, those of colorectal carcinoma, gastric carcinoma, pancreatic carcinoma, lung carcinoma, breast carcinoma, and medullary thyroid carcinoma.

In certain embodiments, the tumor marker targeted by a binding agent is prostate-specific membrane antigen (PSMA). A number of anti-PSMA antibodies are available including capromab, PSMA30 nanobody, and IAB2M minibody, which can be conjugated to fluorophores for use in fluorescence imaging, according to the methods described herein, for detection of cancerous cells expressing PSMA, including, without limitation, those of prostate cancer. A number of small molecule drugs are also available that target PSMA including, without limitation, zinc binding compounds linked to a glutamate isostere or glutamate, phosphonate-, phosphate-, and phosphoramidates and ureas, fluciclovine (Axumin), MIP-1072, MIP-1095, N-(N-((S)-1,3-dicarboxypropyl) carbamoyl)-4-(18F)fluorobenzyl-L-cysteine (18F-DCFBC), which can be conjugated to fluorophores for use in fluorescence imaging of cancerous cells expressing PSMA, according to the methods described herein.

In certain embodiments, the tumor marker targeted by a binding agent is the folate receptor (FR). A number of anti-FR antibodies are available including farletuzumab and m909, which can be conjugated to fluorophores for use in fluorescence imaging, according to the methods described herein, for detection of cancerous cells expressing FR, including, without limitation, those of ovarian cancer, breast cancer, lung cancer, pleura cancer, cervical cancer, endometrial cancer, kidney cancer, bladder cancer and brain cancer, The small molecule, folate, can also be conjugated to fluorophores for use in fluorescence imaging of cancerous cells expressing FR, according to the methods described herein.

In certain embodiments, the tumor marker targeted by a binding agent is a matrix-metalloproteinase (MMP), including, without limitation, MMP1, MMP3, MMP7, MMP9, MMP10, MMP11, MMP12, MMP13, and MMP14. A number of anti-MMP antibodies are available including, which can be conjugated to fluorophores for use in fluorescence imaging, according to the methods described herein, for detection of cancerous cells expressing MMPs, including, without limitation, those of ovarian cancer, breast cancer, lung cancer, prostate cancer, stomach cancer, thyroid cancer, skin cancer, brain cancer, kidney cancer, colon cancer, bladder cancer, esophageal cancer, endometrial cancer, hepatocellular cancer, and head and neck cancer. Endogenous glycoprotein inhibitors such as tissue inhibitor of metalloproteinases (TIMPs), including TIMP-1, TIMP-2, TIMP-3, and TIMP-4 as well as a number of small molecule drugs are available that target MMPs including, without limitation, doxycycline, marimastat (BB-2516), and cipemastat, which can be conjugated to fluorophores for use in fluorescence imaging of cancerous cells expressing MMPs, according to the methods described herein.

In other embodiments, the binding agent selectively binds to an immune activation marker, which may include adaptive immunity activation markers and innate immunity activation markers. Exemplary immune activation markers include, without limitation, B220, CTLA-4, PD-1, CD1c, CD3, CD5, CD8, CD11b, CD11c, CD13, CD14, CD16, CD18, CD20, CD21, CD23, CD25, CD27, CD28, CD32, CD38, CD40, CD41, CD43, CD44, CD45RA, CD45RO, CD54, CD56, L-selectin (CD62L), CD63, CD66b, CD68, CD69, CD80, CD83, CD86, CD88, CD95, CD107a, CD161, CD163, CD164, CD200R, CD203c, MHCII (HLA-DR), MMR/CD206, MGL1, MGL2, Egr2, CD107a, LAMP-2 (CD107b), CD115, Ly-6C, LAMP-I (CD1-7a), NKp46, NKp30, CRTH2/DP2, CCR7, OX40, 4-1BBL, granzymes, perforin, IL-1, IL-1B, IL-2, IL-4, IL-5, IL-6, IL-8, IL-10, IL-12, IL-13, IL-17, IL-18, IL-21, IL-22, IL-25, IL-26, IL-10, TGF-beta, IFN-gamma, TNF-alpha, TNF-beta, NKG2D, CXCR5, IRTA1, IRTA2, lymphotoxin, leukotriene B4, granulocyte-macrophage colony stimulating factor (GM-CSF), and macrophage migration inhibitory factor (MIF).

Systems

The present disclosure also provides systems which find use, e.g., in practicing the subject methods. In some embodiments, the system may include a fluorescence imager as described herein, an external or internal power source; and an external data receiving device.

In certain embodiments, the external power source is an ultrasound transducer, an electromagnetic (EM) transducer, an inductive transducer, or a radiofrequency (RF) transducer. The system may also comprise an internal power source such as a battery, a radionuclide, a photovoltaic system, or a radionuclide in combination with a scintillator and photovoltaic energy harvester. The external power source may be used, for example, to charge an on-chip battery that stores and provides power to the chip.

In a further aspect, the external data receiving device may include an external processor, a storage component (i.e., memory), a display component, and other components typically present in general purpose computers. In some embodiments, the external data receiving device is a computer or handheld device (e.g., a cell phone or tablet). The storage component stores information accessible by the processor, including instructions that may be executed by the processor and data that may be retrieved, manipulated, or stored by the processor. The processor is programmed to process data received from the fluorescence imager and display fluorescence images.

In certain embodiments, the external data receiving device further comprises a wireless communication unit in communication with a wireless communication unit of the fluorescence imager. The wireless communication unit may utilize a wireless communication protocol, for example, using an electromagnetic carrier wave (e.g., a radio wave, microwave, or an infrared carrier wave) or ultrasound to receive data from the internal data storage unit of the fluorescence imager.

The storage component includes instructions. For example, the storage component includes instructions for processing fluorescence imaging data acquired by the fluorescence imager. The computer processor is coupled to the storage component and configured to execute the instructions stored in the storage component in order to receive data from the fluorescence imager and process the data using one or more algorithms, as described herein. The display component displays the processed fluorescence imaging data.

The storage component may be of any type capable of storing information accessible by the processor, such as a hard-drive, memory card, ROM, RAM, DVD, CD-ROM, USB Flash drive, write-capable, and read-only memories. The processor may be any well-known processor, such as processors from Intel Corporation. Alternatively, the processor may be a dedicated controller such as an ASIC.

The instructions may be any set of instructions to be executed directly (such as machine code) or indirectly (such as scripts) by the processor. In that regard, the terms "instructions," "steps" and "programs" may be used interchangeably herein. The instructions may be stored in object code form for direct processing by the processor, or in any other computer language including scripts or collections of independent source code modules that are interpreted on demand or compiled in advance.

Data may be retrieved, stored, or modified by the processor in accordance with the instructions. For instance, although the system is not limited by any particular data structure, the data may be stored in computer registers, in a relational database as a table having a plurality of different fields and records, XML documents, or flat files. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information which is used by a function to calculate the relevant data.

In certain embodiments, the processor and storage component may comprise multiple processors and storage components that may or may not be stored within the same physical housing. For example, some of the instructions and data may be stored on removable CD-ROM and others within a read-only computer chip. Some or all of the instructions and data may be stored in a location physically remote from, yet still accessible by, the processor. Similarly, the processor may comprise a collection of processors which may or may not operate in parallel.

The system may further include at least one fluorophore conjugate (i.e., fluorophore conjugated to a binding agent that selectively binds to a cellular marker of interest) for carrying out the methods described herein. In some embodiments, the system includes multiple fluorescence imagers and multiple fluorophore conjugates, which can be used in fluorescence imaging of multiple markers and cell-types. The system may further include multiple external light sources (e.g., micro-stars) for implantation in tissue.

The system can be used to monitor the cellular states of tissue over time. This can consist of implanting the fluorescence imager (and taking initial baseline readings for offset, calibration, assessing power and data transfer). To measure the baseline or background biological activity, one or more targeted imaging agents (as described above—small molecule, peptide, antibody derivative or other) conjugated to a fluorophore(s) can be injected and imaged. The baseline tissue activity can be monitored. For example, to see if diseased tissue is progressing in the disease state, or if at risk tissue is becoming diseased (such as a pre-cancerous tissue transforming into cancer—for example ductal carcinoma in situ (DCIS) into invasive breast cancer, or a low-grade prostate cancer into a higher-grade prostate cancer). Alternatively, the response to a drug can be measured by comparing the tissue images prior to administering the drug or therapy (such as radiation), and monitoring afterwards to assess response in real time. Repeated injections of the imaging agent can extend the imaging timeline. The response can be transmitted in real time or periodically to the external receiver/transducer.

Components of systems for carrying out the presently disclosed methods are further described in the examples below.

Kits

Also provided are kits comprising a fluorescence imager on a chip or system, as described herein. A fluorescence imager with or without an on-chip light source may be provided in the kit. If the fluorescence imager does not comprise an on-chip light source, the kit may further comprise an external light source such as a micro-star light source, as described herein. In some embodiments, the fluorescence imager is contained in a sterile package. In addition, the kit may include an external transducer such as a portable ultrasound or RF transducer. The kit may further include at least one fluorophore conjugate (i.e., fluorophore conjugated to a binding agent that selectively binds to a cellular marker of interest) for carrying out the methods described herein. In some embodiments, the kit includes multiple fluorescence imagers and multiple fluorophore conjugates, which can be used in fluorescence imaging of multiple markers and cell-types. The kit may further include multiple external light sources (e.g., micro-stars) for implantation in tissue.

Compositions can be in liquid form or can be lyophilized and contained in one or more containers. Suitable containers for the compositions include, for example, bottles, vials, syringes, and test tubes. Containers can be formed from a variety of materials, including glass or plastic. The kit can further comprise a container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery devices. The delivery device may be pre-filled with the compositions.

In addition to the above components, the subject kits may further include (in certain embodiments) instructions for practicing the subject methods. In some embodiments, instructions for using the fluorescence imager for fluorescence imaging of tissue in a patient are provided in the kits.

These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-85 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A fluorescence imager comprising:
   a) an imaging array comprising a plurality of photodiodes arrayed on the surface of a chip, wherein each photodiode is coated with at least one layer of filter material that functions as an optical filter;
   b) a plurality of light emitting sources to provide excitation light, wherein the plurality of light emitting sources are located on the chip or externally;
   c) an on-chip or off-chip energy storage device to supply power for operation of the fluorescence imager;
   d) a data storage unit in communication with the imaging array, wherein the data storage unit stores imaging data from the imaging array; and
   e) an application-specific integrated circuit (ASIC) configured to control voltages and supply power from the on-chip or off-chip energy storage device to the imaging array, the plurality of light emitting sources on the chip, and the data storage unit.

2. The fluorescence imager of aspect 1, wherein the fluorescence imager has dimensions of less than or equal to 5 mm in length.

3. The fluorescence imager of aspect 1 or 2, wherein the light emitting sources are micro-laser diodes or light-emitting diodes.

4. The fluorescence imager of aspect 3, wherein the plurality of light-emitting diodes further comprises an emission filter on each light-emitting diode.

5. The fluorescence imager of any one of aspects 1 to 4, wherein the on-chip energy storage device or the off-chip energy storage device comprises a battery, a capacitor, a radionuclide, a photovoltaic system, or a radionuclide in combination with a scintillator and photovoltaic energy harvester.

6. The fluorescence imager of aspect 5, wherein the battery is rechargeable.

7. The fluorescence imager of any one of aspects 1 to 6, further comprising a piezoelectric substrate attached to the surface of the chip or a solid support containing the chip, wherein the piezoelectric substrate is configured to receive ultrasound power from an external ultrasound transducer and supply power for operation of the fluorescence imager, wherein electrical energy output from the piezoelectric substrate in response to receiving the ultrasound power is stored in the on-chip energy storage device or the off-chip energy storage device.

8. The fluorescence imager of aspect 7, wherein the piezoelectric substrate is a piezoelectric crystal or piezoelectric ceramic.

9. The fluorescence imager of aspect 7 or 8, wherein the on-chip or off-chip energy storage device is a capacitor or rechargeable battery that stores electrical energy output from the piezoelectric substrate in response to receiving the ultrasound power, wherein the capacitor or rechargeable battery supplies power to the plurality of light emitting sources on the chip and the imaging array.

10. The fluorescence imager of any one of aspects 1 to 9, further comprising an on-chip antenna configured to receive radiofrequency (RF) power from an external RF transducer or electromagnetic power inductively transferred to a coil from an external inductive transducer and supply power for operation of the fluorescence imager, wherein electrical energy output from the on-chip antenna in response to receiving the RF or electromagnetic power is stored in the on chip-energy storage device.

11. The fluorescence imager of aspect 10 wherein the on-chip energy storage device or the off-chip energy storage device is a capacitor or rechargeable battery that stores electrical energy output from the antenna in response to receiving the RF power or the electromagnetic power, wherein the capacitor or rechargeable battery supplies power to the plurality of light emitting sources on the chip and the imaging array.

12. The fluorescence imager of any one of aspects 1 to 11, wherein the ASIC further comprises a rectifier, a DC voltage regulator, a reference voltage generator, or a power-on-reset (POR) circuit, or a combination thereof.

13. The fluorescence imager of any one of aspects 1 to 12, further comprising a data processing unit in communication with the data storage unit, wherein the data storage unit stores processed imaging data from the imaging array.

14. The fluorescence imager of any one of aspects 1 to 13, further comprising a backscattering modulator unit or an active modulator implementing amplitude shift keying (ASK), phase shift keying (PSK), frequency shift keying (FSK), pulse width modulation amplitude shift keying (PWM-ASK), pulse position modulation (PPM) or spectrally efficient quadrature amplitude modulation (QAM), or a combination thereof, in communication with the imaging array.

15. The fluorescence imager of any one of aspects 1 to 14, further comprising a first wireless communication unit in communication with the data storage unit and an external data receiving device comprising a second wireless communication unit.

16. The fluorescence imager of aspect 15, wherein the first wireless communication unit utilizes a wireless communication protocol using an electromagnetic carrier wave or ultrasound to transfer data from the data storage unit to the external data receiving device comprising the second wireless communication unit.

17. The fluorescence imager of aspect 16, wherein the electromagnetic carrier wave is a radio wave, microwave, or an infrared carrier wave.

18. The fluorescence imager of any one of aspects 15 to 17, wherein the external data receiving device Is a computer or handheld device.

19. The fluorescence imager of aspect 18, wherein the handheld device is a cell phone or tablet.

20. The fluorescence imager of any one of aspects 1 to 19, wherein the plurality of light emitting sources located externally are implantable in tissue.

21. The fluorescence imager of aspect 20, wherein the plurality of light emitting sources located externally are micro-star light sources.

22. The fluorescence imager of aspect 20 or 21, wherein an external power source supplies power to the plurality of light emitting sources located on-chip or externally.

23. The fluorescence imager of any one of aspects 1 to 22, wherein said at least one layer of filter material comprises or consists of amorphous silicon, crystalline silicon, gallium phosphide, cadmium selenide, gallium arsenide, or indium phosphide.

24. The fluorescence imager of any one of aspects 1 to 23, wherein the thickness of the layer of filter material is less than 100 microns.

25. The fluorescence imager of aspect 24, wherein the thickness of the layer of filter material ranges from about 5 microns to about 30 microns.

26. The fluorescence imager of any one of aspects 1 to 25, wherein the thickness of the layer of filter material on all the photodiodes is the same.

27. The fluorescence imager of any one of aspects 1 to 25, wherein the thickness of the layer of optical filter material on at least two photodiodes is different.

28. The fluorescence imager of aspect 27, wherein the thickness of the layer of filter material is varied on the plurality of photodiodes to allow selection of light at different fluorescence emission wavelengths for multiple fluorophores having different fluorescence emission spectra.

29. The fluorescence imager of any one of aspects 1 to 28, wherein the fluorophore of interest has a fluorescence emission in the near-infrared or visible region of the electromagnetic spectrum, and the band gap and the thickness of the layer of filter material is chosen to allow selection of near-infrared light or visible light at the fluorescence emission wavelength of the fluorophore.

30. The fluorescence imager of any one of aspects 1 to 29, wherein the optical filter is an absorption filter or an interference filter.

31. The fluorescence imager of aspect 30, wherein the absorption filter has a band gap and thickness suitable to allow light at a fluorescence emission wavelength of a fluorophore of interest to pass through to the photodiode.

32. The fluorescence imager of aspect 30, wherein the interference filter is a single bandpass, dual bandpass, triple bandpass, or quadruple bandpass interference filter.

33. The fluorescence imager of any one of aspects 30 to 32, wherein the interference filter further comprises a layer of absorption filter material on top of the interference filter or underneath the interference filter.

34. The fluorescence imager of any one of aspects 30 to 33, wherein the interference filter further comprises one or more layers of material comprising a plurality of angle selective gratings, collimators, or fiber optic plates that blocks light that is not incident within 30° of an axis perpendicular to the plane of the chip.

35. The fluorescence imager of any one of aspects 30 to 33, wherein the interference filter further comprises one or more layers of material comprising a plurality of fiber optic plates that blocks light that is not incident within 6° of an axis perpendicular to the plane of the chip.

36. The fluorescence imager of any one of aspects 30 to 33, wherein the interference filter further comprises one or more layers of material comprising a plurality of angle selective gratings that blocks light that is not incident within 15° of an axis perpendicular to the plane of the chip.

37. The fluorescence imager of aspect 34, wherein said one or more layers of material comprising a plurality of angle selective gratings, collimators, or fiber optics are on top of the layer of filter material, underneath the layer of filter material, or both on top and underneath the layer of filter material.

38. The fluorescence imager of aspect 37, wherein said layer on top of the layer of filter material blocks light that is not incident within 10°-15° of an axis perpendicular to the plane of the chip.

39. The fluorescence imager of aspect 38, wherein said layer on top of the layer of filter material has a thickness of about 100 microns to about 500 microns.

40. The fluorescence imager of any one of aspects 37 to 39, wherein said layer underneath the layer of filter material blocks light that is not incident within 5°-30° of an axis perpendicular to the plane of the chip.

41. The fluorescence imager of aspect 40, wherein said layer underneath the layer of filter material has a thickness of about 8 microns or less.

42. The fluorescence imager of any one of aspects 1 to 41, further comprising an on-chip clock.

43. The fluorescence imager of any one of aspects 1 to 42, wherein the fluorescence imager has no optical lens.

44. The fluorescence imager of any one of aspects 1 to 43, further comprising a digital state machine that controls stages of operation of the chip.

45. The fluorescence imager of aspect 44, wherein the stages of operation comprise power-up, illumination and imaging, data storage, and transmission of imaging data.

46. The fluorescence imager of aspect 45, wherein the transmission of imaging data can be triggered on demand or at preset time intervals.

47. The fluorescence imager of aspect 45 or 46, wherein the stages of operation are triggered by an external transducer or guided by an on-chip clock.

48. The fluorescence imager of any one of aspects 1 to 47, wherein the data storage unit stores data from multiple fluorescence images.

49. The fluorescence imager of any one of aspects 1 to 48, further comprising an edge computing device connected to the data storage unit, wherein the edge computing device receives data from the data storage unit.

50. The fluorescence imager of any one of aspects 1 to 49, further comprising a solid support, wherein the chip and the off-chip energy storage device or a piezoelectric substrate, or a combination thereof are on the surface of the solid support.

51. A system comprising:
    a) the fluorescence imager of any one of aspects 1 to 50;
    b) an external or internal power source; and
    c) an external data receiving device.

52. The system of aspect 51, wherein the external power source is an ultrasound transducer, an electromagnetic (EM) transducer, an inductive transducer, or a radiofrequency (RF) transducer.

53. The system of aspect 51 or 52, wherein the external power source is used to charge an on-chip battery that provides power to the chip.

54. The system of aspect 51, wherein the internal power source comprises a battery, a radionuclide, a photovoltaic system, or a radionuclide in combination with a scintillator and photovoltaic energy harvester.

55. The system of any one of aspects 51 to 54, further comprising a fluorophore conjugate comprising a fluorophore conjugated to a binding agent that specifically binds to a cellular marker of interest.

56. The system of aspect 55, wherein the binding agent is an antibody, an antibody mimetic, a peptide, a peptoid, an aptamer, or a small molecule ligand that selectively binds to the cellular marker of interest.

57. The system of aspect 55 or 56, wherein the cellular marker of interest is a tumor-specific antigen, a tumor-associated antigen, or an immune activation marker.

58. The system of any one of aspects 51 to 57, wherein the external power source is portable.

59. The system of any one of aspects 51 to 58, wherein the external data receiving device comprises a wireless communication unit.

60. The system of aspect 59, wherein the wireless communication unit utilizes a wireless communication protocol using an electromagnetic carrier wave or ultrasound to receive data from the internal data storage unit of the fluorescence imager.

61. The system of aspect 60, wherein the electromagnetic carrier wave is a radio wave, microwave, or an infrared carrier wave.

62. The system of any one of aspects 51 to 61, wherein the external data receiving device further comprises a processor programmed to process data received from the fluorescence imager and display fluorescence images.

63. The system of aspect 62, wherein the external data receiving device Is a computer or handheld device.

64. The system of aspect 63, wherein the handheld device is a cell phone or tablet.

65. The system of any one of aspects 51 to 64, further comprising a display component, wherein the display component is connected to the external data receiving device.

66. A kit comprising the fluorescence imager of any one of aspects 1 to 50 and instructions for using the fluorescence imager for in vivo fluorescence imaging.

67. The kit of aspect 66, further comprising at least one fluorophore conjugate comprising a fluorophore conjugated to a binding agent that specifically binds to a cellular marker of interest.

68. The kit of aspect 67, wherein the binding agent is an antibody, an antibody mimetic, a peptide, a peptoid, an aptamer, or a small molecule ligand that selectively binds to the cellular marker of interest.

69. The kit of aspect 67 or 68, wherein the cellular marker of interest is a tumor-specific antigen, a tumor-associated antigen, or an immune activation marker.

70. The kit of any one of aspects 66 to 69, further comprising an external power source.

71. The kit of aspect 70, wherein the external power source is an ultrasound transducer, an electromagnetic (EM) transducer, an inductive transducer, or a radiofrequency (RF) transducer.

72. The kit of aspect 70 or 71, wherein the external power source is portable

73. The kit of any one of aspects 66 to 72, further comprising at least one micro-star external light source.

74. A method of in vivo fluorescence imaging, the method comprising:
    a) implanting at least one fluorescence imager according to any one of aspects 1 to 50 in tissue of a subject;
    b) contacting a cell of interest with at least one fluorophore conjugate, wherein the fluorophore conjugate comprises a fluorophore conjugated to a binding agent that selectively binds to a target marker on the cell of interest; and
    c) providing power to the fluorescence imager, wherein the plurality of light emitting sources located on the chip or externally provides excitation light at an excitation wavelength of the fluorophore, and the imaging array detects fluorescent light emitted from the fluorophore.

75. The method of aspect 74, wherein said implanting comprises implanting a plurality of fluorescence imagers in the tissue.

76. The method of aspect 74 or 75, further comprising implanting a plurality of light emitting sources externally in the tissue of the subject.

77. The method of aspect 76, wherein the plurality of light emitting sources are micro-star external light sources.

78. The method of aspect 76 or 77, wherein the plurality of light emitting sources comprises multiple light sources emitting light at different excitation wavelengths suitable for generating fluorescence from multiple fluorophore conjugates bound to different target markers on cells of interest.

79. The method of any one of aspects 74 to 78, wherein the tissue is diseased tissue or cancerous tissue.

80. The method of any one of aspects 74 to 79, wherein the binding agent is an antibody, an antibody mimetic, a peptide, a peptoid, an aptamer, or a small molecule ligand that selectively binds to the marker of interest.

81. The method of any one of aspects 74 to 80, wherein the marker of interest is a tumor-specific antigen, a tumor-associated antigen, or an immune activation marker.

82. The method of any one of aspects 74 to 81, wherein the tissue is contacted with at least two different fluorophore conjugates, wherein each fluorophore conjugate comprises a different fluorophore that emits fluorescent light at a different emission wavelength, and each fluorophore conjugate comprises a different binding agent that selectively binds to a different marker.

83. The method of aspect 82, wherein the different binding agents of the fluorophore conjugates selectively bind to markers that are selectively expressed on cells of the same cell-type or different cell-types.

84. The method of any one of aspects 74 to 83, wherein at least one marker is selected from the group consisting of a urokinase plasminogen activator receptor (uPAR), a urokinase plasminogen activator (uPA), PD-1, PD-L1, CTLA-4 CD4, Ly6G, CD8, CD69, CD25, perforin, granzyme b, granzyme k, alphafetoprotein (AFP), carcinoembryonic antigen (CEA), CA-125, MUC-1, epithelial tumor antigen (ETA), ras, and p53.

85. The method of any one of aspects 74 to 84, wherein said providing power comprises providing power from an on-chip battery, a radionuclide, an on-chip photo-voltaic system, an on-chip radionuclide in combination with a scintillator and photovoltaic energy harvester, an external ultrasound transducer, an external electromagnetic (EM) transducer, an external inductive transducer, or an external radiofrequency (RF) transducer.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

Example 1

An In Vivo Wireless Fluorescence Imager
Introduction

An in vivo wireless sensor providing real-time response within tumors would provide a ground-breaking means to guide optimal, personalized patient care—conveying therapeutic response in real-time. This is particularly critical in the modern era of immunotherapy for cancer treatment, where durable, impactful responses are achieved for only a subset of patients, who cannot be identified a priori. Immediate response assessment allows (1) patients who are not responding to avoid the toxicity of immunotherapy, and immediately change to an alternative therapy, and (2) opens the door to novel strategies to shift a 'cold', or non-responsive tumor, to 'hot', through delivery of additional therapies which can alter the balance of the immune microenvironment in the tumor.

Real-time, intratumoral sensing has been an important, yet elusive goal due to the inherent physical limits of conventional clinical imagers, the inability to image multiple biological labels simultaneously with the spatial resolution necessary to image immune infiltration throughout the tumor, and the lack of biologics to adequately label multiple key cells responsible for tumor and immune response. Furthermore, high sensitivity monitoring allows off-tumor effects that cause toxicity to be detected prior to clinically manifesting. Our platform places the functionality of highly-sensitive fluorescence microscopes into a sub-millimeter form-factor to sense tumor response and changes in the immune infiltrate from within the tumor.

To directly and continuously image both tumor and immune response within the tumor microenvironment, we require implantable multicolor fluorescence microscopy. This necessitates extreme miniaturization of a fluorescence microscope coupled with a wireless interface in a form-factor the size of a grain of rice, such that multiple sensors can be placed directly within a tumor. Our innovations integrate the full functionality of a fluorescence microscope (illumination, filtering, focusing and image capture) with the versatility of an integrated circuit ("computer chip") through key innovations in biosensor design:

In vivo imaging is accomplished with chip-scale fluorescence microscopy using on-pixel microfabricated collimators obviating lenses (7), custom optical filters optimized for near-infrared dyes (2), micron-proximity to tissue for high sensitivity (1), and low-noise, high-speed imager design that converts light to images at the point of imaging (8), eliminating the need for restrictive fiber optics, without loss of sensitivity.

Leveraging deep integration of electronics and nanophotonics, we embedded microfabricated optical structures at the pixel level, creating monolithically integrated sensors capable of illumination and imaging within the body, precisely controlling illumination patterns to enhance image resolution. On-chip integration of wireless power and data transfer was used to eliminate the need for batteries and wires. A cluster of sensors is used to deconvolve a 3D image from within tissue by imaging from different directions.

Custom designed antibodies (9) are used to identify both tumor and key immune cells. Fluorophore-conjugated antibodies targeted to key markers of immune activation and tumor cells in a breast cancer model were used in imaging the immune response using a combination of checkpoint inhibitors and focal radiation through quantification of T-cell infiltrate and cell death.

Chip-Based Multicolor Microscopy

Fluorescence microscopes and optical-based imagers cannot be easily miniaturized to the millimeter scale encountering fundamental limitations when fabricating optics at the microscale (10) such as aberration and imperfections, and miniaturized microscopes are still several centimeters in length (11). To achieve a planar, scalable imager with minimal thickness, we removed conventional optics—the limiting factor for miniaturization—and transformed each component of a conventional fluorescent microscope into a planar, scalable, microfabricated layer (FIG. 3).

Chip-scale, multicolor, in vivo fluorescence imaging. Using our ultra-compact fluorescence imager, we eliminate hard to miniaturize optics using micro-fabricated collimators (7) for spatial resolution. High performance, multichannel optical filters are made using semi-conductor materials leveraging their inherent band gaps. Microscopy on a "computer chip" allows unparalleled versatility to integrate a myriad of electronic and photonic functions in a millimeter-scale device. Integration of analog to digital converters on chip provides a digital signal robust to variations in tumor position and signal degradation. Analogous to cellular phones and wireless RF-ID tags, we integrate a wireless power and bi-directional communication for a standalone, chronic millimeter-scale sensor platform.

Lenses: First, we take advantage of placing the imager directly in tissue itself: the micron to millimeter-proximity of the imager to tumor cells captures light before it diverges—preserving spatial resolution and increasing sensitivity. We then focus light without bulky, difficult to miniaturize lenses with in-pixel integration of microfabricated angle-selective gratings (ASG), replacing traditional focusing optics as demonstrated in (1, 7). These microfabricated structures measure just 2.4 µm wide by 6.8 µm tall (FIG. 3D), and are made directly from the metal interconnect layers inherent to all CMOS processes without any additional post-processing or increase in device thickness. This approach leverages the directionality of light to mitigate the need for optics, optically coupling each photodiode to the tissue directly opposite it, while blocking the surrounding background and signal from neighboring cells to achieve high contrast and spatial resolution imaging without optics. Our work has shown that microfabricated ASGs (7) increase spatial resolution by 4× by reducing each pixel's viewing angle, defined by the full width half-maximum (FWHM), from 120° without ASG to 36° measured in air, and to 28° in fluid.

Filters: Next, we designed our own optical filters to meet the unique and stringent requirements of fluorescence imaging without optics. The primary challenge for fluorescence imaging is blocking the 100,000 to 1,000,000-fold brighter excitation (illumination) light from the weak fluorescent emitted light, which differs in color by only ~50 nm. Conventional microscopes use multilayer interference filters, but their performance is highly dependent on the incident angle of light, demanding precision optical alignment and focusing optics. In an optics free system (necessary for extreme miniaturization) unfocused light incident at oblique angles will then bleed through, saturating the detector and masking the faint fluorescence image. Absorption filters address this, but still only attenuate light by 3-4 orders of magnitude despite being several millimeters thick. These filters would significantly increase both the size of our sensor and the distance between the imager and tissue, diminishing both resolution and sensitivity.

We seek to block illumination light by 5-6 orders of magnitude in <100 µm thickness to increase sensitivity while maintaining an ultra-compact form factor. We solve this problem by developing high-performance, tunable near-infrared amorphous silicon (a-Si) absorption filters, which we have fabricated (2) (FIG. 3C). These filters leverage the intrinsic band gap of microfabricated materials to create cut-off (long pass) filters, removing excitation light by $>10^5 \times$ without the need for precise optical alignment—opening the door to imaging fluorophores without lenses. (The lack of silicon photodiode responsivity above ~850 nm combines to create a bandpass filter.)

Figure 5:
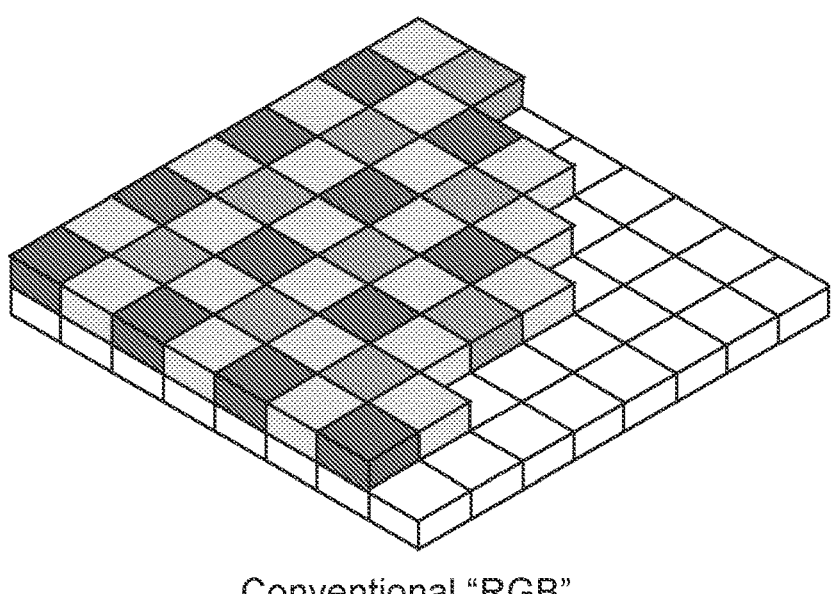
FIG. 5. Tri-Color Integrated Optical Filter.

Wavelength tunability is achieved by altering filter thickness (FIG. 3C (2))—enabling simultaneous multi-channel (spectral) imaging on chip by patterning multiple filters on a single sensor (FIG. 5). Here we demonstrate proof of concept with 3 channel imaging using amorphous silicon. The a-Si filter is deposited to the appropriate thickness to match the fluorophore emission wavelength using standard microfabricated (PECVD) deposition techniques as described in our work (2) compatible with CMOS chips. To enable multi-color filters on a single chip, we pattern this filter like the RGB or CYMK pattering on pixels for color cameras by depositing various thickness on each pixel: 27 µm, 15 µm and 5 µm for 800 nm (IR800), 700 nm (IR700), and 660 nm (Alexa Fluor 660) imaging, directly on chip (FIG. 5).

Additional channels can be incorporated using filter materials with different band gaps, expanding the number of colors that can be simultaneously imaged. Additional fluorophores (colors) are imaged by using materials with different band-gaps, for example gallium phosphide (2.25 eV bandgap, 550 nm cutoff), cadmium selenide (1.74 eV, 710 nm cutoff), gallium arsenide (1.43 eV, 870 nm cutoff), indium phosphide (1.27 eV, 980 nm cutoff), and crystalline silicon (1.11 eV, 1100 nm cutoff).

Figure 3A:
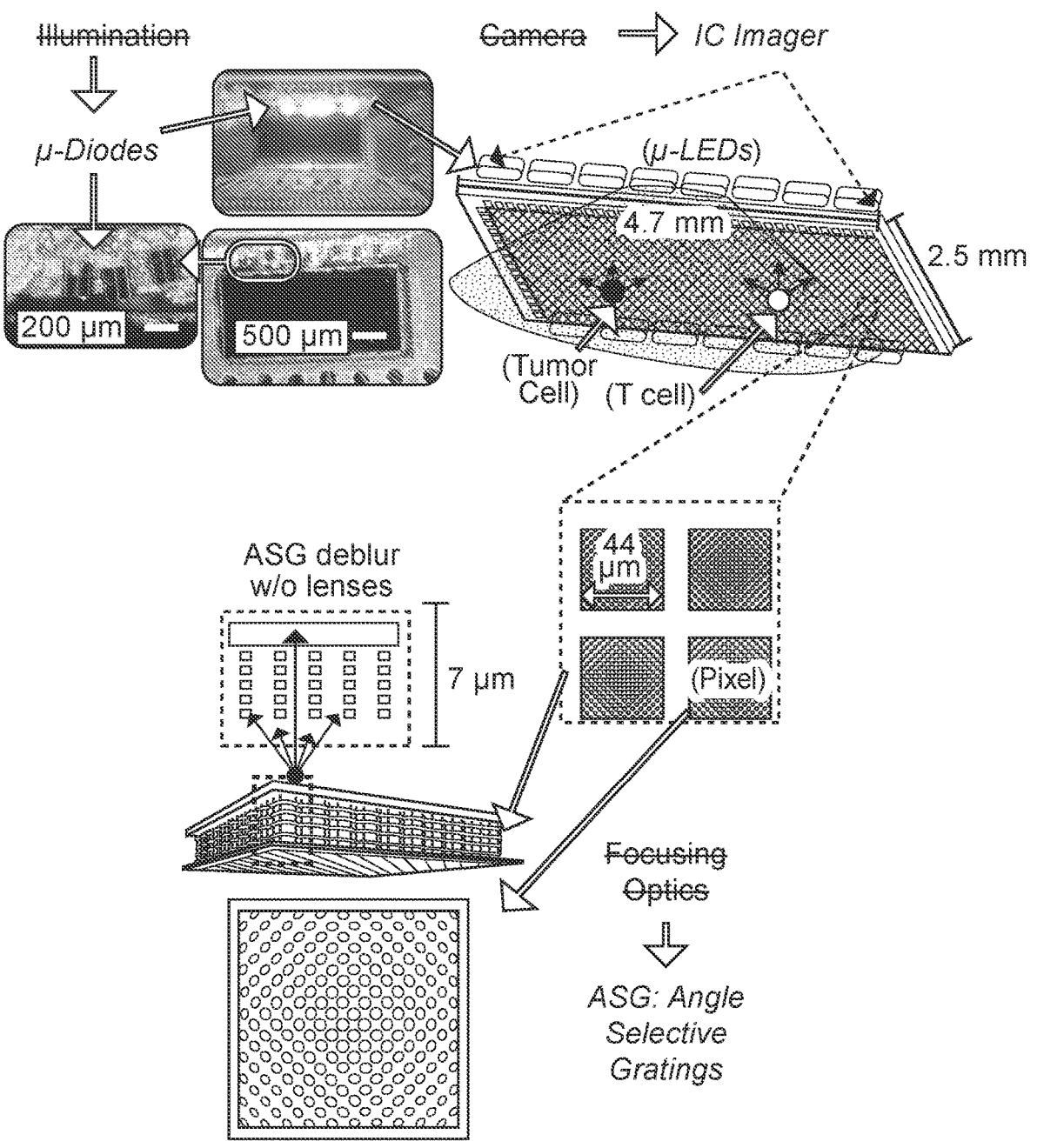
FIGS. 3A-3B. Imager.
Figure 3B:
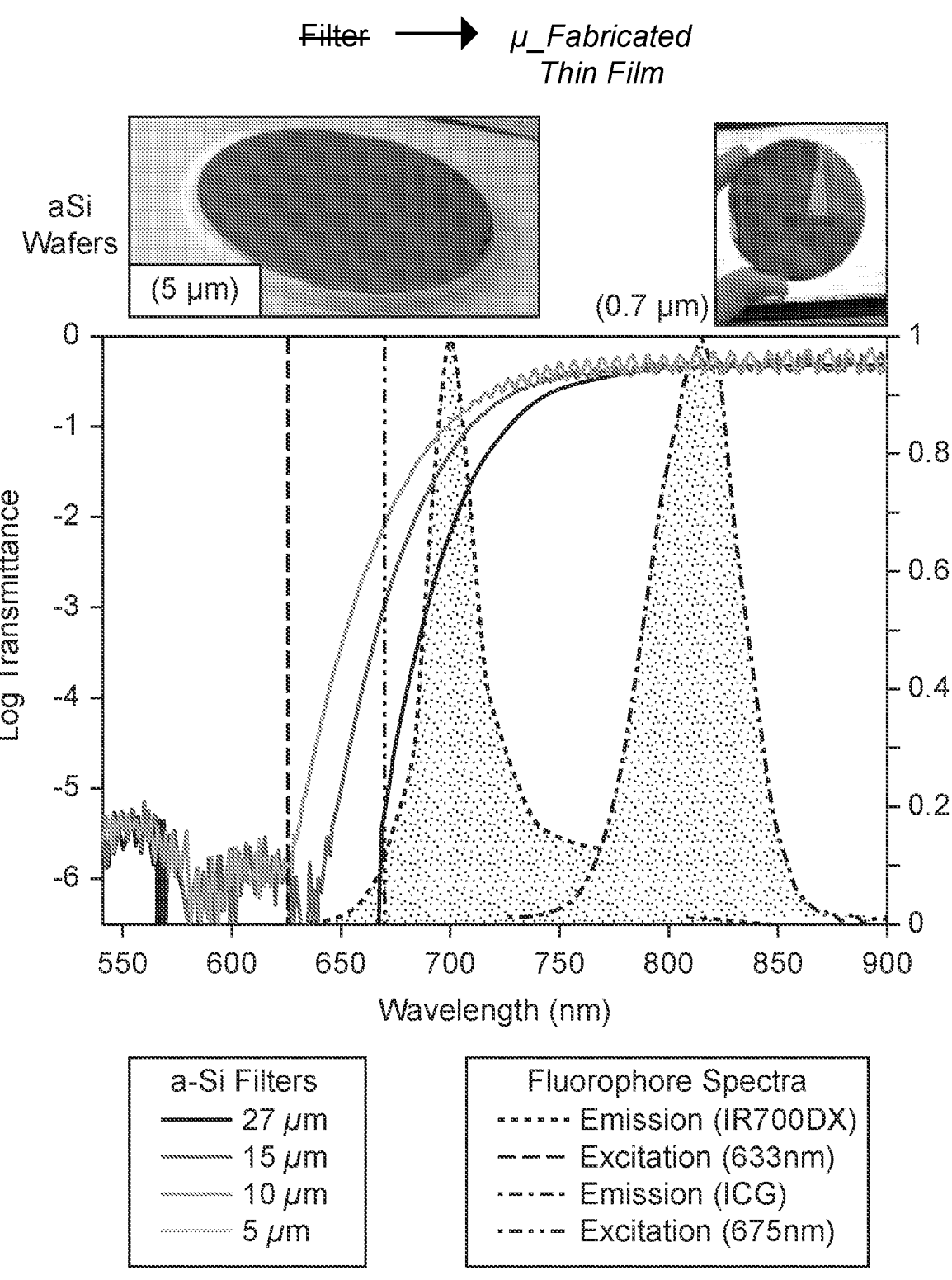
Figure 4A:
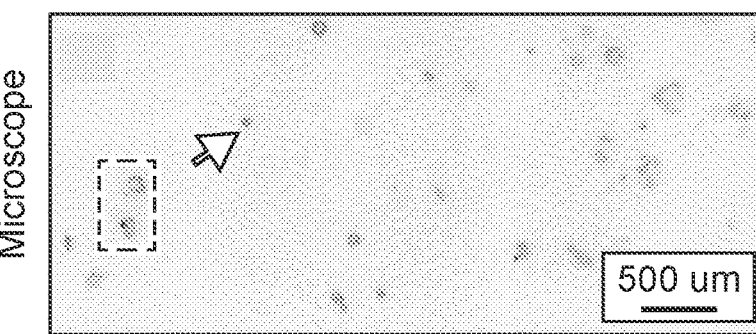
Figure 4B:
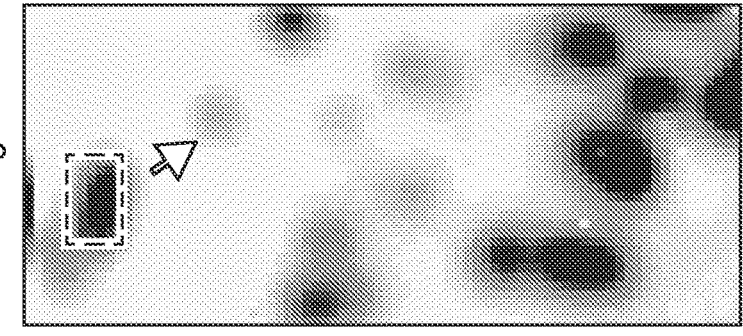
Figure 4C:
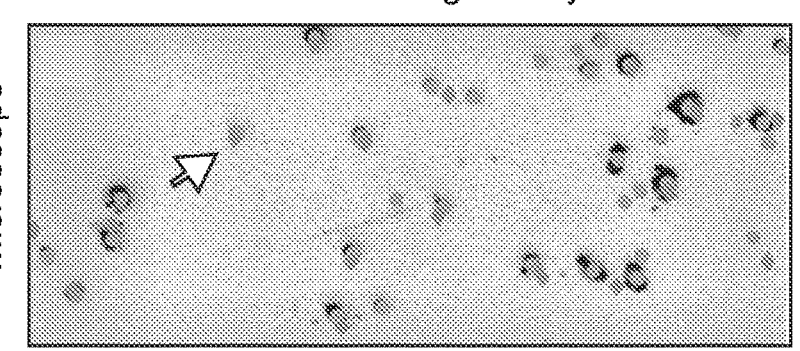
Figure 4D:
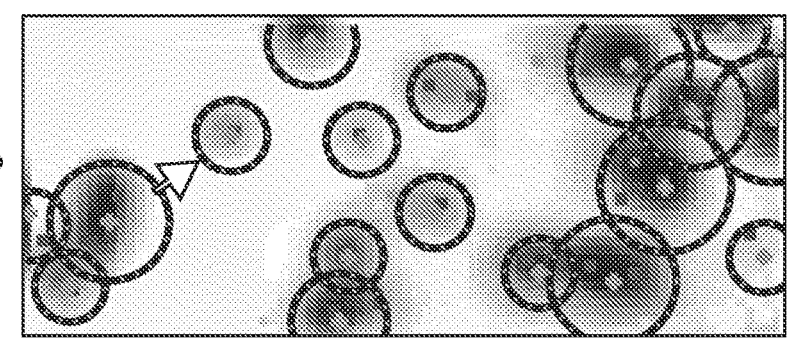
Figure 4G:
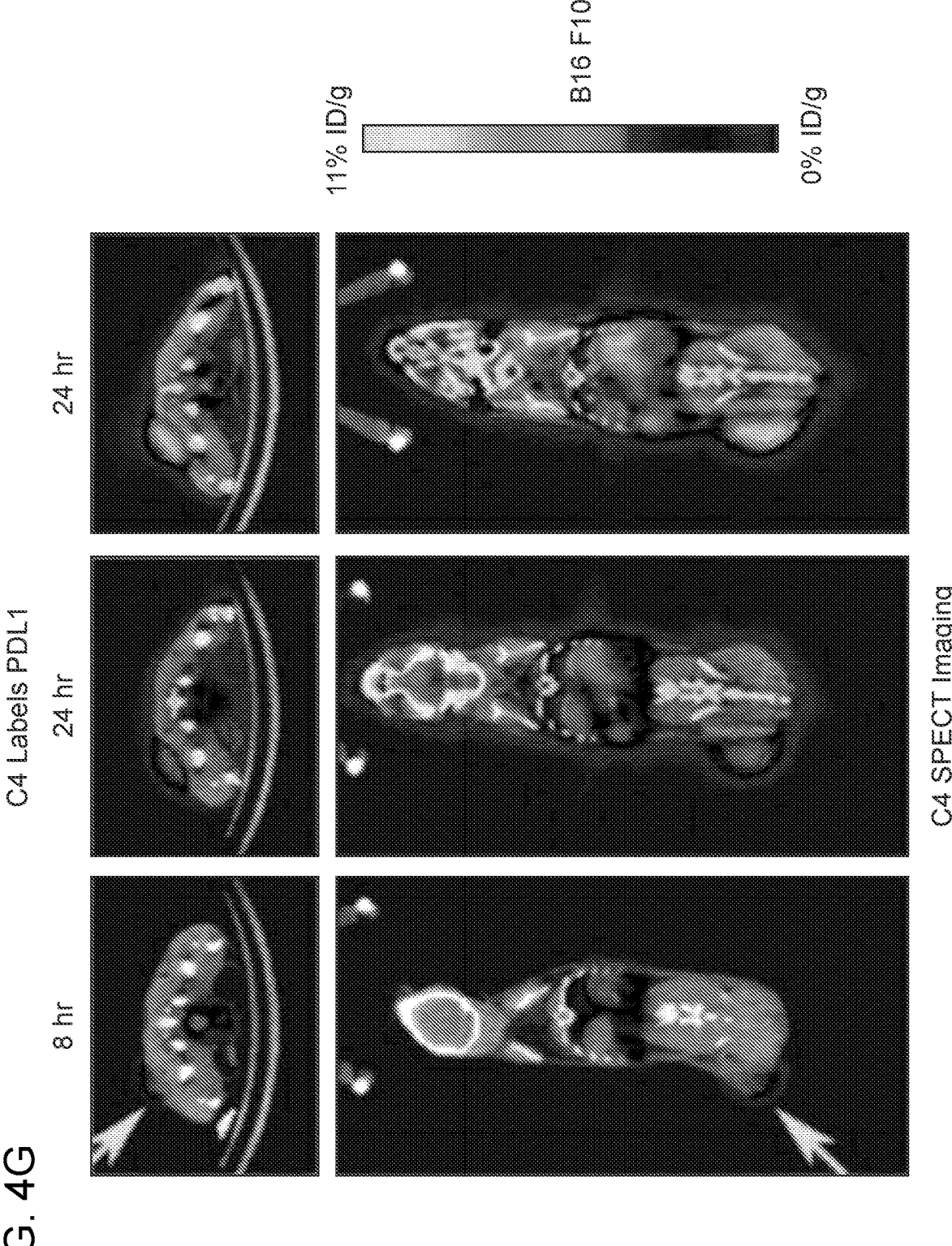

Integrated illumination: Fluorescence imaging requires illumination; however, penetration of near infrared light (NIR) is limited to ~5-10 mm in tissue due to absorption and scattering, precluding external illumination of tissue deep within the body. We solved this by illuminating cells from within the tissue through directly integrating micro laser diodes on chip: 300 µm (W)×250 µm (L)×100 µm (H) thin laser diodes (Rothiner LaserTechnik GmbH) producing 5 mW each are affixed along the chip edge (FIGS. 3A, 3B).

Figure 6A:
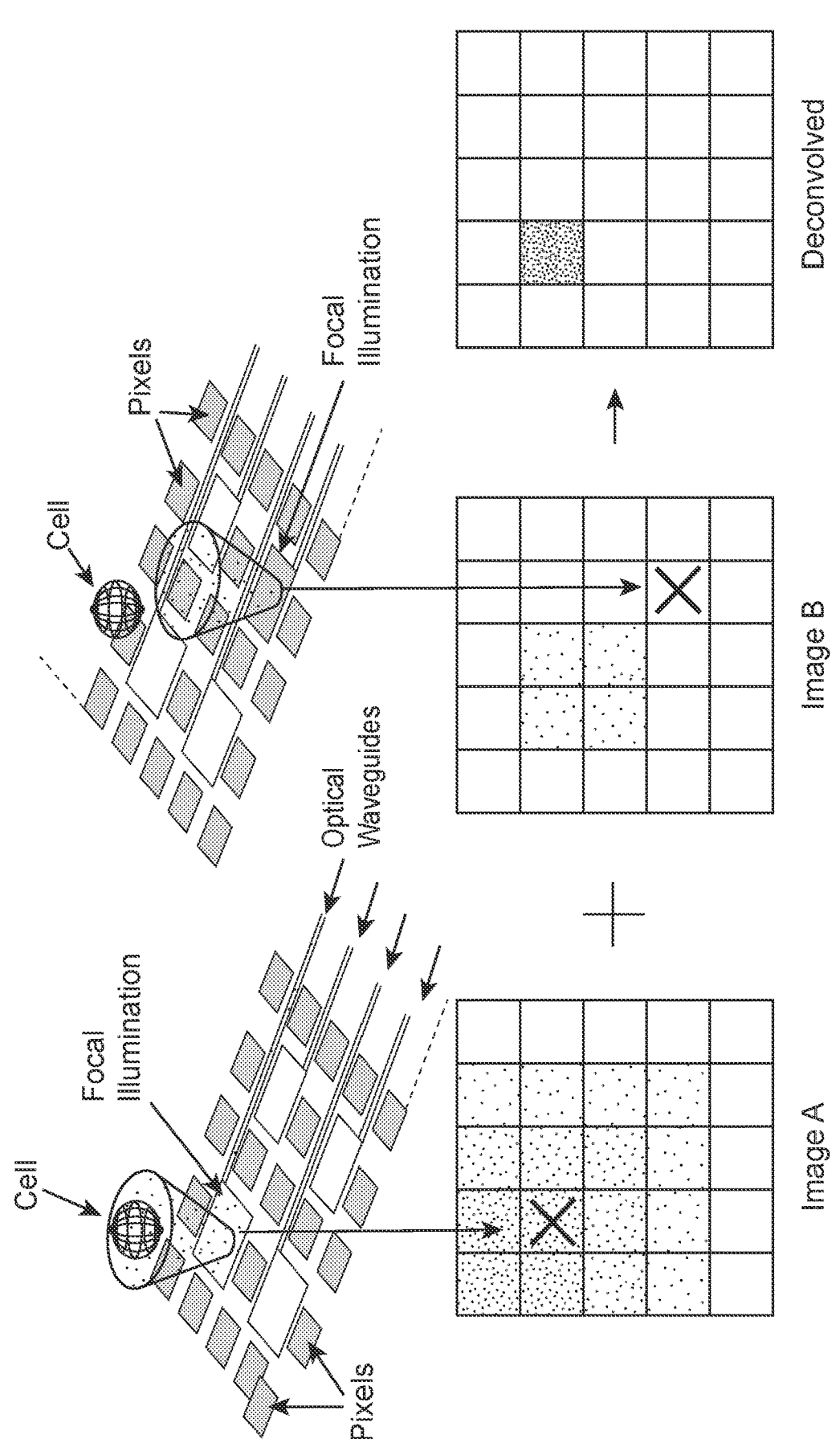
FIGS. 6A-6C.
Figure 6B:
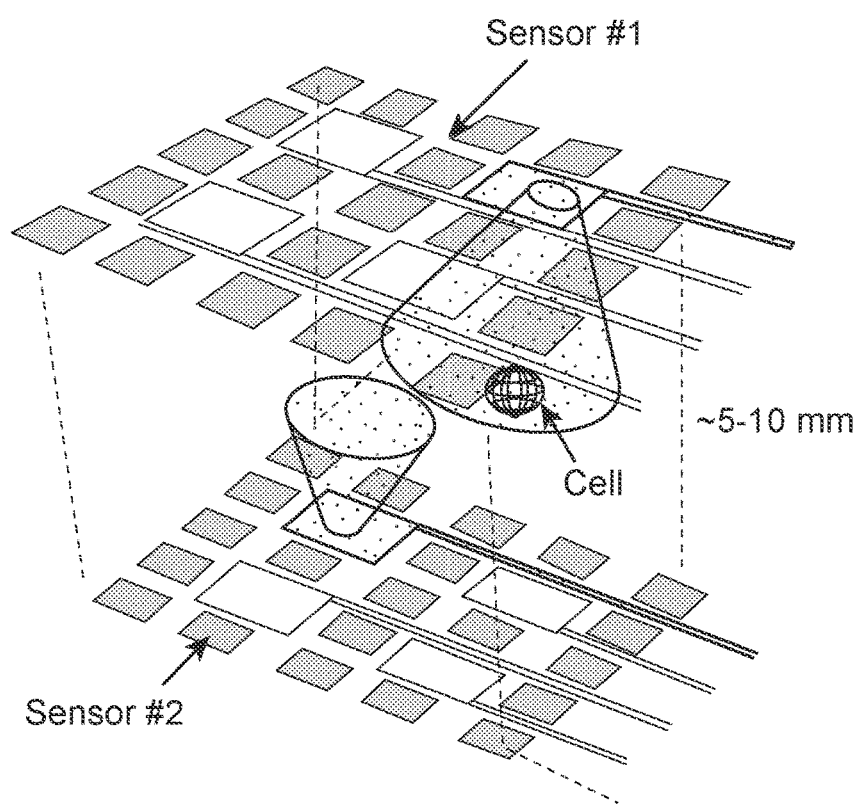
Figure 6C:
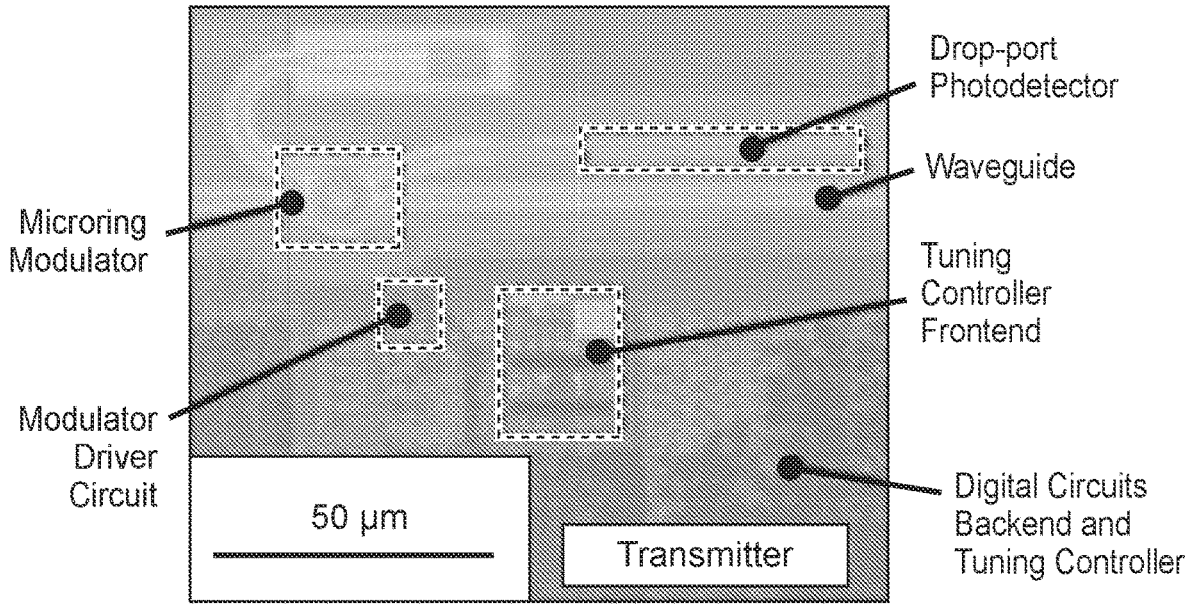

Deep Integration of Circuits and Nanophotonics Enables a Single, Monolithic Imaging Mote: Leveraging an unprecedented level of integration of electronics and photonics, made possible by the recent introduction of an advanced GlobalFoundries 45 nm SOI process semiconductor manufacturing process, we directly embedded illumination at the pixel level to achieve a higher spatial resolution using techniques similar to confocal microscopy. Image resolution is a product of both the pixel density and the spatial illumination patterns. Typically, illumination is uniform, and resolution is a purely a function of imaging optics and pixel density. Conversely, confocal microscopy uses a low-resolution imager, but precisely defines the illumination pattern, which then defines the spatial resolution. Here we combine these techniques, matching our pixel size with illumination patterns. With our current pixel size of 55 µm, our goal is illumination precision on this order, and pixel size can be readily reduced below this in modern CMOS processes. A microprocessor with integrated photonic I/O, featuring 70+ million transistors and thousands of photonic components on the same die was recently developed (12). Building on this and illustrating applicably to biosensors, we developed a chip-based molecular sensor using nanophotonic resonators (13) (FIG. 6C).

We routed photonic waveguides and grating couplers within the pixel array, allowing ultrafine control over illumination patterns at the pixel level. Sequential illumination (or in patterns) and imaging (as shown in FIG. 6A) enables a higher resolution image along the plane (X-Y) of the sensor to be resolved within tissue. While confocal imaging has been used to image in the sub-cellular regime for table-top microscopes, our goal is to enable cellular level (~10-100 micron) resolution in tissue, sufficient to monitor changes in immune cell concentration and distribution indicative of immune activation. These images can be "deconvolved" to gain improved spatial resolution To improve resolution in the ("Z") plane perpendicular to the sensor, opposing sensors were placed facing one-another with a spacing ~5 mm and imaged simultaneously. At 700-800 nm illumination, common to clinically used near infrared dyes, light penetrates ~5 mm (with 0.5% of light remaining), allowing the same cells to be imaged by both sensors, enabling reconstruction of a 3-D image (FIG. 6B).

Figure 2A:
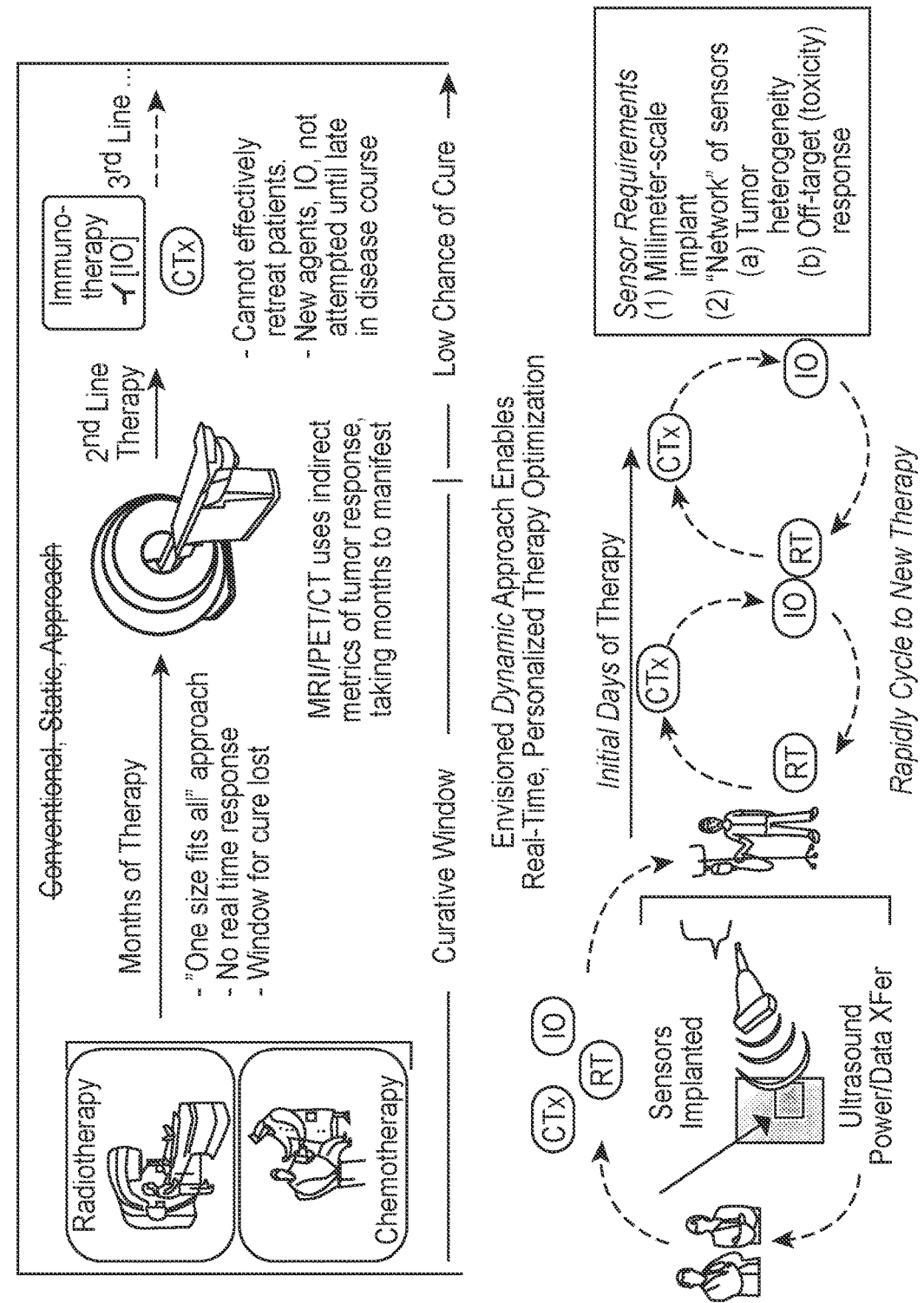
FIGS. 2A-2B. Envisioned Approach.
Figure 2B:
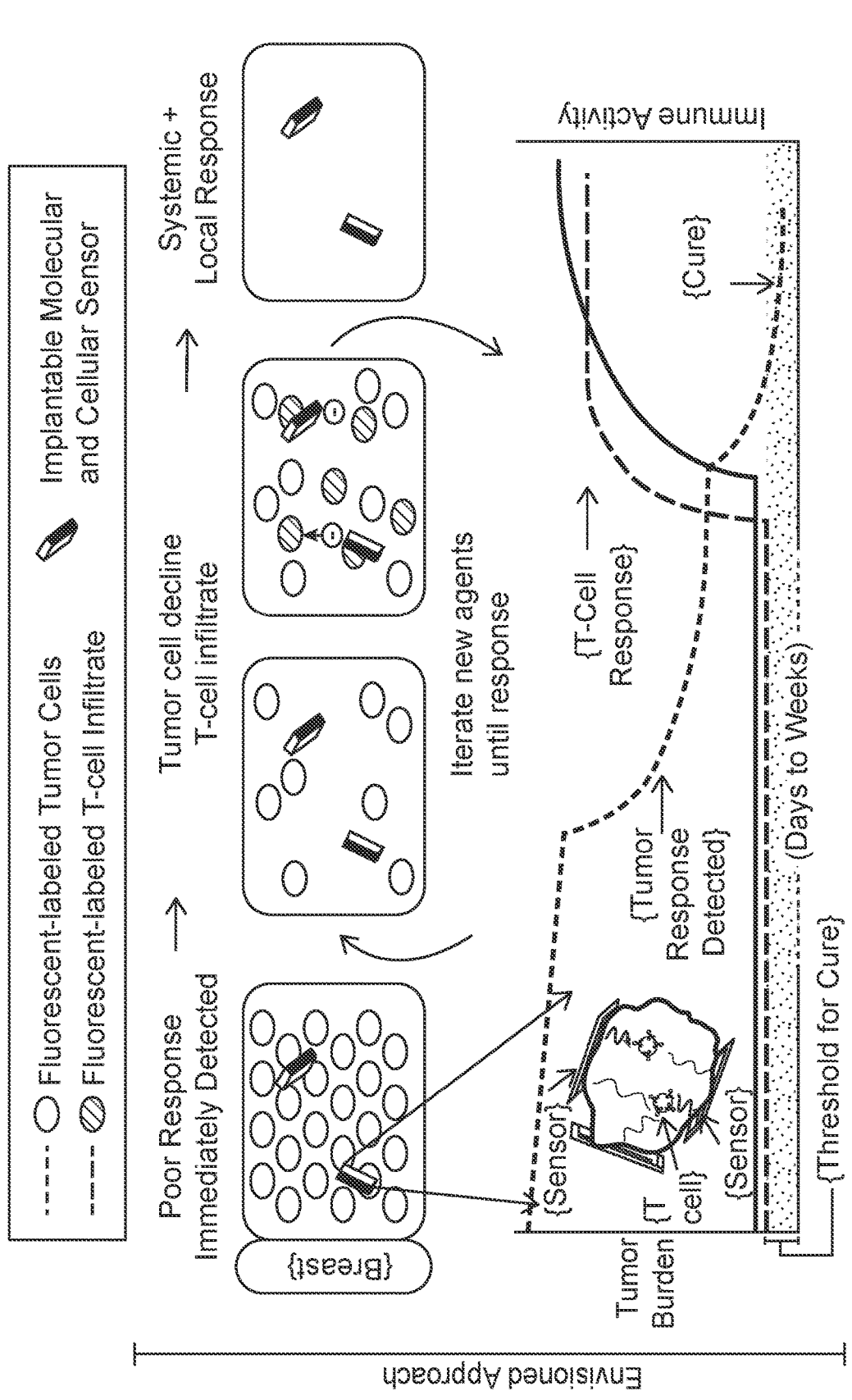

Imaging scarce photons with high sensitivity to identify small clusters of cells using our custom imager, with low-noise in-pixel amplification, capable of 20 cell-sensitivity in only 50 ms (8) using a scalable parallel imaging architecture. Starting with our custom 2,880-pixel prototype image sensor (8), with a scalable architecture made from integrated circuit (IC) technology, we design our sensor to be an ultrasensitive detector of photons (FIG. 2B). Each 55 µm pixel consists of a photodiode, converting an incident photon into an electronic signal, amplified by in-pixel circuitry. Our demonstrated low noise design approaches the shot-noise limit (8), representing the fundamental limits of optical detection. This effectively replaces a conventional camera with a single "chip". Currently, our platform successfully images cell clusters down to ~20 cells (1) (FIGS. 4A-4D) in 3D cell cultures, with signal degrading only slightly despite overlying blood and intervening tissue—addressing biofouling in vivo. We build on this platform, shrinking pixel size to $10^{-20}$ microns to improve spatial resolution while increasing photosensitivity using PIN diodes, which capture ~10× more light. On chip analog to digital converters (ADC) allow digital data to be transmitted, robust to tumor motion and signal degradation during transmission.

Our preliminary data demonstrates a functional chip-scale fluorescence imager in a 2.5×5×0.3 mm form-factor. Our imager design is scalable, and reducing pixel density and number eases constraints on power and data transfer. While we anticipate that only a single image is needed, if image quality is insufficient for cellular detection, multiple images can be averaged to improve SNR. Improvements in sensor design, such as fabrication in a photosensitive CMOS process increase detection efficiency 10×, decreasing integration time and the need for illumination power. NIR light penetrates several millimeters through tissue, ensuring that a "biofouling" layer will not interfere with imaging. Addressing possible interference by blood after implantation, our previous data (1) demonstrates successful imaging through blood made possible by the relatively low absorption and scattering of NIR light. Longer wavelength fluorophores can be used to improve tissue penetration of light in tissue, such as newer NIR-II dyes (28) with excitation at 840 nm, and emission at 1100 nm. Imaging chips can be fabricated with InGaAs photodiodes for detection of NIR light.

Multi-channel lens-free fluorescence imaging using microfabricated arrays of on-chip optical absorption filters. We achieve the performance of interference filters without the need for optical alignment by using the inherent physical band-gap of microfabricated compatible materials to design a high-rejection optical absorption filter. To expand the number of color channels we can image, we "tune" the filter by varying the thickness. Additional fluorophores (colors) are imaged by using materials with different band-gaps, for example gallium phosphide (2.25 eV band gap, 550 nm cutoff), cadmium selenide (1.74 eV, 710 nm cutoff), gallium arsenide (1.43 eV, 870 nm cutoff), indium phosphide (1.27 eV, 980 nm cutoff), and crystalline silicon (1.11 eV, 1100 nm cutoff).

Example 2

Integrating Bi-Directional Wireless Power and Communication for In Vivo Imaging

Figure 7:
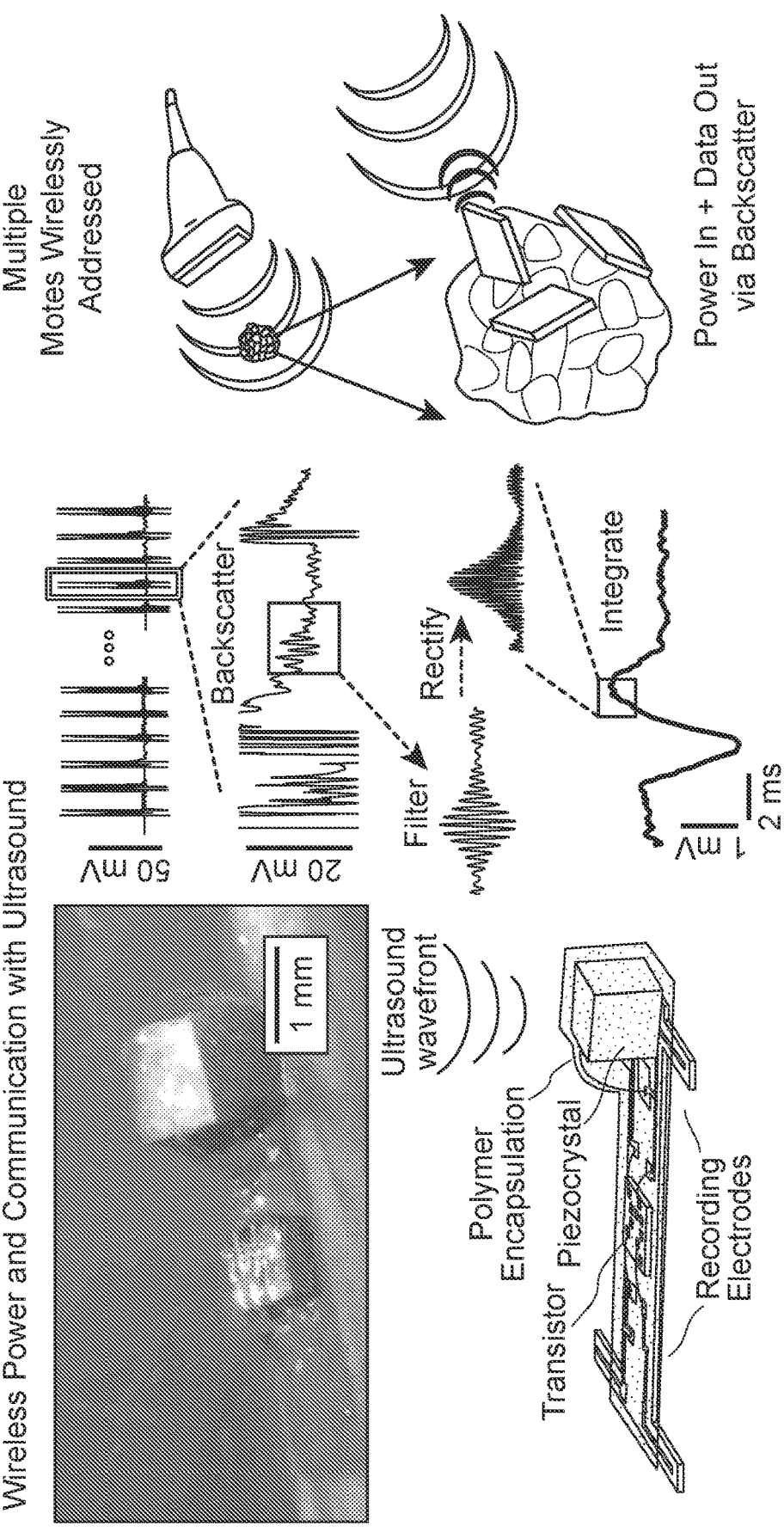
FIG. 7. Wireless power and communication via ultrasound through a mm piezoelectric. Wireless power transfer and communication via ultrasound shown in a neural stimulator (Seo et al. (2016) Neuron 91(3):529-539). Data is decoded from the backscattered ultrasound wave. (Right) Envisioned approach with multiple motes in the tumor.

The $mm^3$ chronic implants require simple and efficient wireless power and data transfer. Wireless power and data transfer via ultrasound is a well-established technique in engineering (14, 15) (FIG. 7), The relatively low loss of ultrasound in tissue allows efficient wireless power transfer, and data is simply received using backscatter. Previous efforts in implantable chip-based neural stimulators show data transmission rates of ~11-16.25 kByte/s (19) and power transfer rates of 200 μW at 10 cm deep in tissue (14).

Power Transfer: Ultrasound power is received using a piezo electric crystal wire-bonded to the chip. The resulting sinusoidal power supply is converted to several stable on chip power supplies (5 V for laser diode charging, and 1.8 V for chip function) using an active rectifier followed by a set of low dropout regulators. The chip clock is generated directly from the sinusoidal input. A piezoelectric crystal ~0.75×1×5 mm obtains ~2.5 mW of power via ultrasound, enough to power several micro-laser diodes, and chip operation. Power is stored on a 22 μF 0402 ceramic capacitor to power the laser diode and imaging array. We take advantage of the relatively long time course for intratumoral cellular changes (~minutes to hours), and design our sensor to have a 1s total imaging time, including power up (0.8s), imaging, and data transmission (0.2s). Illumination is the primary source of power consumption, and with a 5 mW optical power laser diode power output over a 1 $mm^2$ area, we achieve 500 mW/cm². At this power, we require only a 1-10 ms integration time, for a 1% duty cycle, dramatically reducing average power consumption. The 1-10 ms integration time is a conservative estimate based on our previous work: at 10 mW/cm² with integration time of 50100 ms, 20 cells are readily detected (1, 2). The imaging array is only on for the 1-10 ms integration time, and each pixel requires just 180 nW for operation, making average power consumption <100 μW. Pixel values are stored using a sample and hold within each pixel, until digitally converted during readout. For patterned illumination, this process is repeated serially with each unique illumination pattern (FIGS. 6A, 6B). We enable bi-directional communication to "upload" illumination patterns to the chip. In principle, this has been demonstrated with ultrasound before with neural stimulators, and quite common for radiofrequency (RF) communicators.

Data Transmission: Each pixel output is digitally converted on chip using an 8-bit converter and output using the standard method of modulating chip impedance for backscatter: a simple transistor across the leads of the piezoelectric terminal is shorted together, conveying a 'bit' (pulse) as in (15). For each pixel, with a time of flight being 66 μs for the ultrasound wave for a 5 cm implantation depth, backscattering takes $T_{tof}$ (66 μs)+8 bits×$T_{pulse}$(5 μs)=106 μs (150 ms total). 800 ms is used for charging external capacitors (a 22 μF 0402 ceramic capacitor) to power the laser diode and imaging array during the 1 ms image.

Multi-mote bidirectional communication: Communication with multiple implanted sensors can be handled with several strategies. We implement an identifier code for each chip, allowing chip-specific instructions to be transmitted. This allows the data from each chip to be independently acquired.

LEDs or laser diodes can be arrayed around the periphery to create an optical pattern. Power for illumination drives power consumption for this platform; we anticipate 800 ms to charge a 22 μF 0402 ceramic capacitor affixed to the imager, for a 110 ms pulse of light. If this is insufficient power transfer, a larger capacitor can be used (at the cost of increasing implant size), or more images can be serially taken and averaged, improving the image quality.

Illumination deep within the body using integrated silicon nanophotonics. On-chip micro-laser diodes are fully powered by wirelessly charging a capacitor and provide illumination in vivo deep within the body, at the point of imaging.

3-D image reconstruction using programmable illumination Deep integration of silicon nanophotonics and integrated circuits at the pixel level allows ultrafine control over illumination patterns. Using wireless communication, patterns for illumination are "uploaded" and images from all sensors are taken. The relative position of each sensor next to each other is assessed through a thin-cut CT.

Wireless bi-directional communication and power transfer enables a fully self-contained millimeter-scale wireless imager network by eliminating prohibitively large batteries and wires, which are impractical and a risk for infection. This enables a self-contained, perpetually functioning imager to exist indefinitely in multiple areas in the body. Using focused ultrasound and IDs coded into each chip, multiple sensors can be implanted and operated simultaneously, enabling small networks for imaging. This enables enhanced spatial resolution with multiple sensor motes, as well as imaging of off-target immune activity to predict impending toxicity. To obtain continuous images, a small self-contained ultrasound transducer can be affixed to the patient (for example on a belt on the abdomen), gathering data similar to a Holter monitor.

IgG formatted mAbs or minibodies are expressed in CHO cells and purified using protein IMAC to provide sufficient material for the studies. To produce anti-CD8 antibody, we use the commercially available antibody against CD8 (Cell Signaling, CD8a #D8A8Y). All other IgGs will be produced as previously described (21). Antibodies are conjugated to near IR fluorophores with extensive clinical data (IR700DX, IR800, LICOR Biosciences), facilitating clinical translation, as well as Alexa 660. Any antibodies that are not already human, such as 2G10 and C4, can be humanized.

Initially, we image cells ex vivo to establish imaging parameters, namely illumination intensity and integration time. To establish the ability to distinguish different cell types, we image 3D cultures consisting of cells (Table 1) labeled with corresponding antibodies conjugated to Alexa 660, IR700 and IR800 dyes, and compared with gold-standard microscopy, using our in vivo wireless fluorescence microscope with Implantable Nanophotonic Sensors for Immunoresponse in the Tumor microenvironment (INSITE), where each imaging chip images a single-color channel. Spectrally distinct channels are obtained using combinations of wavelength specific illumination, filters and fluorophores (Table 1). Next, we then used the multicolor filter as described above, and imaged each slide recording signal to background ratio, sensitivity and specificity as in (1) (FIG. 3) using gold-standard microscopy as a reference.

TABLE 1

| Antibodies and their molecular targets | | | | | | |
|---|---|---|---|---|---|---|
| Antibody | Clinical Setting | Target | Fluorophore | a-SI Filter | Illumination | Emission |
| C4 | Immunooncology | PDL1 | IR800 | 27 μm | 675 nm | >800 |
| 2G10 | Aggressive tumors (triple negative breast) | uPAR | IR700 | 15 μm | 633 nm | >700 |
| Anti-CD8 | Cytotoxic T Cell | CD8 | Alexa 660 | 5 μm | 532 nm | >650 |

Example 3

Multi-Color Imaging With In Vivo Antibody Labeling

Multi-cell in vivo sensing requires imaging multiple cell types directly within the tumor in real-time. To label tumor and immune cells, we require high affinity, high specificity fluorescently conjugated antibodies that will bind target cells presenting the epitope target and minimally bind to healthy tissue. We also have the opportunity to incorporate new tumor markers, to monitor both immune and tumor response. One candidate is targeting uPAR with the 2G10 antibody that competes against uPAR interaction with urokinase plasminogen activator and binds specifically to aggressive tumors such as triple negative breast cancer, pancreas cancer, and melanoma. Numerous recombinant antibodies for cancer research have been generated, including conformationally selective antibodies to the urokinase plasminogen activator receptor, uPAR (20), urokinase plasminogen activator, uPA, and most recently, PD-L1 (9), a candidate for translational use for in vivo. The antibodies were identified in a naïve Fab phage display library, generated from the spleens and peripheral blood lymphocytes of five human donors. The antibodies developed for uPAR, uPA, and PD-L1 were modified by coupling with radiolabels, chemical linkers and fluorescent tags for imaging. For example, the uPAR antibody 2G10 was used to image cancer cells in a mouse xenograft model of triple negative breast cancer (FIGS. 4E, 4F) using both fluorescence and SPECT/CT ($^{111}$In) imaging.

Next, we establish parameters for antibody injection. Antibody binding specificity in vivo can be quantified as tumor (or signal) to background ratio by tail vein injection of fluorescently conjugated antibodies, as we have done previously (22). We determine the optimum concentration for in vivo labeling by quantifying the target cell to background (muscle) ratio based on injecting mice with serially increasing concentrations [1, 10 μg, 50 μg and 100 μg] of each antibody-fluorophore conjugate. Biodistribution can be monitored using live animal imaging. Mice are sacrificed at 8, 24, 48, and 96 hours and tissues (tumor, kidney, liver, muscle) are harvested, fixed and imaged. Imaging of tumor tissue (and negative control) provides quantification of tumor (signal) to background ratio. These tissue samples are also imaged by our custom sensor ex vivo, allowing comparison of sensitivity of our custom imager to "gold-standard" microscopy. Our goal is to demonstrate cancer and immune cell localization (signal to background >2) using in vivo staining.

From "Cold" to "Hot": Rapid Iteration of Therapy to Activate the Immune System

Figure 8:
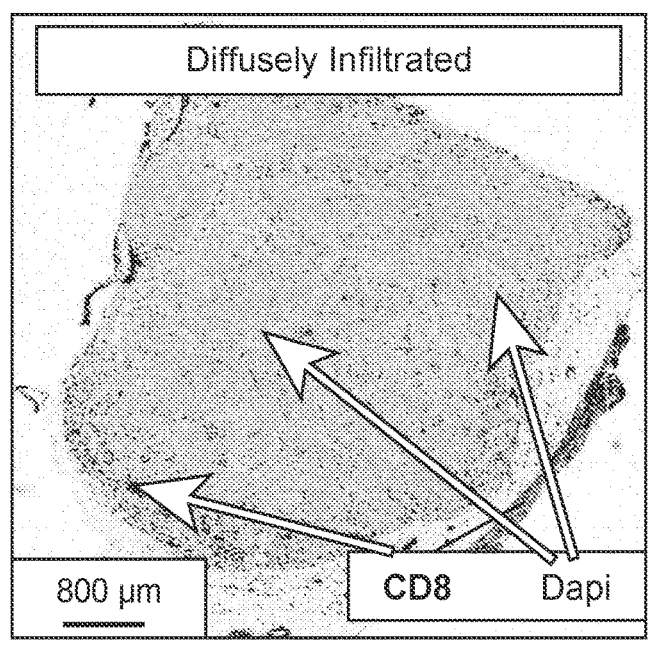
FIG. 8. Examples of patterns of CD8 infiltrate of Trp53 null mammary carcinomas that were classified as infiltrated, excluded, or deserts.
Figure 8:
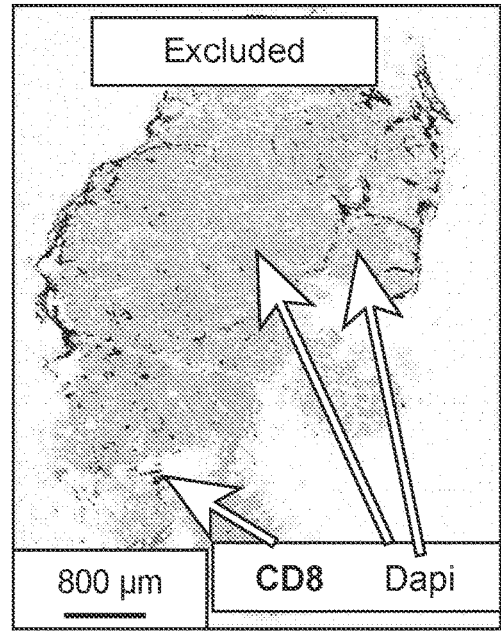
Figure 8:
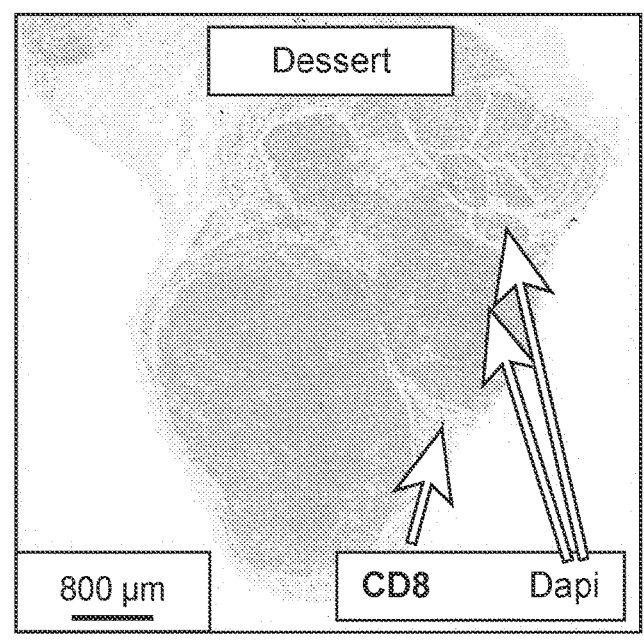
Figure 9:
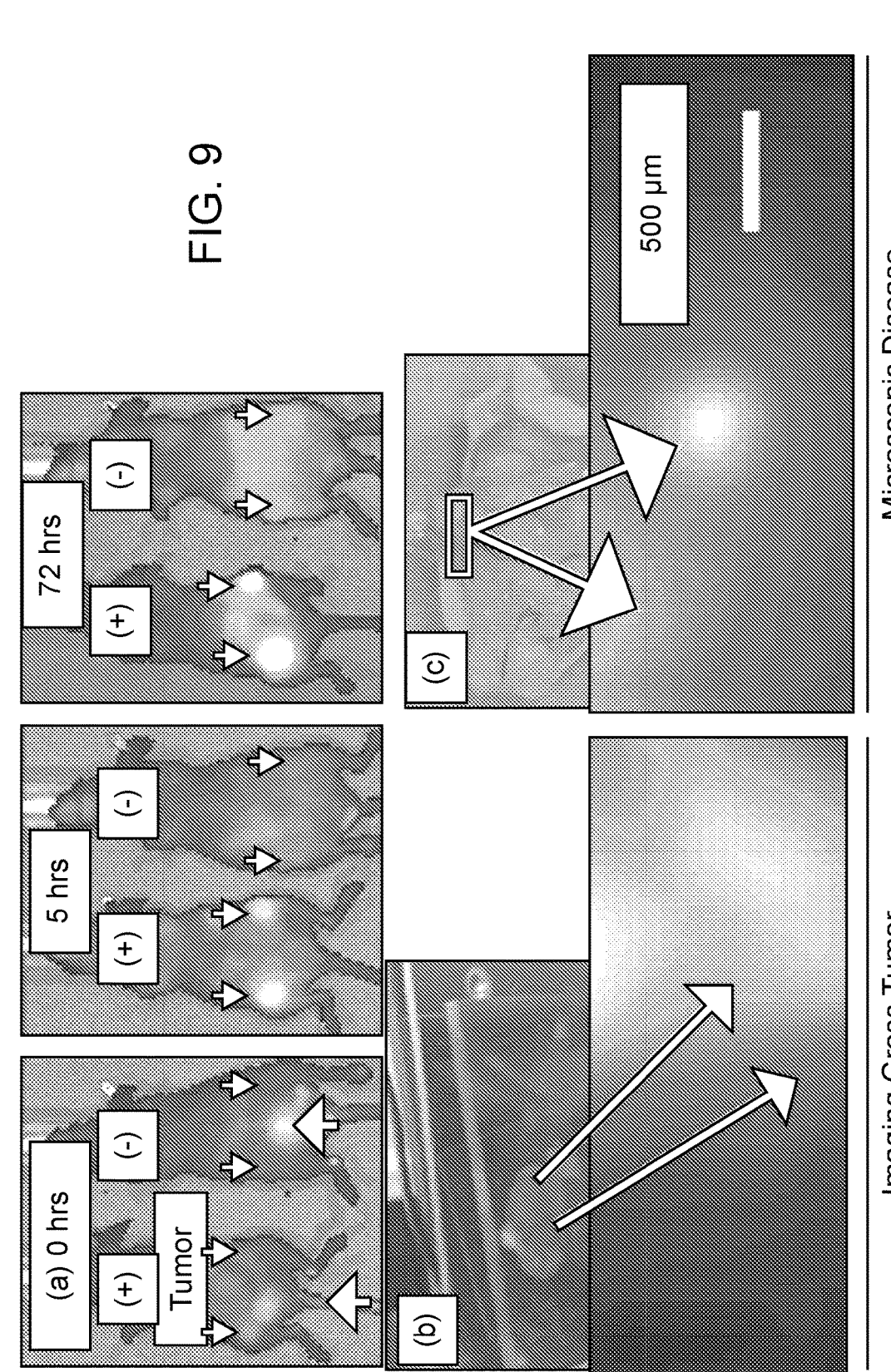
FIG. 9. In Vivo Imaging with Targeted Molecular Agents (a) Live imaging of a breast tumor model labeled with an antibody-IR700DX conjugate excited at 633 nm. (b,c) ex vivo tissue imaging placing the imager directly on fluorescently-labeled tumor tissue—recapitulating implantation.
Figure 10:
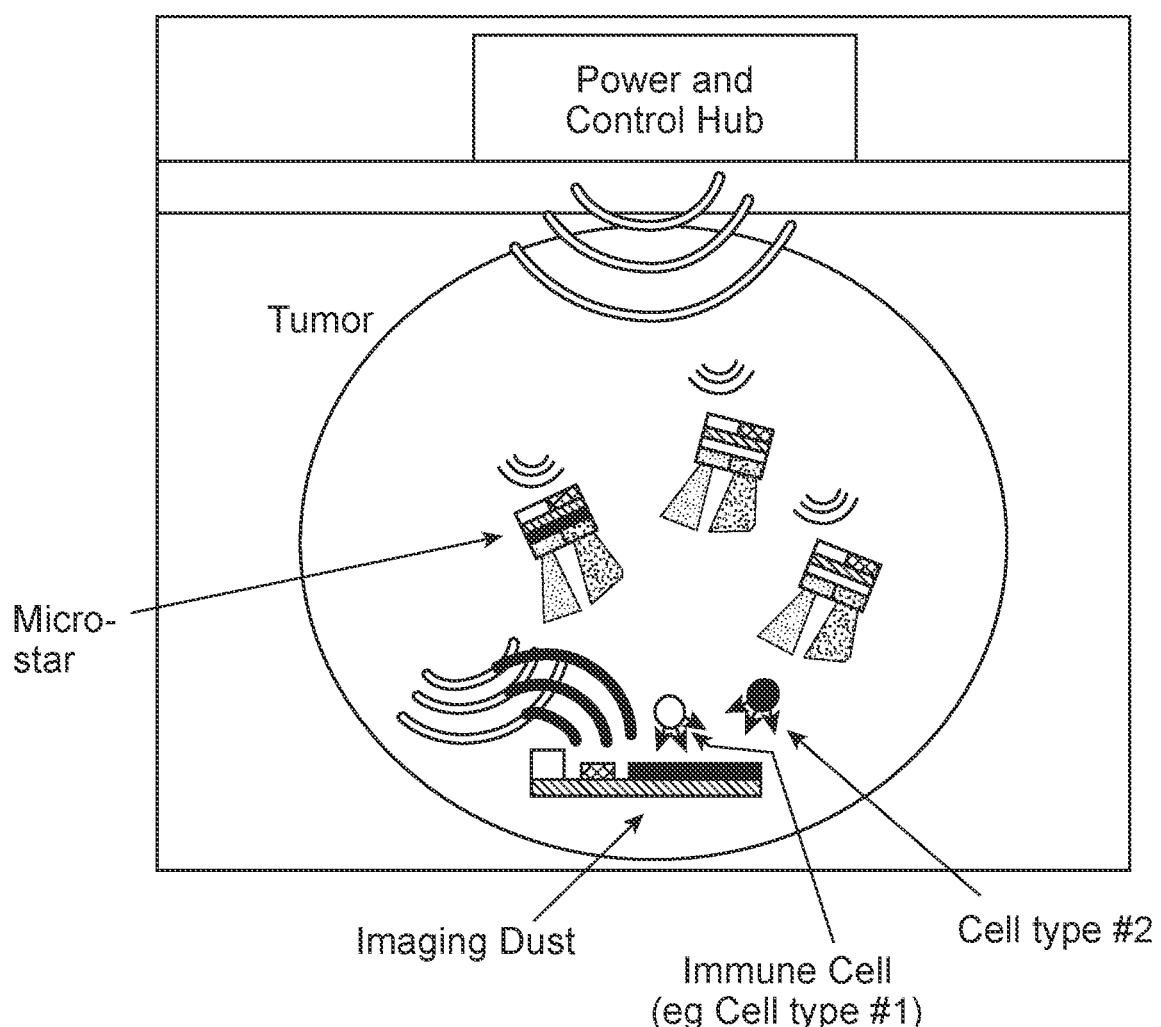
FIG. 10. Implantable imaging constellation with microstars featuring highly flexible structured illumination 3D imaging and multi-color/multi-cellular imaging.

We use INSITE to monitor the dynamic intratumoral evolution of the immune microenvironment in response to IO therapy and radiation. A key measure of efficacy of an immune response is detecting invasion of functional T cells into the tumor microenvironment (FIG. 8). Here we quantify T cell infiltrate (NTcells/mm$^3$) and tumor cell concentration (NTumor/mm$^3$) as a reference metric. From FIG. 8, and measuring a cell to be ~10 μm wide, we estimated 1-5% of cells are T-cells, and NTcells/mm$^3$=3-15×10$^4$ cells. Similarly, NTumor/mm$^3$=2×10$^6$ cells.

We use a syngeneic model of triple negative breast cancer, and implant INSITE into a subcutaneously grown tumor. Mice are initially injected with single antibody (from Table 1), and the response is monitored with INSITE. Images are acquired every hour for day 1, every 4 hours on day 2, and every 6 hours thereafter to capture both short- and long-term kinetics. One advantage of our system is the ability to continuously monitor, and assess subtle changes in the dynamic immune microenvironment; we will utilize our portable ultrasound transducer to enable continual image acquisition. Unbound labeling antibody is excreted within 48 hours, and at that time we administer pembrolizumab, 10 mg/kg IV. We quantify results by measuring the changes in infiltrating CD8 T-cells/unit volume, tumor response (uPAR), and immune activation (C4) as measured by change in fluorescence. To validate our findings, we excise tumors and the sensor en bloc, comparing histologic findings to imager findings, quantifying performance in terms of sensitivity and specificity.

Integrated response to radiation therapy (RT): RT plays a key role in many cancers and may act alone and/or in concert with other agents to activate the immune system converting a "cold" to "hot" tumor. RT has been shown to prime the immune response and alter the tumor microenvironment (TME) by increasing tumor immunogenicity, overcoming an immunosuppressive TME, and recruiting antigen-presenting and immune effector cells to the TME (25). For example, in melanoma, when anti-PD-L1 therapy was subsequently administered after irradiation, a synergistic effect on tumor regression was observed (26). The idea that cell death can act as an 'in situ vaccination' to stimulate immune response has motivated numerous clinical trials (27) including 150 active IO trials with radiation.

We use the Small Animal Radiation Research Platform (SARRP Surrey, UK), a system combining high-resolution CT imaging and accurate conformal beam therapy to target tumors in our mouse model. We implant a sensor, and measure T cell infiltrate (NTcells/mm$^3$), tumor burden (NTumor/mm$^3$), and PD-L1 expression (AU) at baseline, during and after RT (5 daily doses of 6 Gy, n=15 mice). Tumors are excised and examined for histological concordance with measured values.

First in vivo images within a deep tumor. We obtained real-time multicolor in vivo images deep within the body. Continuous streaming of images allows dynamic information on the migratory patterns. While resolution is degraded scattering in tissue, we are interested in the relative changes within a small volume surrounding the sensor with therapy, rather than the absolute cell count. Recognizing that imaging is confined to 5-10 mm from the sensor, tumor heterogeneity is addressed by placing multiple motes within the tumor.

References:
1. Papageorgiou E P et al. Biomed. Opt. Express. 9(8): 3607. (2018)
2. Papageorgiou E P et al. Opt. Lett. 43(3):354. (2018)
3. Hodi F S et al. N. Engl. J. Med. 363(8):711. (2010)
4. Nanda R et al. J. Clin. Oncol. 35(15_suppl):506. (2017)
5. Bindea G, Mlecnik B, Angell H K, Galon J. Oncoimmunology 3(1):e27456. (2014)
6. Gao X et al. Nat Biotech. 22(8):969. (2004)
7. Papageorgiou E P, Boser B E, Anwar M. An angle-selective cmos imager with on-chip micro-collimators for blur reduction in near-field cell imaging. (2016)
8. Papageorgiou E, Boser B, Anwar M. Chip-scale fluorescence imager for in vivo microscopic cancer detection. (2017)
9. Truillet C et al. Bioconjug. Chem. 29(1):96. (2018)
10. Fletcher D A et al. Applied Physics Letters. 77(14): 2109. (2000)
11. Ghosh K K et al. Nat. Methods. 8(10):871. (2011)
12. Sun C et al. Nature. 528(7583):534. (2015)
13. Adamopoulos C et al. Electronic-photonic platform for label-freebiophotonic sensing in advanced zero-change cmos-soi process. (2019)
14. Charthad J et al. IEEE Trans. Biomed. Circuits Syst. 12(2):257. (2018)
15. Seo D et al. Neuron. 91(3):529. (2016)
16. Anwar M, Aytur T, Matsudaira P. Appl. Phys. Lett. 94(11):111102. (2009)
17. Ameri A et al. A 114 ghz biosensor with integrated dielectrophoresis for single cell characterization. (2019)
18. Chien J-C et al. Lab Chip. (2018)
19. Biederman W et. al. IEEE J. Solid-State Circuits. 48(4):960. (2013)
20. LeBeau A M et al. Cancer Res. 73(7):2070. (2013)
21. Duriseti S et al. J. Biol. Chem. 285(35):26878. (2010)
22. Papageorgiou E et al. Imaging of ir700dx labeled mouse breast tumor using a customangle-selective fluorescence contact imaging system. (2018)
23. Vanpouille-Box C et al. Cancer Res. 75(11):2232. (2015)
24. Pai C-C S et al. Immunity. 50(2):477. (2019)
25. Ko E C, Formenti S C. Ther Adv Med Oncol. 10:1758835918768240. (2018)
26. Twyman-Saint Victor C et al. Nature. 520(7547):373. (2015)
27. Kang J, Demaria S, Formenti S. J. Immunother. Cancer. 4:51. (2016)
28. Antaris A L et al. Nat. Mater. 15(2):235. (2016)
29. LeBeau A M et al. Theranostics. 4(3):267. (2014)

Example 4

Towards an Implantable Fluorescence Image Sensor for Real-Time Monitoring of Immune Response in Cancer Therapy Introduction Fluorescence microscopy is instrumental for obtaining cellular-level information from inside the body. One key application is real-time visualization of tumor response to therapeutic procedures to help oncologists assess effectiveness of the therapy during the course of the treatment. This is particularly relevant for immunotherapy, a game-changing therapeutic which exploits the immune system to attack cancer [1], but it is only effective in less than 50% of the patients [2], [3], [4], [5]. For patients who do respond, the immune system is unleashed to fight previously incurable cancers, resulting in long-term, durable responses [6]. For those who do not respond, detailed cellular-level information is needed to identify non-responders early on—when the window for cure is still viable—in order to quickly pivot and assess the response to additional therapies.

To date, this can only be accomplished by a biopsy and microscopic evaluation which is impractical on a repeated basis. Moreover, current imaging modalities cannot reveal real-time multicellular changes at micron-scale, instead relying on centimeter-scale growth to detect a change. Due to the latency and low sensitivity of the state-of-the-art imaging systems, the curative window is lost before a critical change in the tumor size is registered [7].

While state-of-the-art chip-scale imagers provide high resolution for multicellular visualizations, they are not implantable inside the body [8]. The fluorescence imagers proposed in [9] and [10] require external wiring for power and data transfer; hence, such imagers are impractical to be utilized as stand-alone implants for long-term real-time monitoring. This has led us to propose an implantable fluorescence imager to implement a "wireless biopsy", leveraging new innovations in optics fused with advances in CMOS technology to personalize medication based on the individual response of the patients. Infiltration of the immune cells into the cancerous tissue and disease progression can be assessed by imaging the immune cells and the tumor labeled with fluorescently tagged biomarkers systemically injected in a host of clinical trials [11], [12]. Miniaturization of the implant to the size applicable to implantation via a core biopsy needle (millimeter-scale) imposes stringent limits on the dimensions of the imager. Therefore, in this proposed solution, bulky optics are eliminated to avoid any disruption for implantation and operation of the device [13]. To obviate the need for optical lenses, a fiber optic plate coupled with on-chip optical structures called angle-selective gratings (ASGs) are utilized to restrict the angle of incident light resulting in images with higher resolution [14]. The stand-alone operation of this system on a chip (SoC) miniaturized microscope relies on providing illumination with a mm-sized laser diode as well as wireless power and data transfer controlled by an external interrogator. Inspired by current medical implants, an ultrasonic link is utilized to leverage the low attenuation (~1 dB/cm/MHz) of acoustic waves in the tissue to enable efficient wireless power transmission and communication with a deeply seated imager implant [15], [16].

Here, we describe a fully contained proof-of-concept chip-scale imager interfacing with the biological world by detecting small clusters (<1 mm) of fluorescence-labeled cells in real-time and wireless transmission of the data to an external transducer. If deployed inside the body, local networks of implantable imagers can be incorporated for a variety of applications including resolving a 3D structure of the tumor and estimating the depth information from overlaid stacks of the cells. We further describe how the overall system powers up, captures an image from a fluorescent dye, Cyanine5.5-NHS (Cy5.5), and converts and transfers the data back to construct the image. Section II discusses system-level design challenges and the corresponding solutions. Section III entails proof-of-concept experimental results of imaging a resolution target with the fluorescent dye, and Section IV concludes the work.

II. Implantable Imaging System

Figure 21:
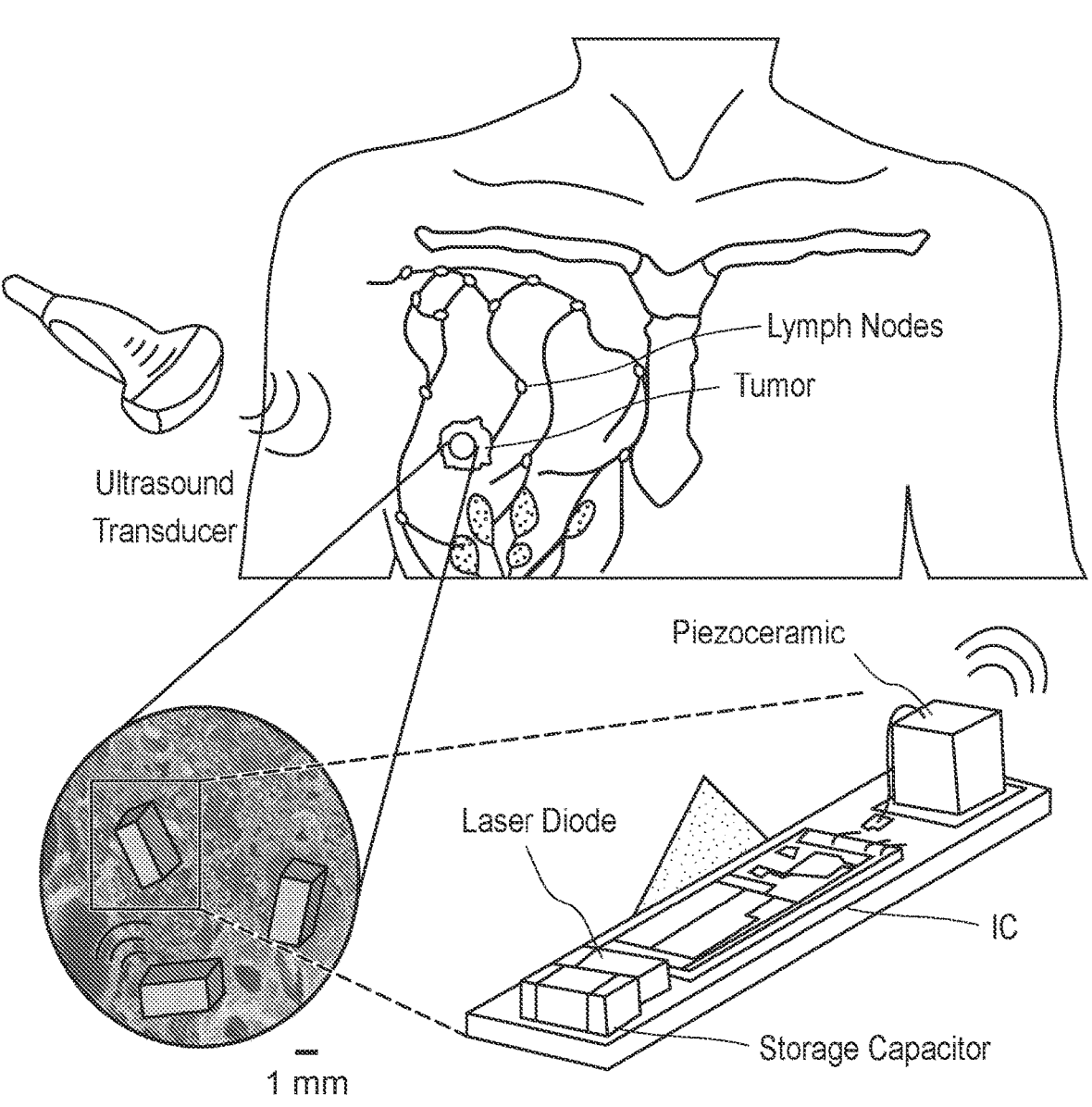
FIG. 21. Concept of an implantable fluorescence imaging system (piezoceramic, imager IC, laser diode and storage capacitor) communicating with an ultrasound transducer.

Design of a self-contained implant for fluorescence microscopy relies on integration of the power and data transceiver, the optical illumination source (as light cannot penetrate from an external source deep into the body) and the CMOS imager array. As shown in FIG. 21, the implant consists of: (1) a piezoceramic to harvest power (from acoustic waves launched by a distant external interrogator) and wireless transmission of data through an ultrasound (US) link, (2) the imager IC fused with ASG filters to capture the optical signal generated by (3) the mm-sized laser diode and (4) a storage capacitor. The device can be implanted using core biopsy needles, similar to gold-seed fiducial implants used to mark tumors for radiotherapy [17]. This section describes in detail the strategies to address design challenges for each component and the full system.

A. Fluorescence Microscopy

Prior to imaging, the cells are labeled with fluorophores engineered to conjugate with antibodies specifically targeting the cells of interest. Once bound to the target, the fluorophores are excited by the excitation light resulting in emission of a longer-wavelength light after a Stokes shift [18]. The emitted light is filtered by an optical bandpass filter and is captured by the CMOS sensor. The received fluorescence signal from a cell is computed as follows:

$$F = \sigma Q P_{in} N, \tag{1}$$

where $\sigma$ the fluorophore absorption cross section in $cm^2$, Q is the fluorescence quantum yield, $P_{in}$ is the incident light flux in $W/cm^2$, and N is the number of fluorophores attached to the cell [19]. A typical Cyanine5.5-NHS dye that can be excited by a 635 nm laser diode, has quantum yield and fluorophore absorption cross section equal to 20% and $10^{-16}$ $cm^2$, respectively [20], [21]; therefore, an optical input power close to 30 $mW/cm^2$ is needed to generate a 200 fW signal that can be detected by the sensor [13].

B. Optical Source

As shown in (1), inefficiency of fluorophores in emitting the received optical power, due to their small absorption cross-section, determines the required optical power for the excitation source to maintain high sensitivity while detecting small clusters of cell foci.

A 635 nm edge-emitting laser diode provides an excitation power close to 30 $mW/cm^2$ at its nominal operating point. A Stokes-shifted longer wavelength photon at 710 nm is emitted, and detected by the imager. A bandpass interference filter (ET 710/55 nm, Chroma) rejects any input light with wavelengths shorter than 682 nm including the excitation light by 60 dB. A 500 μm-thick quartz wafer with a wavelength selective coating is epoxied on top of the chip. To achieve the required incident optical flux, the laser diode is operated with a nominal voltage and current of 2.2 V and 33 mA as shown in FIG. 24B.

Figure 22A:
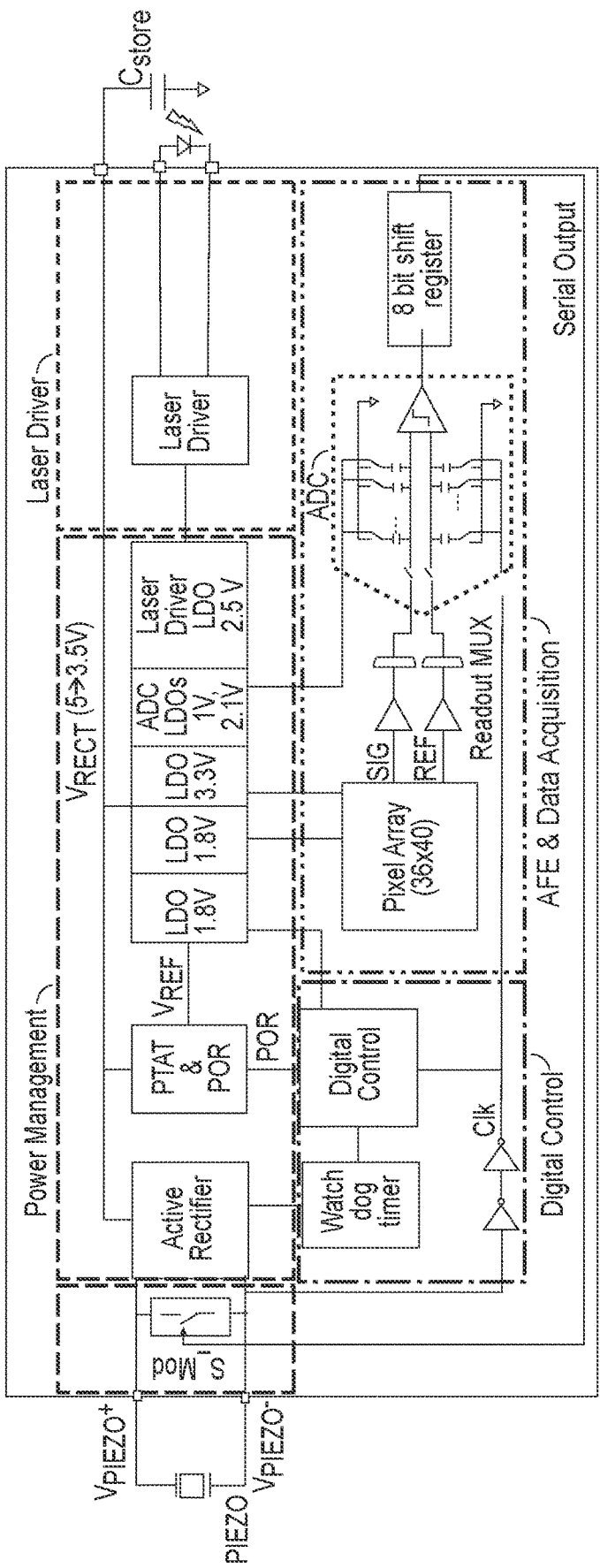
FIGS. 22A-22C.
Figures 22B, 22C:
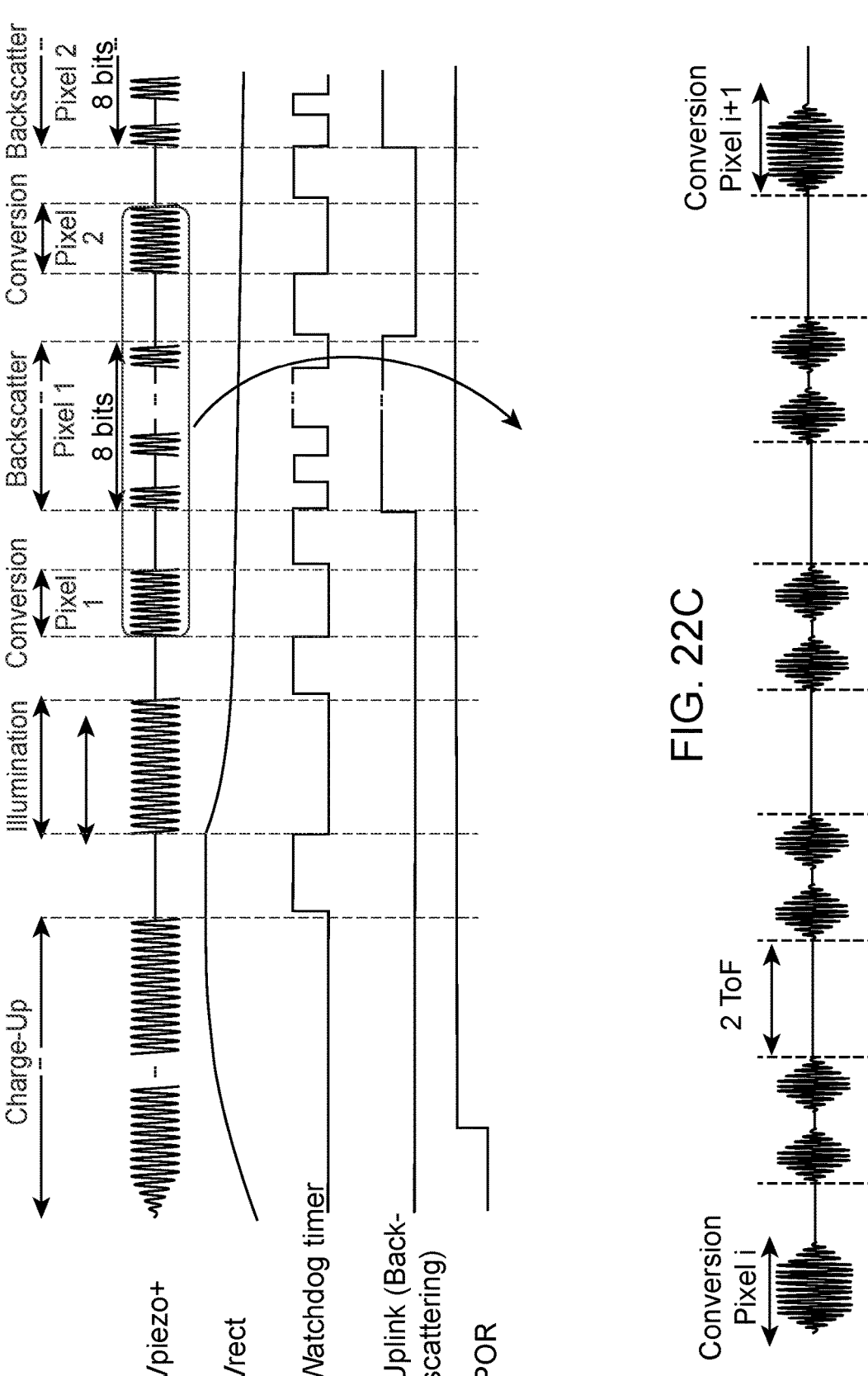

FIG. 22A shows the block diagram of our implantable imager, consisting of 4 main blocks: the pixel array, power management unit, laser driver and the Finite State Machine (FSM) for digital control. The chip measuring 2.4 mm by 4.7 mm was fabricated in a standard 0.18 μm 1.8 V/5 V/32 V process. Detailed design of the pixel array is presented in Papageorgiou et al. ("Chip-Scale Angle-Selective Imager for In Vivo Microscopic Cancer Detection," IEEE Transactions on Biomedical Circuits and Systems, vol. 14, no. 1, pp. 91-103, 2020; herein incorporated by reference in its entirety). The photodiode current for each pixel in the 36×40 array is integrated on the feedback capacitor of the capacitive transimpedance amplifiers (CTIAs). The output voltage is sampled twice at the beginning and end of the integration time generating reference and signal values respectively. This correlated double sampling (CDS) scheme suppresses offset and low frequency noise. Provided typical values described in Section II.A, 8 integration times ranging from 16 ms to 128 ms in steps of 16 ms can be hard-coded for each device. Signal and reference voltages of each pixel are read sequentially, subtracted, and converted to a digital signal using a differential 8-bit SAR ADC. The serialized data is backscattered wirelessly using an on-off keying (OOK) modulation scheme to sustain robustness while transferring 11.5 kbit/frame of image data that will be discussed in the next section. The power management unit rectifies the input AC waveform to a 5 V DC voltage to supply the entire SoC. Various on-chip low-dropout voltage regulators (LDOs) regulate the supply voltage (1 V, 1.8 V, 2.1 V, 2.5 V, 3.3 V) for the imager, the FSM, the laser driver and the ADC. The harvested energy is stored on a 1.4 mF off-chip storage capacitor during US power transfer to get utilized during illumination of the laser diode. The laser driver generates a 50 kHz, 50% duty-cycled pulsed current of 33 mA only during the integration interval. The supply voltage of the laser driver is regulated to 2.5 V to refrain from damaging the laser diode. A dedicated FSM controls cooperation of the imager with the laser driver and is synchronized with a clock signal extracted from the AC signal. FIG. 22B depicts timing diagram and state transitions of the chip. The operation of the chip is broken down into 4 states: Charge-Up, Illumination, ADC Operation and Back-scattering Modulation. A watchdog signal (triggered in the absence of US pulses) keeps track of the state transitions and data transfer [15]. As noted in Section II.B, power consumption of the implant is dominated by the laser diode. To accommodate the electrical power of 36.3 mW for the laser diode (72.6 mW nominal electrical power with a 50% duty cycle) during illumination, a 1.4 mF storage capacitor is chosen to store charge during power-up. The chip starts harvesting power upon arrival of the incident US input and remains in charge-up state until the rectified voltage (Vrect) reaches 5 V. After the LDO voltages are established, a power-on reset (POR) signal initializes the digital control. During the charge-up state, the pixel array is turned off to speed up the initial charging period. Followed by the illumination state, the first transition of the watchdog signal is indicative of the end of the charge-up period. During illumination, the diode turns on while the photodiode current starts getting integrated for each pixel and then sampled at the end of the state for subsequent data conversion and backscattering. Power-intensive blocks including the buffers preceding the ADC, the pixel array and the laser driver are duty-cycled off when not being used during data uplink. Despite the considerable droop of Vrect during illumination, the LDOs are designed to operate with input voltages as low as 3.5 V to ensure functionality of the device for the subsequent states. Each pixel's voltage is converted and wirelessly transmitted by modulating the impedance of the same piezoceramic used for power transfer until the watchdog timer counts for the entire 36×40 pixels. The data transfer protocol is discussed in the next part.

D. Wireless Power and Data Transfer Protocols

For low tissue attenuation of acoustic waves while operating in depth inside the body, an US link minimizes the size of the implant and the charge-up period by providing higher power transfer density compared to EM waves and optical links [22], [23]. Maintaining a small form-factor for the implant necessitates having a single-element piezoceramic for both power harvesting and data back-telemetry. Capturing a high-resolution image requires transferring 11.5 kbits (34×40=1440 pixels, 8-bit per pixel) per frame. A pulsed-echo OOK modulation scheme is implemented to separate power and data transfer in time domain while using a single piezoceramic for both. A robust backscattering scheme is implemented as shown in FIG. 22C, where each 8-bit packet is divided into sets of 2 bits fit within the 26.7 us roundtrip (2ToF, time-of-flight) of US waves for a depth of 2 cm. Wireless transmission of a single bit by means of OOK-modulated ultrasound backscattering requires modulation of the termination impedance of the piezo, $R_{Load}$. At the series resonance frequency, fs, the normalized backscattered echo amplitude is proportional to $R_{Load}/(R_{Load}+R_{piezo})$, where $R_{piezo}$ is the internal resistance of the piezo at fs [24].

Therefore, a modulation switch, S_Mod in FIG. 22A, is used to modulate $R_{Load}$ and ultimately the echo amplitude for OOK modulation.

III. Experimental Results

In this section a proof-of-concept demonstration of the operation of the SoC with a sinusoidal input signal, amplitude modulated (AM) by an FPGA (Xilinx Spartan-6 LX45) is presented. Input frequency and equivalent impedance of the AC source are chosen to replicate the resonance frequency and electrical impedance of a 1.5×1.5×1.5 mm$^3$ piezoceramic (Lead Zirconate Titanate, PZT) measured in canola oil (~0.25 dB/cm attenuation at 1 MHz). The 1 MHz AC signal is applied as an input voltage source with a series resistance of 2 kΩ to electrically model the piezoceramic. Each IC block is characterized separately, and functionality of the entire system is verified by imaging a fluorescent dye Cyanine5.5-NHS, distributed over a resolution test target providing a fine spatial structure to evaluate the image resolution.

A. State Transitions

Figure 23:
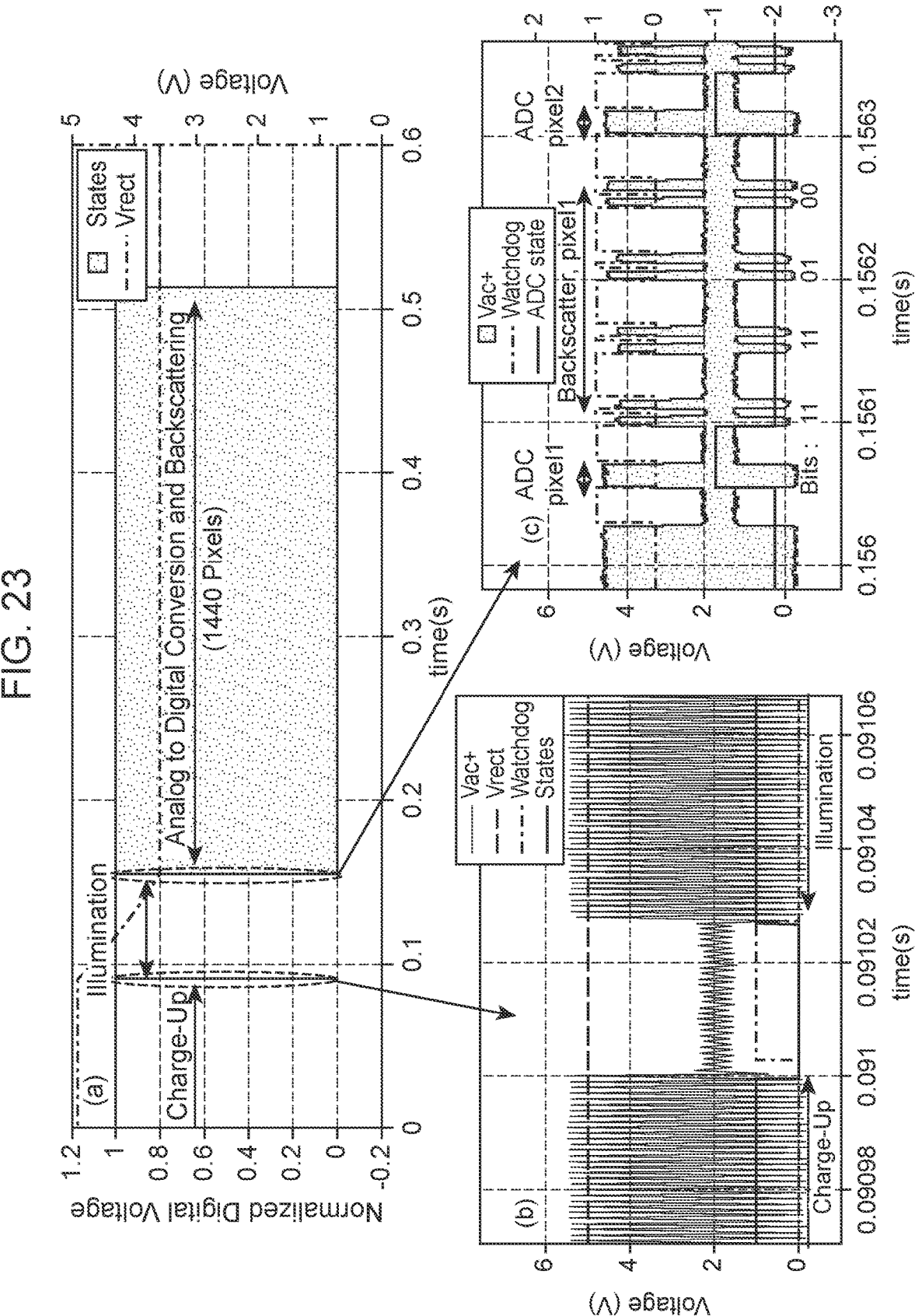
FIG. 23. Measured state transitions (a) FPGA control signal for AM Modulation of the AC source (b) Charge-Up (only the last 90 ms is shown) and Illumination states (c) Analog to digital conversion and backscattering states.

The required charge-up time for the storage capacitor is characterized by varying the interval the AC signal is applied during the initial state. For a 1.4 mF storage capacitor, Vrect reaches 5 V after 20 s, which enables capturing minute-scale movements of cells inside the tissue environment [25]. State transitions of the IC for a 20 s charge-up, 64 ms illumination and 13.5 us ToF (27 us round-trip interval) are shown in FIG. 23. A digital state control signal from the FPGA modulates the AC signal. FIG. 23 shows the AC input signal and the output of the watchdog timer for a complete set of Charge-Up, Illumination, ADC conversion and Backscattering states. As depicted in FIG. 23C, the AC signal is modulated by the serialized output of the ADC with a modulation depth of 91%. The amplitude modulated AC signal in FIG. 23C corresponds to the digitized value of 8'b11110100 for the first pixel with MSB being the first transmitted bit.

B. Optical Power

Figure 24A:
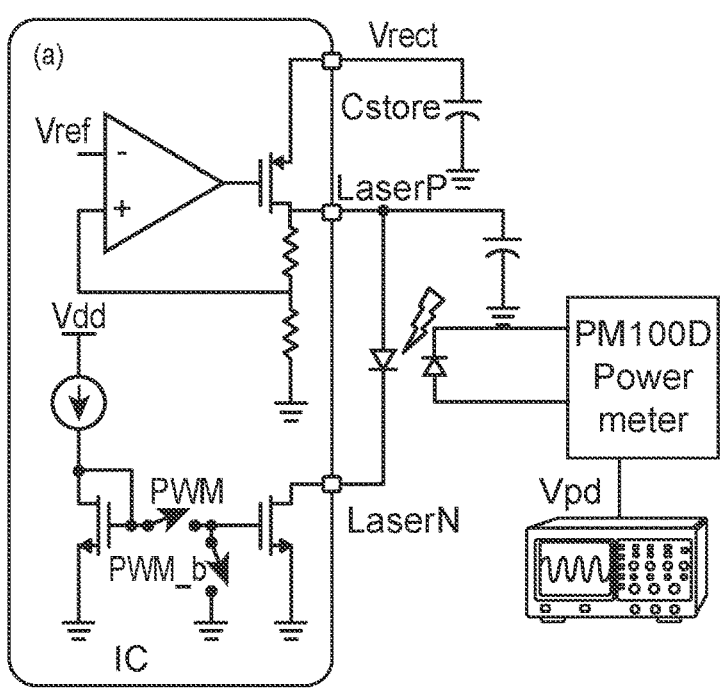
FIGS. 24A-24C.
Figure 24B:
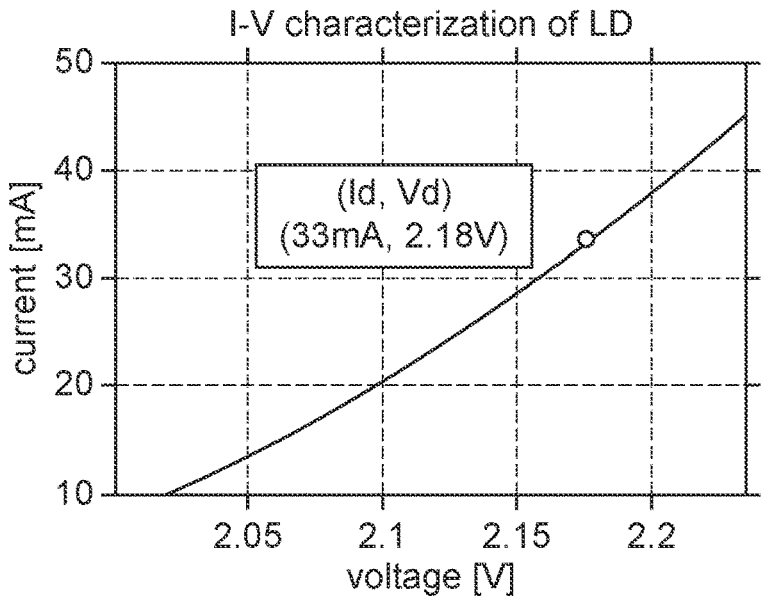
Figure 24C:
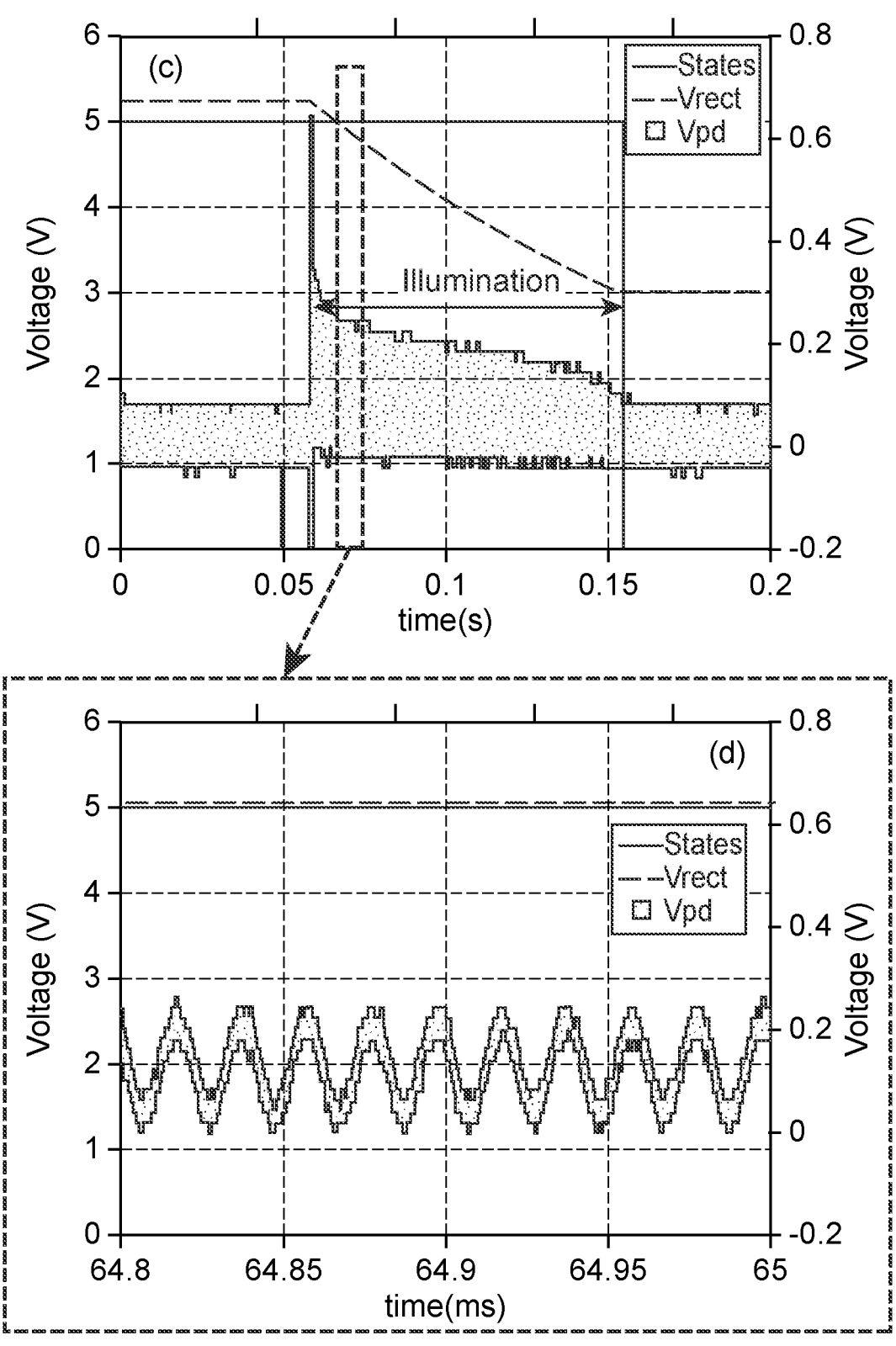

FIG. 24A shows the setup to verify performance of the laser driver. The output optical power of the laser diode is measured using the photodiode voltage output of a power meter (PM100D, Thorlabs) which is proportional to the detected optical power. As shown in FIG. 24D the photodiode voltage (Vpd) is a 50 kHz, 50% duty-cycled signal tracking the current applied to the laser diode. Using PIV characterization of the photodiode, the measured laser diode current varies from 33.5 mA to 29 mA corresponding to optical powers of 2.1 mW to 0.9 mW respectively. The 13% current drop stems from the droop in Vrect throughout the illumination state, which can be improved by using a larger storage capacitor.

C. Imaging Setup

Figure 25:
FIG. 25. Imager IC with the optical filter, dark epoxy for optical isolation, laser diode mounted and wire-bonded imaging setup for Cy5.5 distributed over the USAF target diagram of the imaging setup.

FIG. 25 shows the experimental setup for imaging the fluorescent dye on a resolution target. The Chroma ET 710/55 nm bandpass filter is epoxied on top of the chip and black epoxy is applied on the wire-bonds covering all sides to avoid any bleed-through from ambient light and the excitation source as shown in FIG. 25A. The laser diode is epoxied and wire-bonded to a separate board and connected to output pads of the laser driver in FIG. 25B. Cyanine5.5-NHS Dye is applied on a coverslip on a USAF 1951 Resolution Target. Each image is captured, converted and streamed out in real-time after a 20 s charge-up interval.

D. Imaging Fluorescent Dyes

Figure 26:
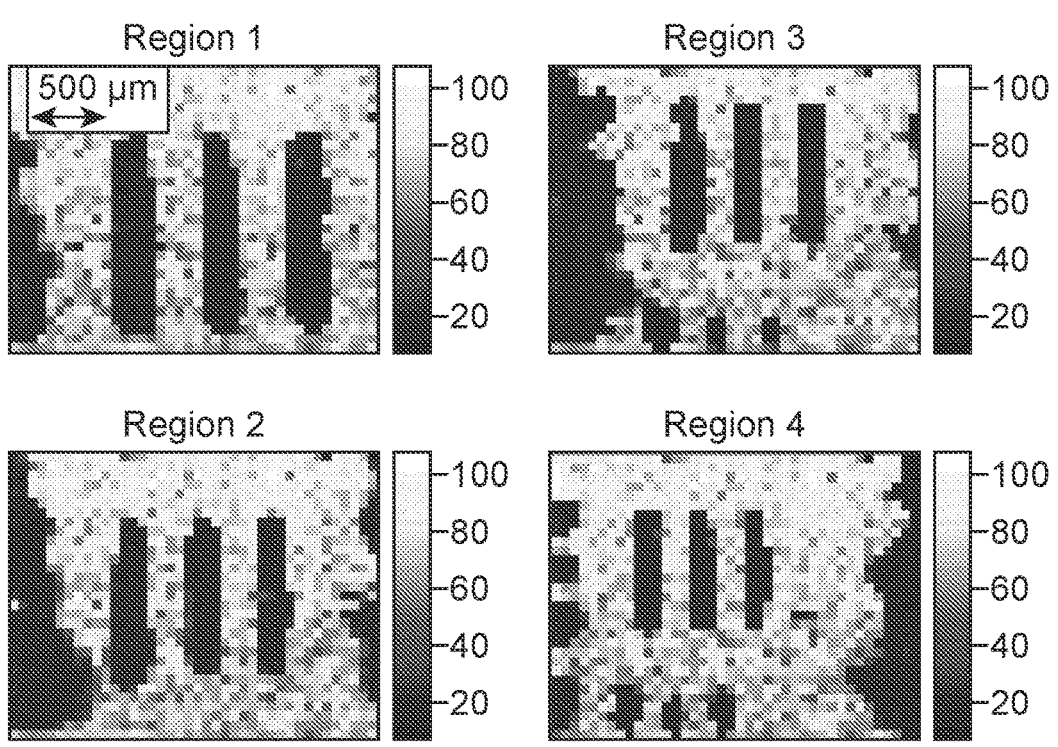
FIG. 26. At top, images are shown from the Cy5.5 dye on 4 regions of the USAF target (pixel values are shown in ADC codes). At bottom is shown the USAF target with coverslip and the corresponding 4 regions.
Figure 26:
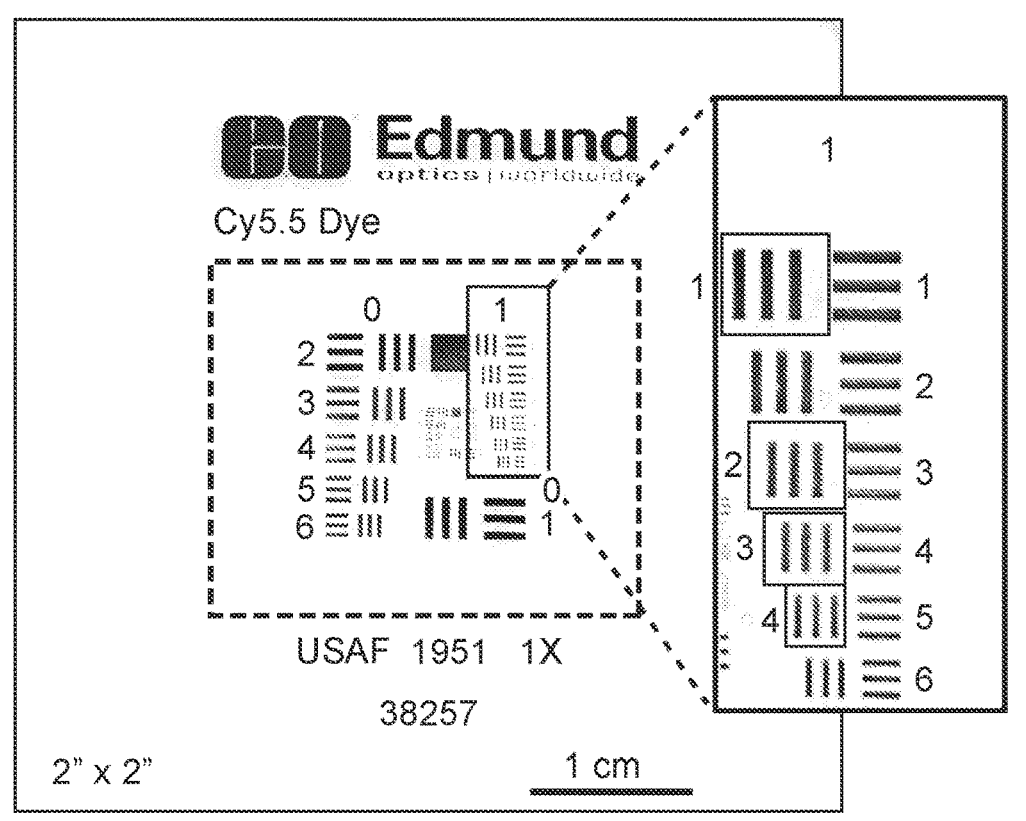
Figure 27:
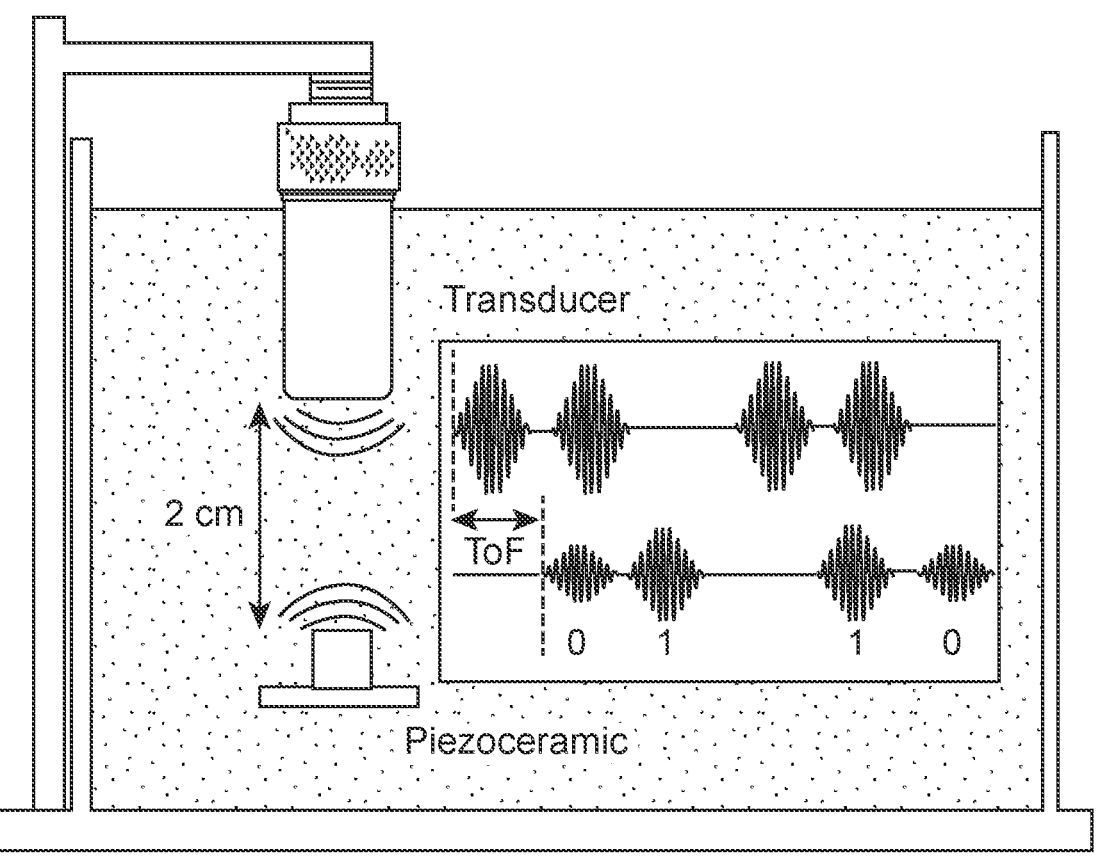
FIG. 27. Ultrasound technology for power and data transfer.
Figure 28:
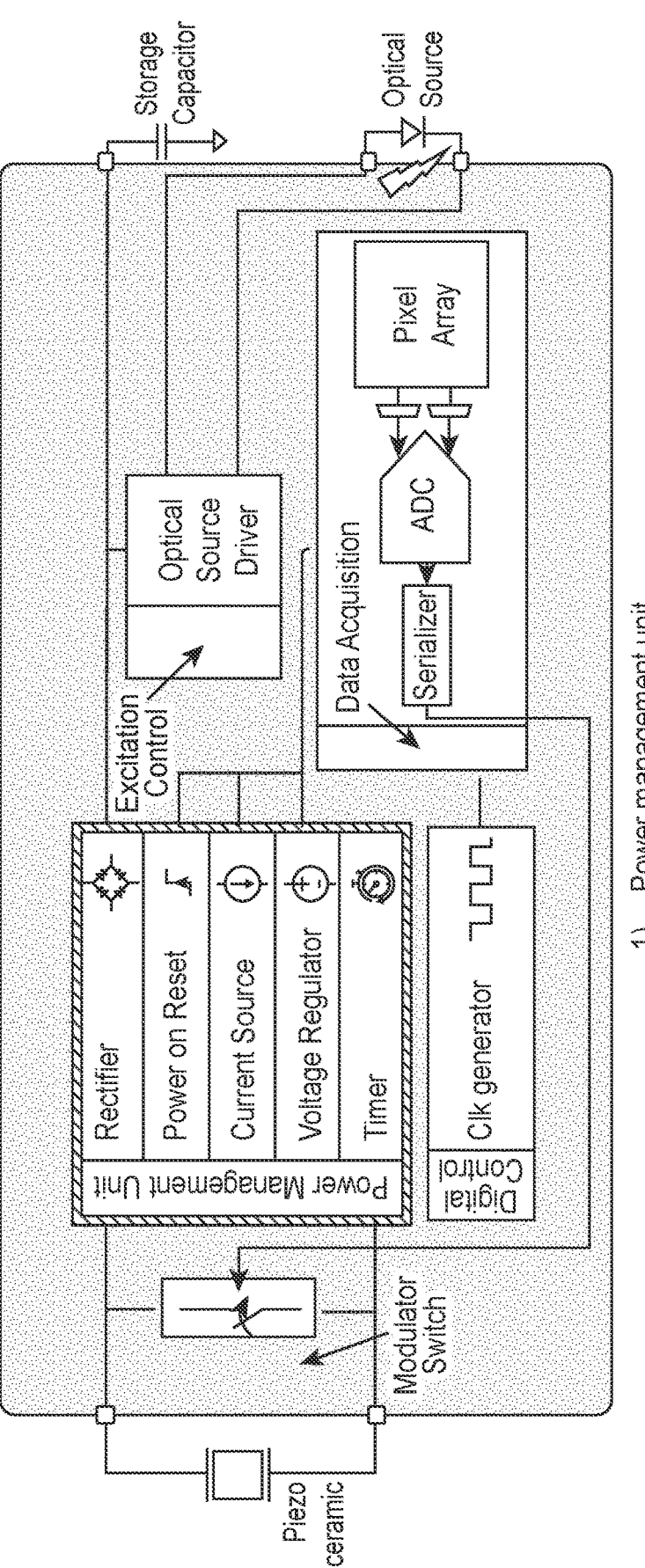
FIG. 28. System Block Diagram. A high-level block diagram of the imager chip is shown. The chip consists of 4 main blocks. A power management unit harvests power from the ultrasound (US) signal and rectifies it to a DC voltage to regulate the supply for the rest of the device.
Figure 29:
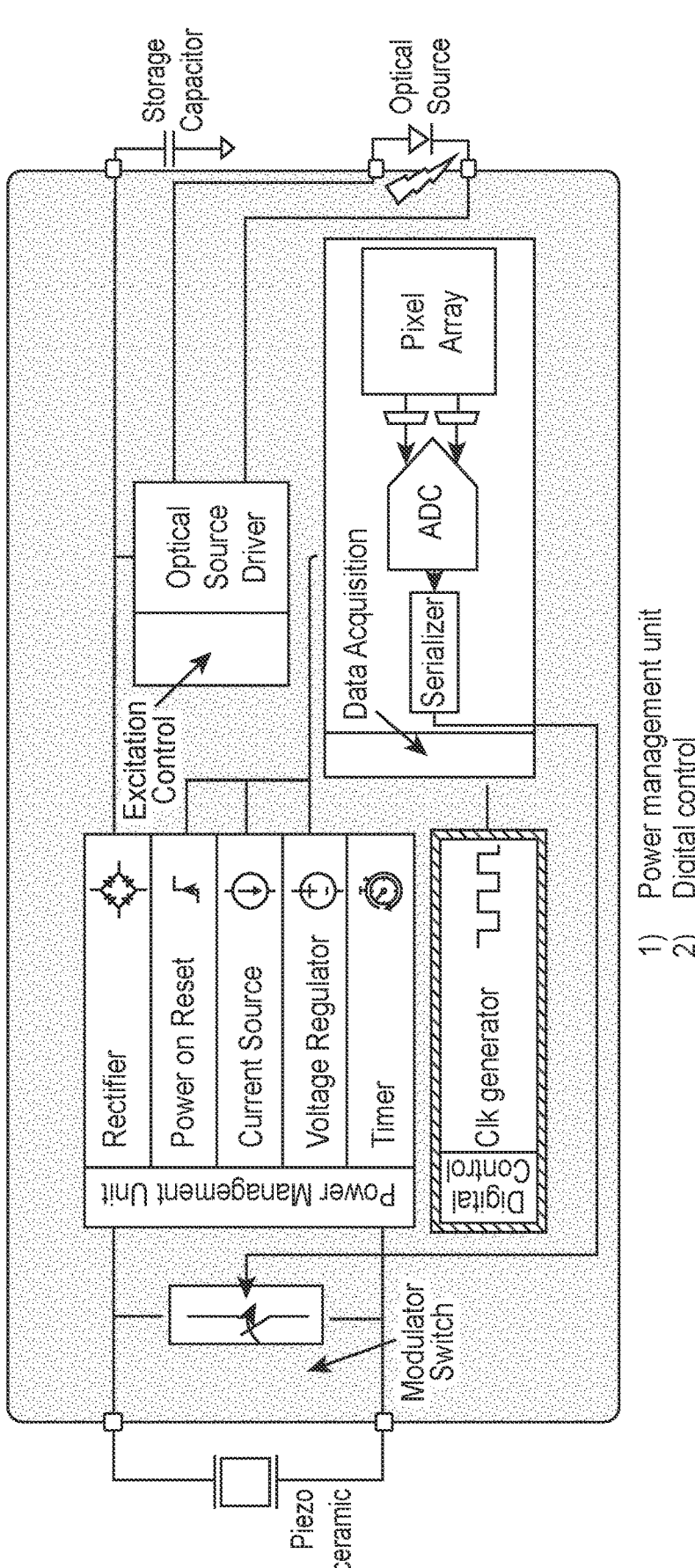
FIG. 29. A digital control block synchronizes operation of the laser diode with the imager, which is used to minimize the power used by the system. It turns the laser diode on only when the imager is ready to capture an image.
Figure 30:
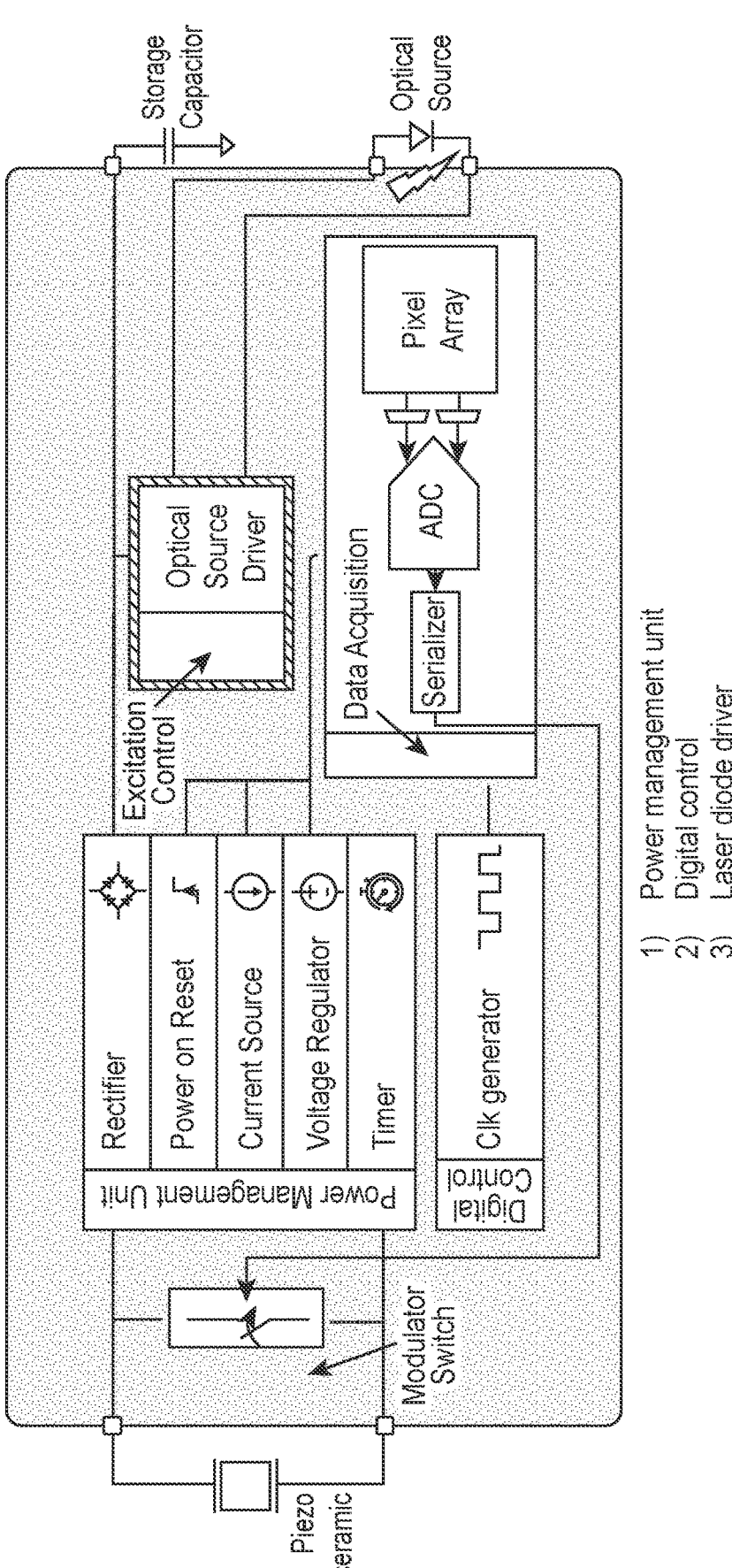
FIG. 30. A laser driver is used to supply and control the optical source while regulating the maximum applied voltage to protect it.
Figure 31:
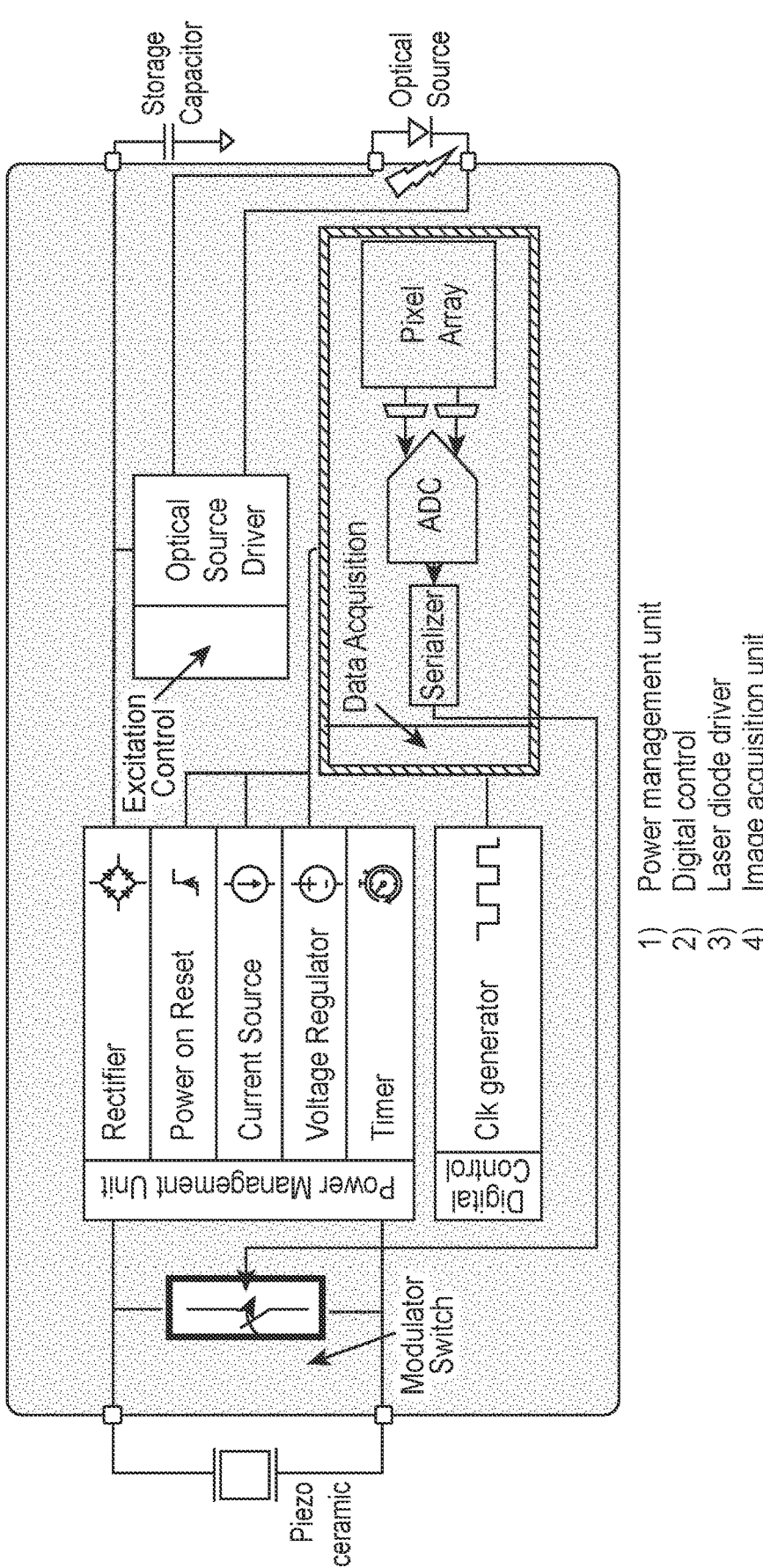
FIG. 31. Image acquisition unit. A pixel array is used to capture the image. An analog to digital converter is used to digitize the data. A modulator is used for transmitting the data via ultrasound backscatter.
Figure 32:
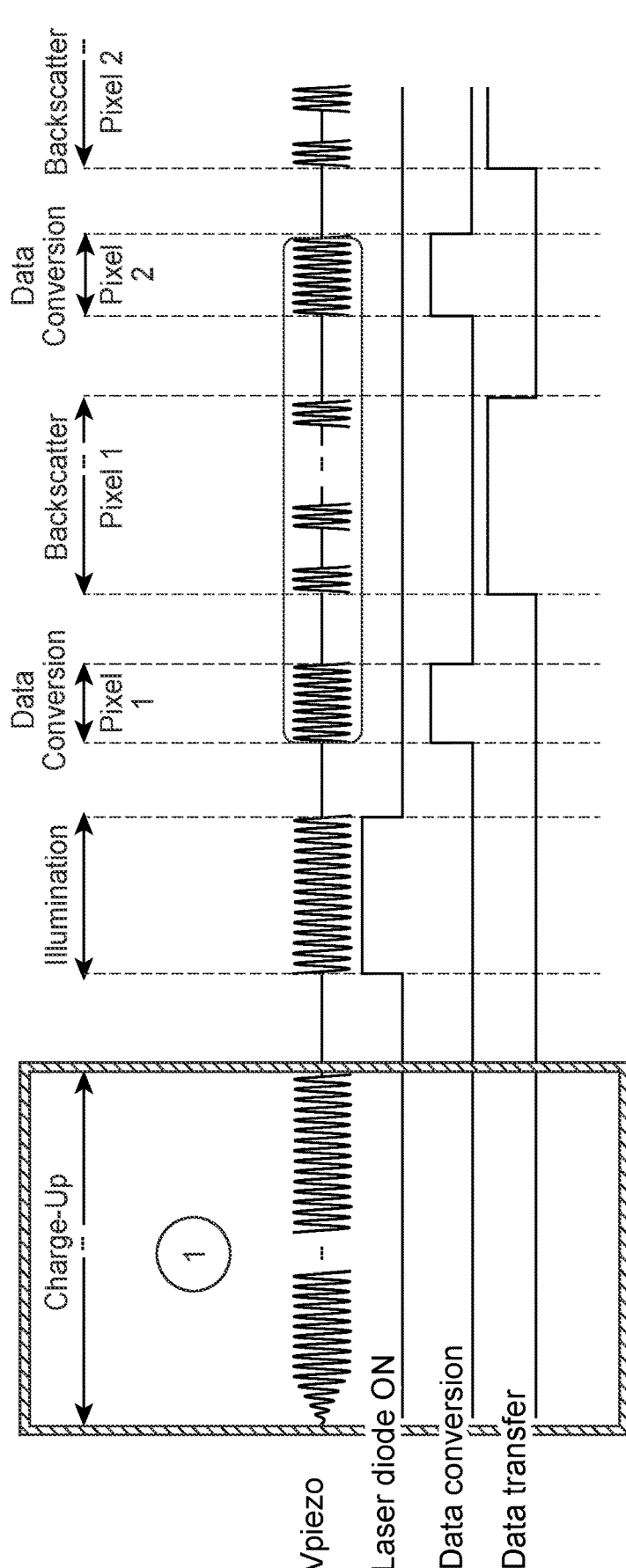
FIG. 32. Timing diagram of the imager. Charging the device starts upon the arrival of the ultrasound signal on the piezo terminals.
Figure 33:
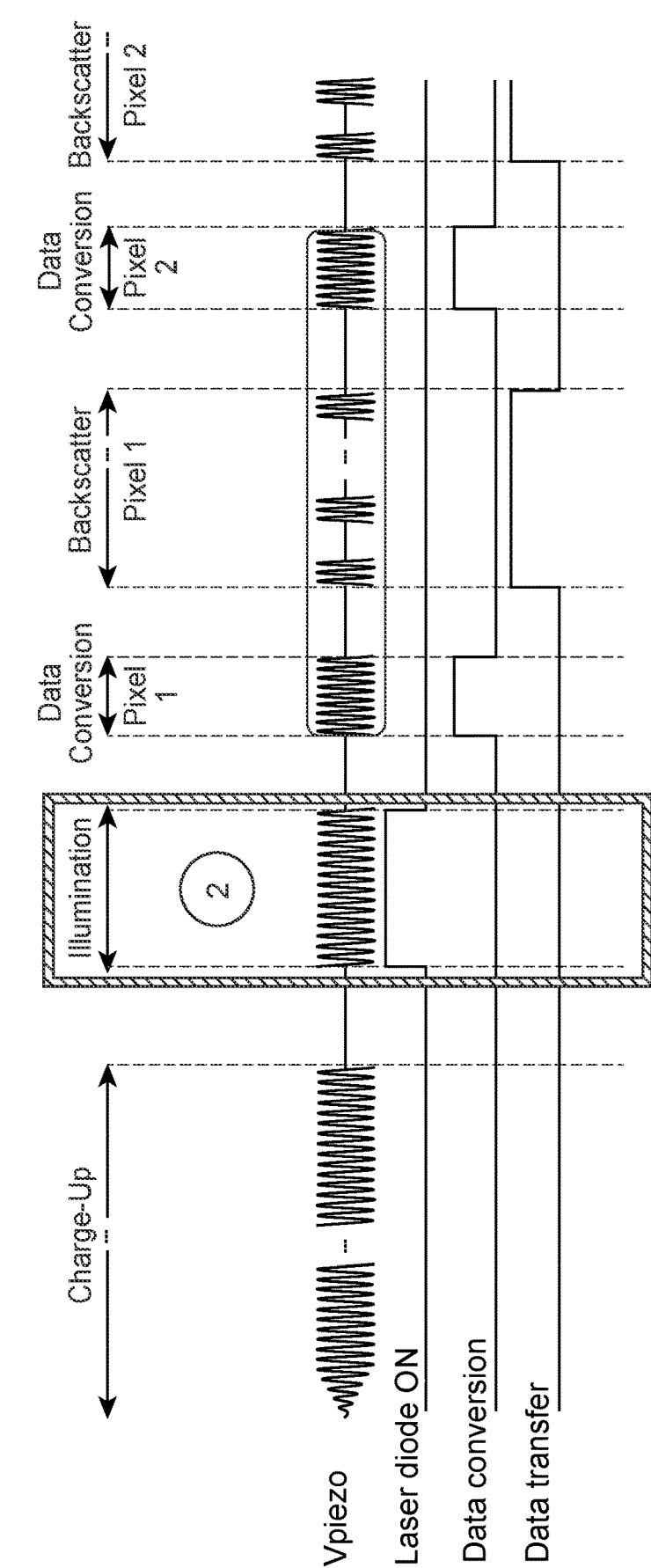
FIG. 33. Timing diagram of the imager. Once the device is charged to a pre-specified level, the illumination state starts by turning the laser diode and the pixel array on simultaneously.
Figure 34:
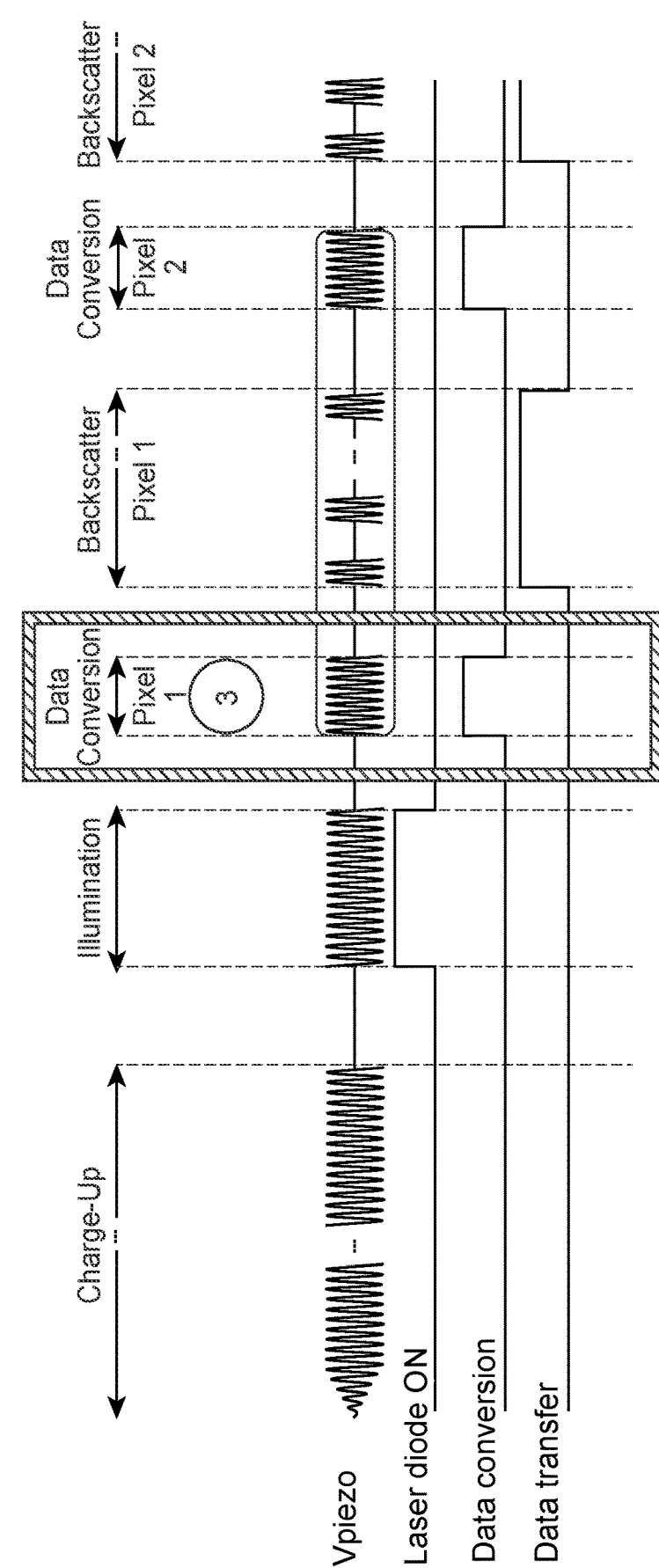
FIG. 34. Timing diagram of the imager. Once the image is captured, the pixel values are read sequentially and converted to digital signals to enable robust digital communication.
Figure 35:
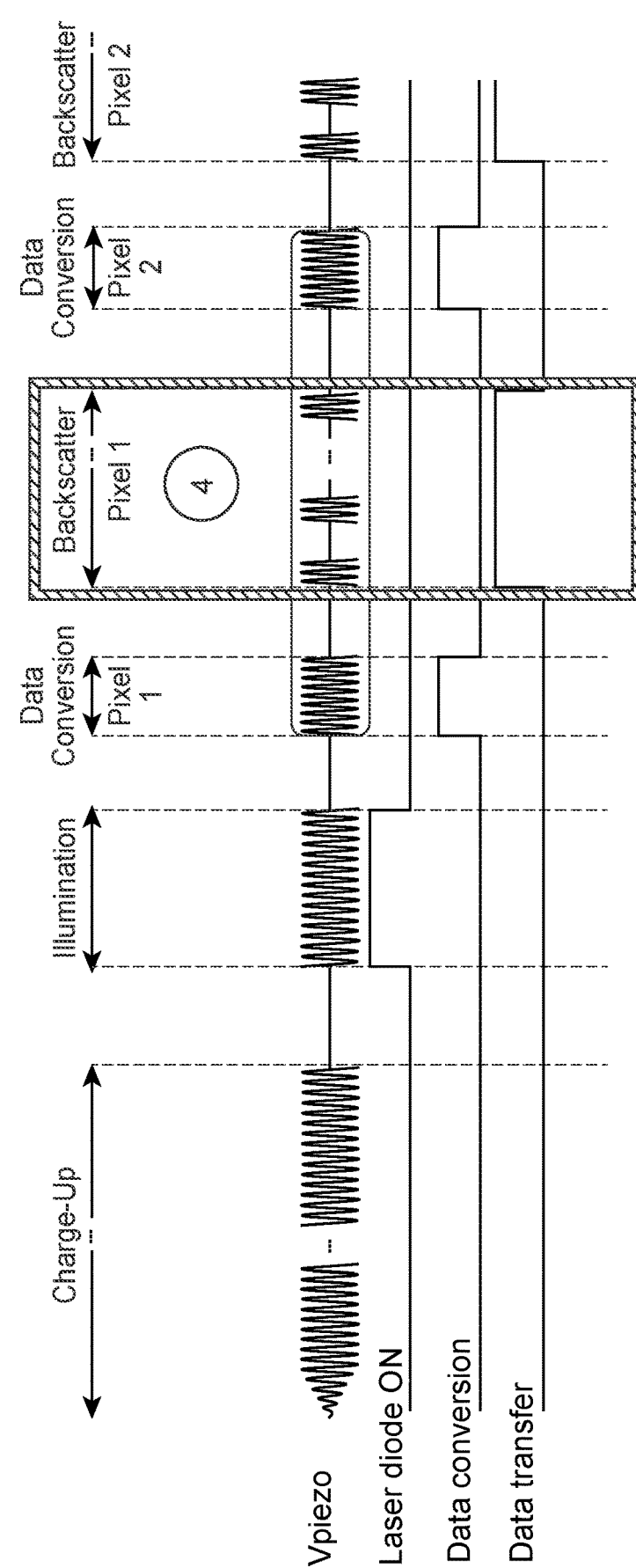
FIG. 35. Timing diagram of the imager. The digitized bits modulate the piezoceramic and the backscattered signal is received on the external transducer.
Figure 36:
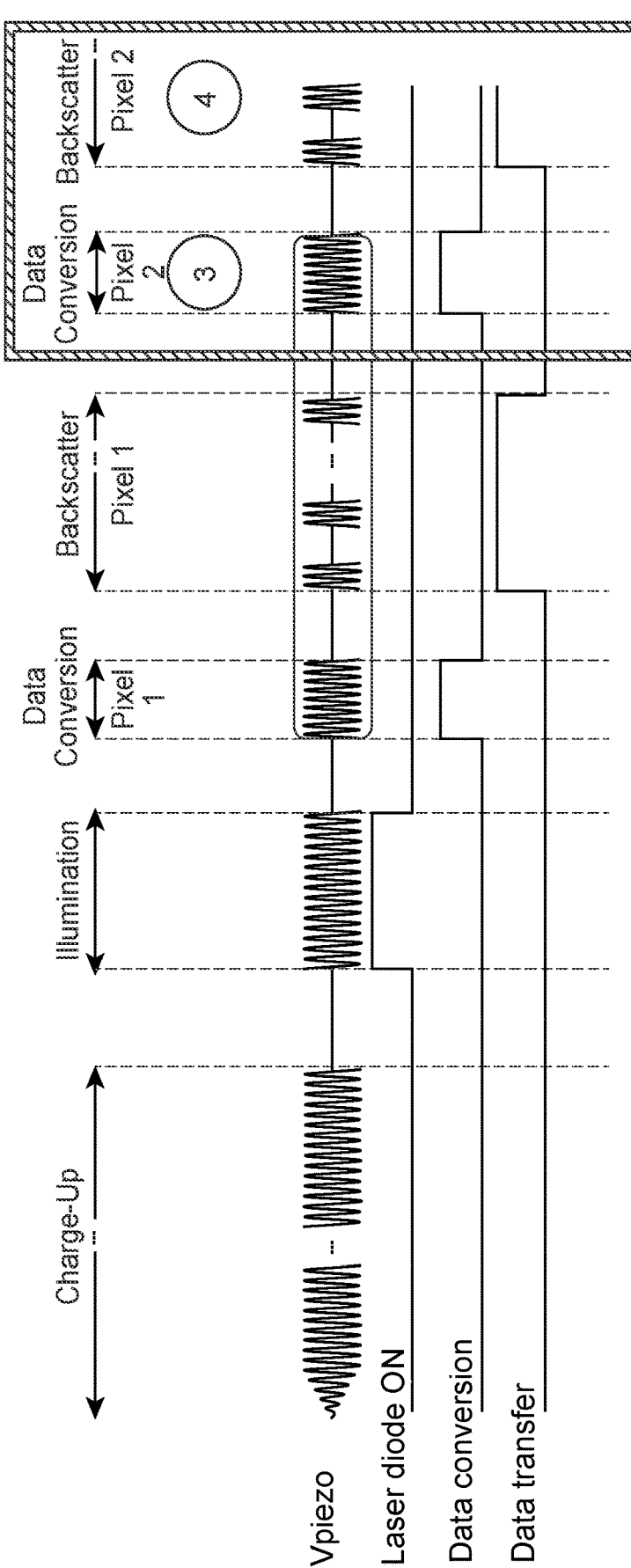
FIG. 36. Timing diagram of the imager. The procedure repeats until all of the pixels in the array are read and transferred.
Figure 37:
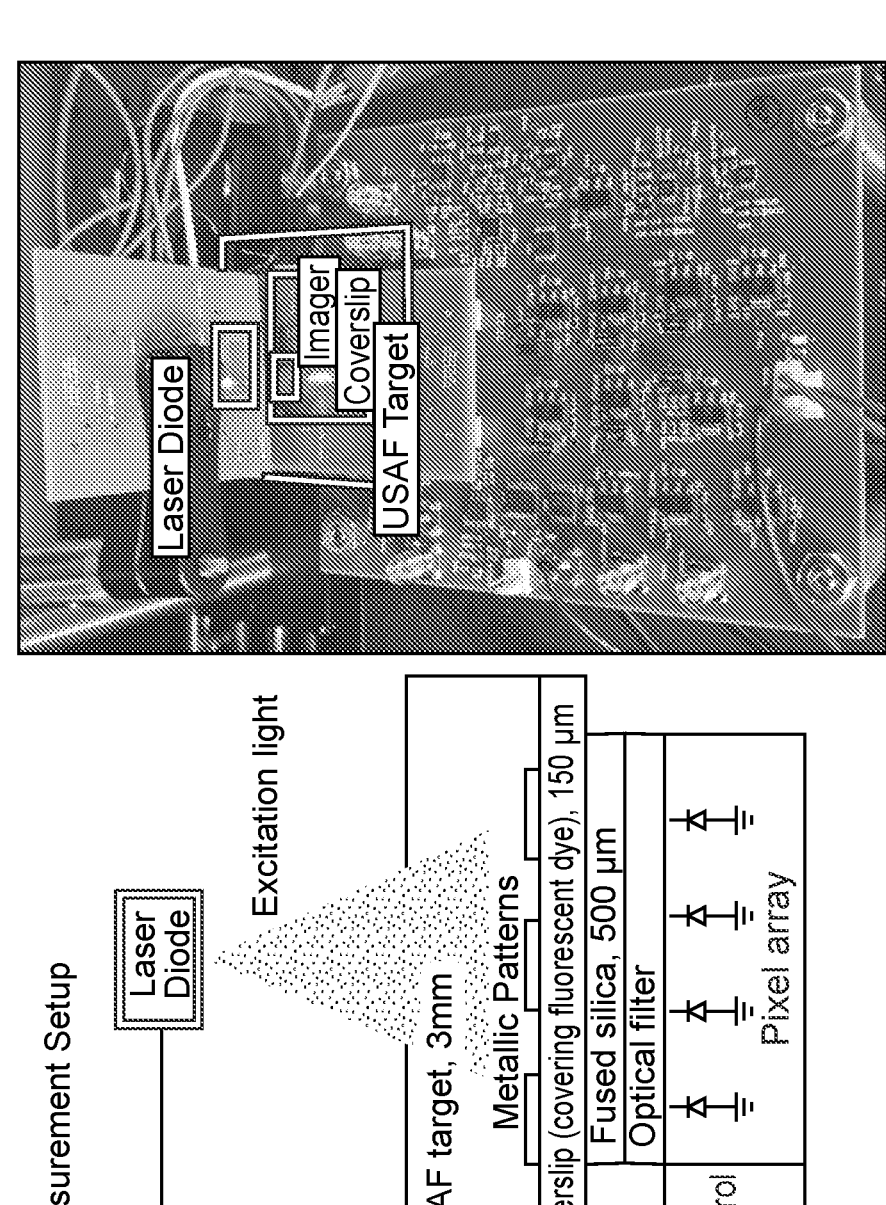
FIG. 37. Device fabrication and measurement setup.
Figure 41:
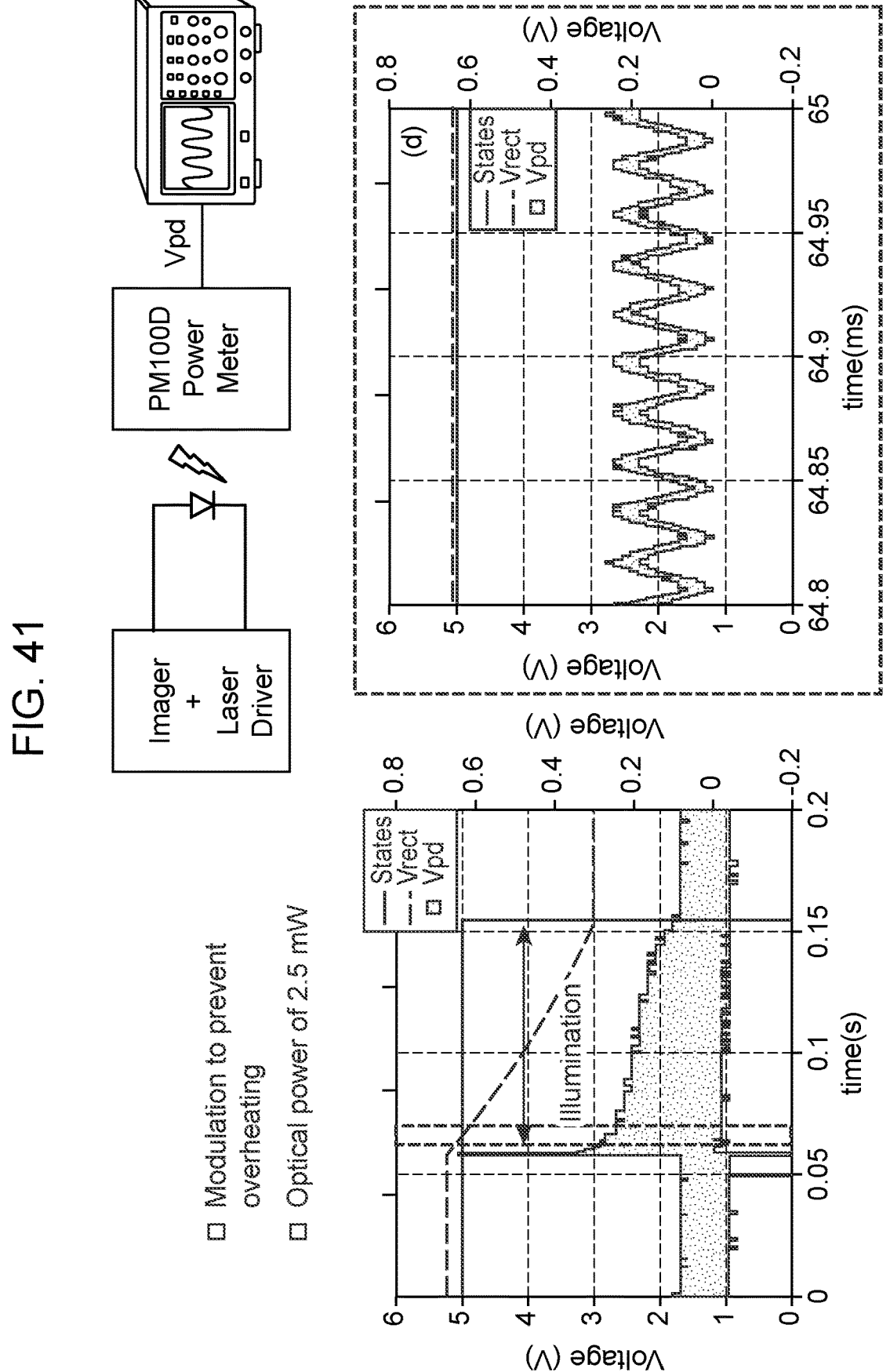
FIG. 41. Laser Driver Operation. Performance of the laser driver is characterized by an external optical power meter. The output of the power meter, labeled Vpd, is connected to an oscilloscope for visualization. Vpd is proportional to the intensity of the optical power from the diode. It is shown that the laser diode is only turned on during the illumination interval and it is continuously switched on and off with a high frequency to avoid overeating the laser diodes. An average optical power of 2.5 mW is achieved and is sufficient for our imaging purposes which is clusters of 100 cells. The system obtains images with a pixel-level resolution within a 21s frame-time fast enough to capture minute-scale multicellular changes inside the body.

FIG. 26A shows the output images of the corresponding metallic locations on the USAF target illuminated by the 635 nm Roithner laser diode and emitted from the fluorescent dye. As depicted in FIG. 26B the chip captures the selected structures with single pixel resolution (~55 μm) with a 64 ms integration time. This is a proof-of-concept demonstration of the performance of the SoC for a bench-top experimental setup. The input source is applied in a setup representative of the piezoceramic device which facilitates reproducibility for a fully wireless setup imaging ex vivo samples.

IV. Conclusions

This work presents a fully contained implantable image sensor to provide real-time assessments of the tissue at early stages of disease progression addressing challenges in immunotherapy. We demonstrate, to the best of our knowledge, a prototype for unprecedented wireless chip-scale fluorescence microscopy with frame times close to 20-25 s eliminating the need for focusing lenses, fiber optics, batteries, or any external wiring.

References

[1]S. A. Rosenberg, "Shedding Light on Immunotherapy for Cancer," *New England Journal of Medicine*, vol. 350, no. 14, pp. 1461-1463, 2004.

[2]P. Sharma et al., "Primary, Adaptive, and Acquired Resistance to Cancer Immunotherapy," *Cell*, vol. 168, no. 4, pp. 707-723, 2017.

[3]L. A. Emens et al., "Cancer immunotherapy: Opportunities and challenges in the rapidly evolving clinical landscape," *European Journal of Cancer*, vol. 81, pp. 116-129, 2017.

[4]H. L. Kaufman et al., "The Society for Immunotherapy of Cancer consensus statement on tumour immunotherapy for the treatment of cutaneous melanoma," *Nature Reviews Clinical Oncology*, vol. 10, pp. 588-598, 2013.

[5]A. Haslam and V. Prasad, "Estimation of the Percentage of US Patients with Cancer Who Are Eligible for and Respond to Checkpoint Inhibitor Immunotherapy Drugs," *JAMA Network Open*, vol. 2, no. 5, pp. e192535-e192535, May 2019.

[6]E. B. Garon et al., "Five-Year Overall Survival for Patients with Advanced Non-Small-Cell Lung Cancer Treated With Pembrolizumab: Results From the Phase I KEYNOTE-001 Study," *Journal of Clinical Oncology*, vol. 37, no. 28, pp. 2518-2527, 2019.

[7]J. V. Frangioni, "New technologies for human cancer imaging," *Journal of Clinical Oncology*, vol. 26, no. 24, pp. 4012-21, 2008. [8]R. R. Singh et al., "A CMOS/Thin-Film Fluorescence Contact Imaging Microsystem for DNA Analysis," *IEEE Transactions on Circuits and Systems I: Regular Papers*, vol. 57, no. 5, pp. 1029-1038, May 2010.

[9]Y. Sunaga et al., "Implantable imaging device for brain functional imaging system using flavoprotein fluorescence" *Japanese Journal of Applied Physics*, vol. 55, no. 3S2, 2016.

[10]J. Heymes et al., "Implantable CMOS pixel sensor for positron imaging in rat brain," *Nuclear Instruments and Methods in Physics Research Section A: Accelerators, Spectrometers, Detectors and Associated Equipment*, vol. 911, no. 24, pp. 19-24, 2018.

[11]F. Galli, J. V. Aguilera, B. Palermo et al., "Relevance of immune cell and tumor microenvironment imaging in the new era of immunotherapy," *Journal of Experimental & Clinical Cancer Research*, vol. 39, 2020.

[12]L. Ye et al., "Tumor-Infiltrating Immune Cells Act as a Marker for Prognosis in Colorectal Cancer," *Frontiers in Immunology*, vol. 10, pp. 2368, 2019.

[13]E. P. Papageorgiou, B. E. Boser and M. Anwar, "Chip-Scale Angle-Selective Imager for In Vivo Microscopic Cancer Detection," *IEEE Transactions on Biomedical Circuits and Systems*, vol. 14, no. 1, pp. 91-103, 2020.

[14]E. P. Papageorgiou, B. E. Boser and M. Anwar, "Chip-scale fluorescence imager for in vivo microscopic cancer detection," 2017 *Symposium on VLSI Circuits*, 2017, pp. C106-C107.

[15]D. K. Piech, B. C. Johnson and K. Shen et al., "A wireless millimetre-scale implantable neural stimulator with ultrasonically powered bidirectional communication," *Nature Biomedical Engineering*, vol. 4, pp. 207-222, 2020.

[16]M. J. Weber et al., "A Miniaturized Single-Transducer Implantable Pressure Sensor with Time-Multiplexed Ultrasonic Data and Power Links," *IEEE Journal of Solid-State Circuits*, vol. 53, no. 1, pp. 1089-1101, 2018.

[17]S. Akram et al., "Transperineal implantation of gold fiducial markers (gold seeds) for prostate image-guided radiation therapy: a feasible technique associated with a low risk of complications," *Journal of medical radiation sciences*, vol. 62, pp. 261-266, 2015.

[18]K. Ito et al., "Near-Infrared Photochemoimmunotherapy by Photoactivatable Bifunctional Antibody-Drug Conjugates Targeting Human Epidermal Growth Factor Receptor 2 Positive Cancer," *Bioconjugate Chemistry*, vol. 28, no. 5, pp. 1458-1469, 2017.

[19]M. A. Albota, C. Xu, and W. W. Webb "Two-Photon Fluorescence Excitation Cross Sections of Biomolecular Probes from 690 to 960 nm," *Applied Optics*, vol. 37, pp. 7352-7356, 1998.

[20]L. Wang, A. K. Gaigalas and V. Reipa, "Optical properties of Alexa 488 and Cy5 immobilized on a glass surface," *Biotechniques*, vol. 38, no. 1, pp. 127-32, Jan 2005.

[21]G. Hong et al., "Near-Infrared-Fluorescence-Enhanced Molecular Imaging of Live Cells on Gold Substrates," *Angewandte Chemie International Edition*, vol. 50, no. 20, pp. 4644-4648, 2011.

[22]J. Thimot, K. L. Shepard "Bioelectronic devices: Wirelessly powered implants," *Nature Biomedical Engineering*, vol. 1, Nov. 2017.

[23]S. Ayazian and A. Hassibi, "Delivering optical power to subcutaneous implanted devices," 2011 *Annual International Conference of the IEEE Engineering in Medicine and Biology Society*, 2011, pp. 2874-2877.

[24]M. M. Ghanbari and R. Muller, "Optimizing Volumetric Efficiency and Backscatter Communication in Biosensing Ultrasonic Implants," *IEEE Transactions on Biomedical Circuits and Systems*, vol. 14, no. 6, pp. 1381-1392, Dec. 2020.

[25]S. Qi et al., "Long-term intravital imaging of the multicolor-coded tumor microenvironment during combination immunotherapy," *eLife*, vol. 5, pp. e14756, Nov. 2016.

Example 5

A 36×40 Wireless Fluorescence Image Sensor for Real-Time Microscopy in Cancer Therapy Introduction Real-time in vivo imaging provides detailed cellular information from targets inside the body. In cancer immunotherapy, for instance, this information can be utilized for early assessments of the treatment, where effective activation of the immune system leads to durable responses against cancer. While only 30% of the patients respond to the treatment, detailed multicellular-level information can help rapidly alter the therapy based on the individual's response. However, this is not possible with current modalities such as CT or MRI that image purely anatomic changes taking months to manifest, by the end of which the window of cure is lost. Moreover, continuous monitoring of the tumor via frequent biopsies is impractical due to the invasiveness of the procedure. To overcome these limitations, fluorescence microscopy can be used to identify multiple cell types within tissue during ongoing therapy.

To implement noninvasive chip-scale fluorescence microscopy, a mm-scale wireless implantable imaging system consisting of an illumination source and an image sensor is required. While state-of-the-art image sensors provide high resolution microscopy, they lack wireless interfaces and require external circuitry making them impractical for chronic real-time in vivo monitoring [1,2]. Recent implantable systems have shown power transfer and data communication for low power sensors using ultrasound (US), but they haven't demonstrated wireless power transfer for high-power operations of the SoC such as optical excitation. Here, we present a 36×40 pixel implantable imaging system fabricated in 0.18 μm CMOS process for wireless fluorescence microscopy at a depth of 2 cm.

Figure 42A:
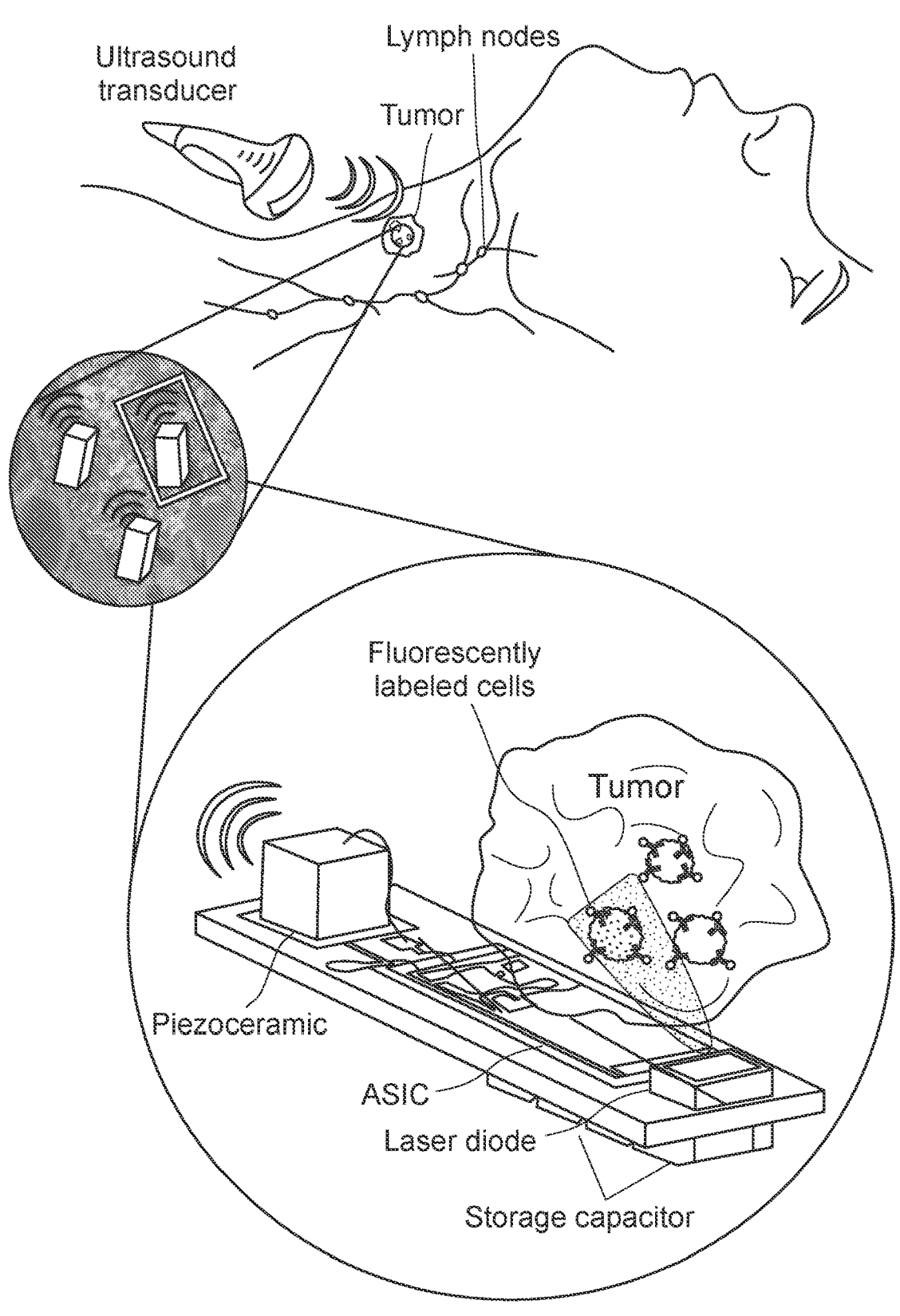
FIGS. 42A-42B.
Figure 42B:
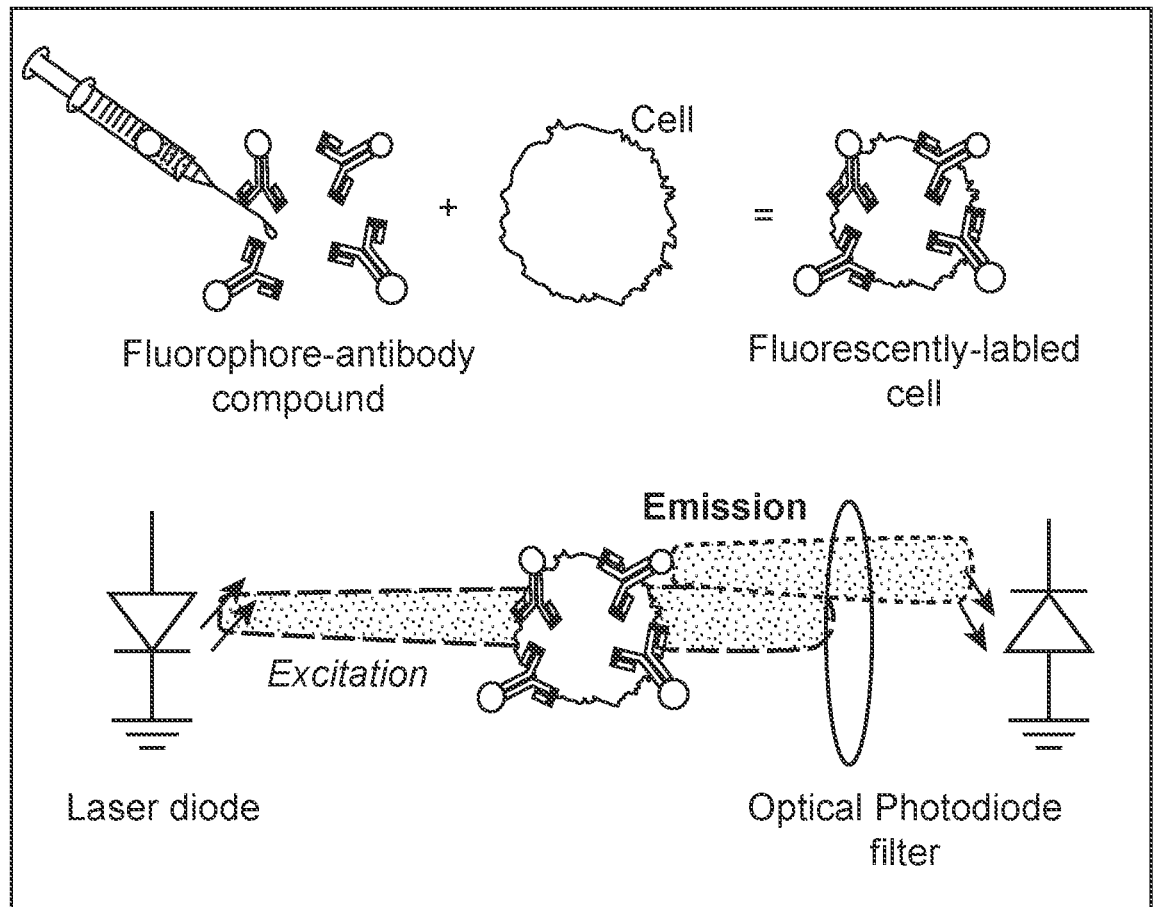
Figure 42B:
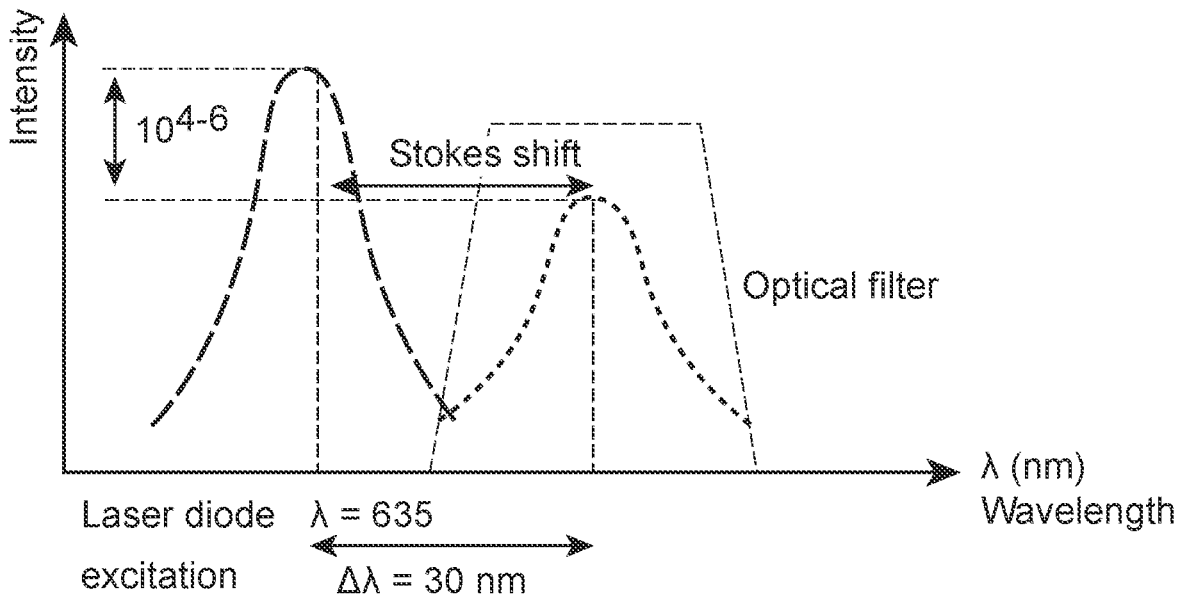

FIG. 42 shows the conceptual diagram of the implant consisting of 1) a 1.5×1.5×1.5 mm$^3$ piezoceramic (Lead Zirconate Titanate, PZT) 2) an imager ASIC with the pixel array covered by an optical wavelength filter (ET FITC-Cy5, Chroma) 3) a laser diode (CHIP-635-P5, Roithner Laser-Technik) for narrowband excitation of fluorescently-labeled targets and 4) a 1.4mF capacitor to store charge which can be decreased in size by using more efficient optical sources. Previously labeled with injected fluorophore-antibody compounds, the cells excited with the laser diode at 635 nm emit light at a wavelength differing by 30 nm (Stokes shift). A high-Q bandpass optical filter with a 60 dB rejection at the excitation band eliminates bleed-through from the higher intensity (×10$^5$) illumination and background to the emission band. The fluorescence signal intensity is given by F=6QP$_{in}$N where σ, Q and N refer to the absorption cross-section, quantum yield, and the number of fluorophores attached to the target and P$_{in}$ is the incident optical intensity. A 1 pW fluorescence signal detectable by the imager in [3], with an average binding of 10$^6$ fluorophores of typical dyes (i.e. Cyanine5.5-NHS), a quantum yield of 20% and an absorption cross-section of 10$^{-16}$ cm$^2$ requires a high 50 mW/cm$^2$ optical excitation intensity at the absorption peak of the fluorophore with minimum intensity for out of band light. Therefore, a laser diode is chosen to meet both requirements.

Figure 43A:
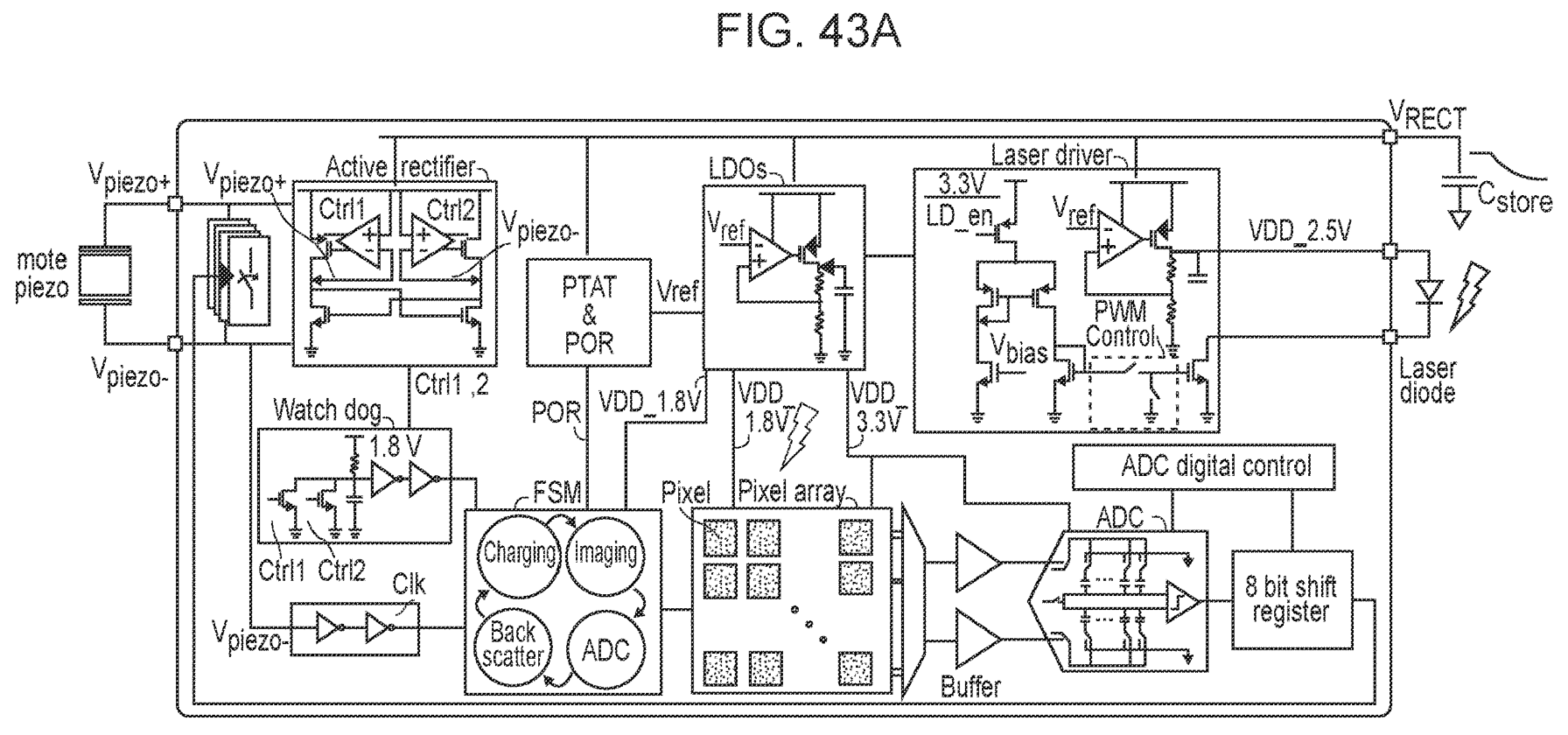
Figure 43B:
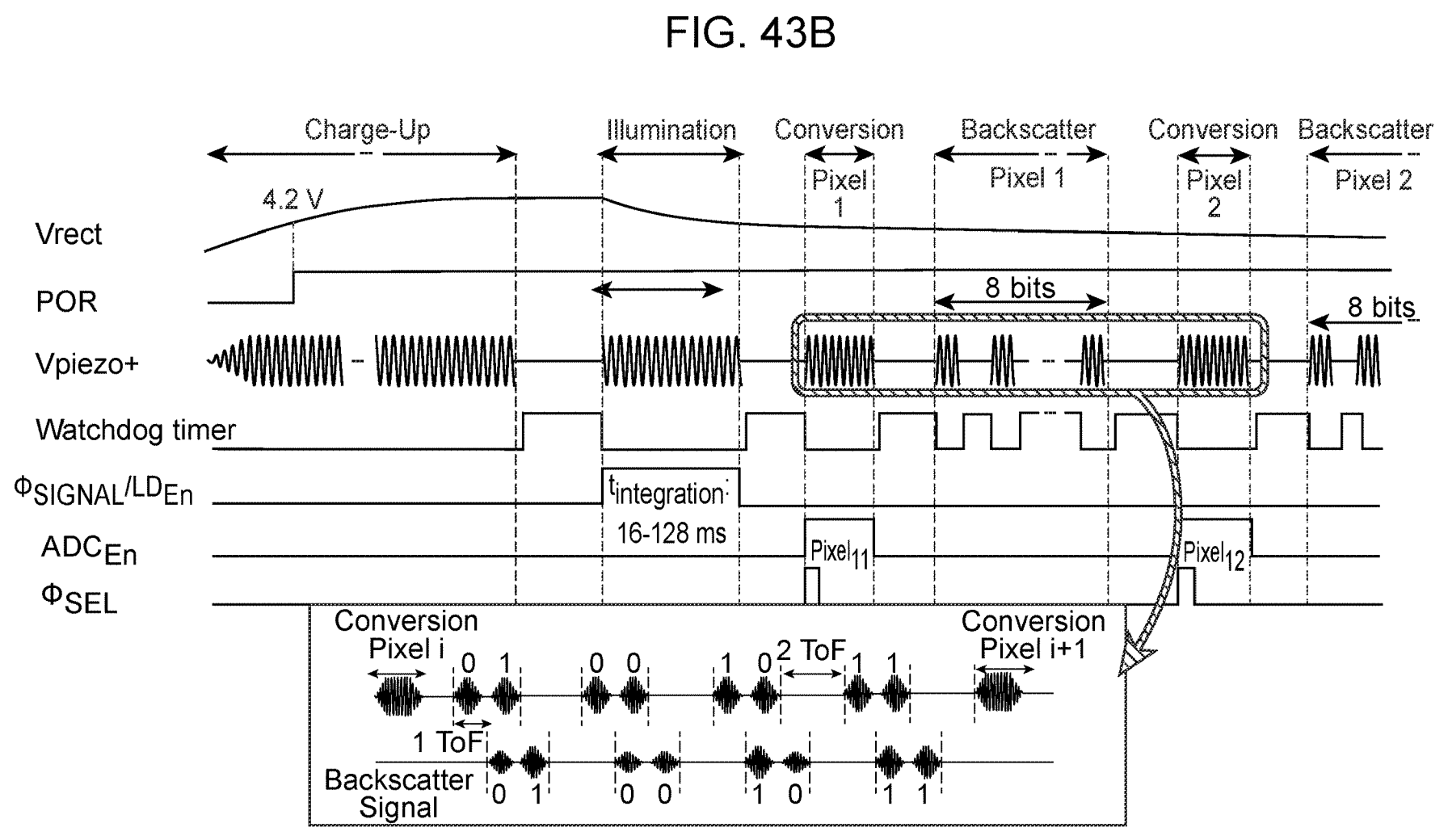

The detailed block diagram and timing of the system is shown in FIG. 43. The mote piezo receives the US pulses from an external transducer. An active rectifier converts the US signal to a DC voltage (V$_{RECT}$) and charges the storage capacitor (C$_{store}$) up to 5 V. Once V$_{RECT}$ reaches 4.2 V, a power on reset (POR) signal is triggered and the finite state machine (FSM) resets to the Charging state. A watchdog signal tracks ultrasound free intervals to navigate state transitions of the FSM run by extracted clock from the US waveform. Upon arrival of the first rising edge of the watchdog, the chip moves to the Imaging state when the laser driver turns on and the pixel array captures the image. Both the laser and the pixel array are switched off after completion of the integration time. 8 integration times from 16-128 ms can be hard-coded into the implant. Once the image is captured as described in [3], the pixels are sampled sequentially with a Φ$_{SEL}$=5 s control pulse by a differential 8-bit SAR ADC. Multiple LDOs (1 V, 1.8 V, 2.1 V, 2.5 V, 3.3 V) supply the analog front end, the ADC, the FSM, and the laser driver. For a depth of 2 cm, each set of 2 bits is fit inside an interval equal to 2ToF (ToF=14 μs, time-of-flight) and is transmitted through On-Off keying (OOK) modulation via US backscattering. A programmable switch with 4 impedance values (1, 2, 4, 8 KΩ) sets the modulation depth based on the equivalent impedance of the piezoceramic at the operating frequency.

Figure 44A:
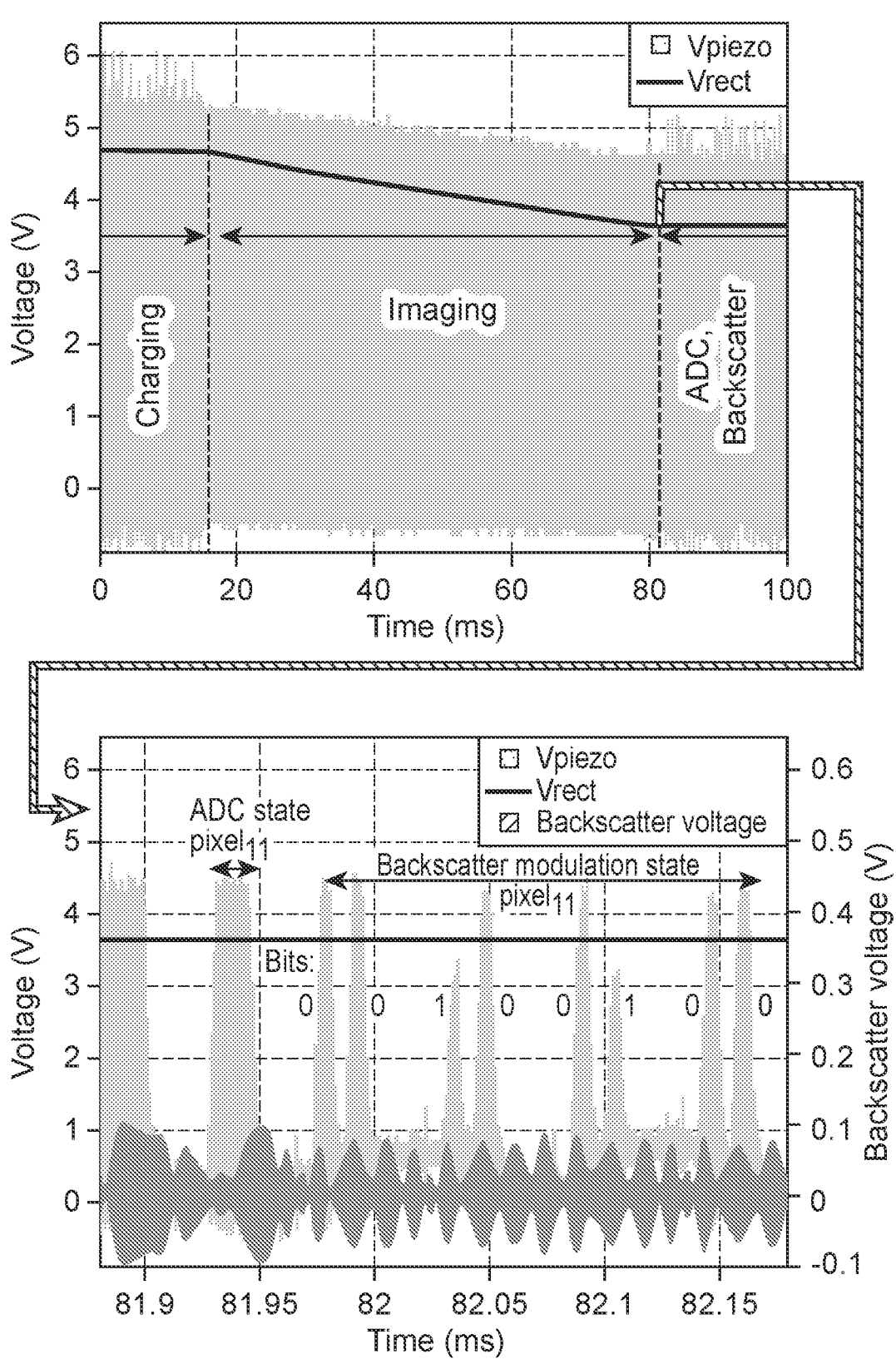
FIGS. 44A-44C.
Figure 44B:
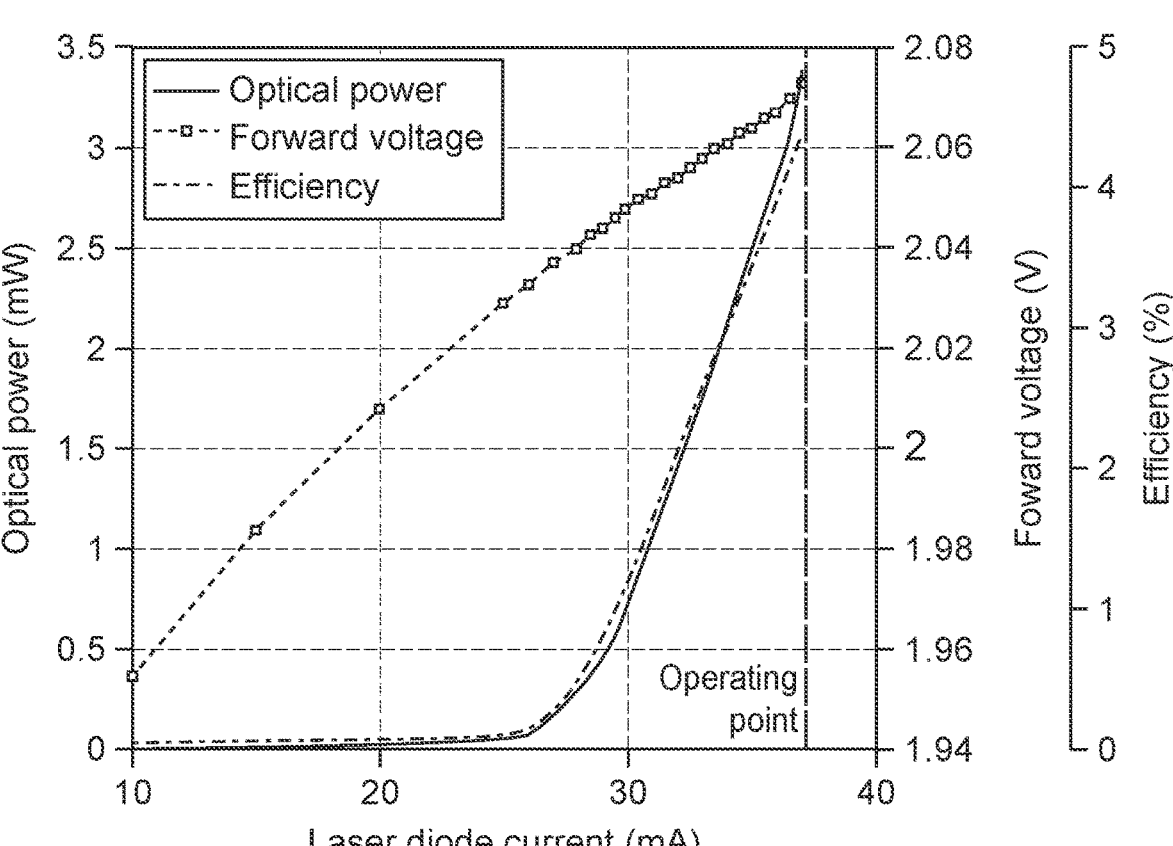
Figure 44C:
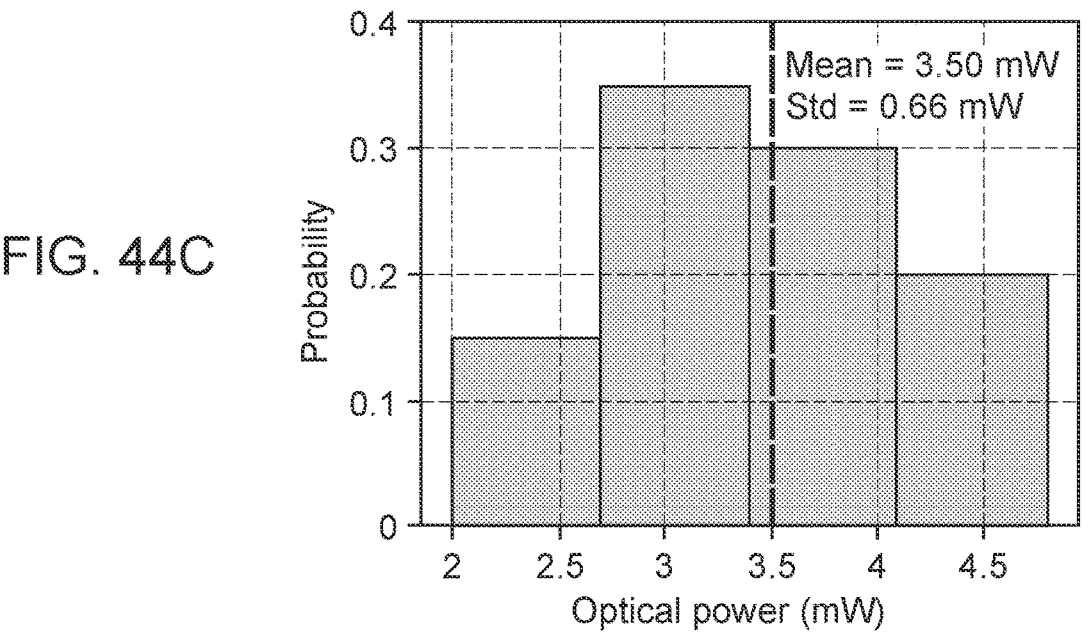
Figure 45A:
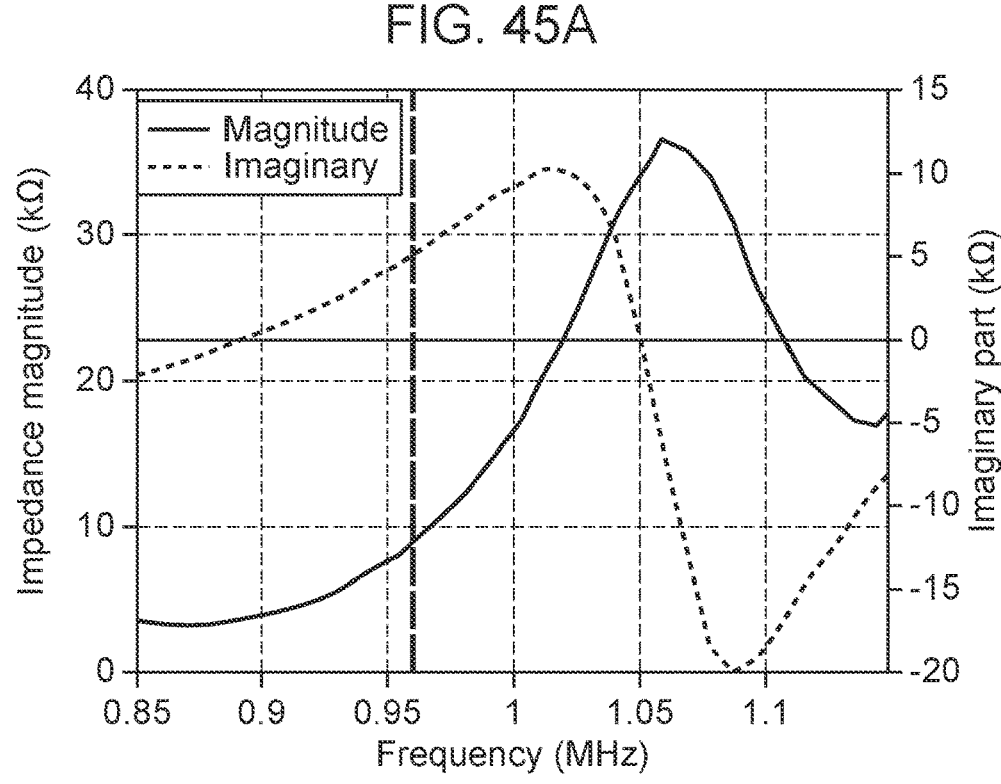
FIGS. 45A-45D. Frequency spectrum of (FIG. 45A) impedance and (FIG. 45B) harvested voltage of the piezoceramic (FIG. 45C) serial data and backscatter signal with (FIG. 45D) modulation depth of 16% and BER of $8.7 \times 10^{-5}$.
Figure 45B:
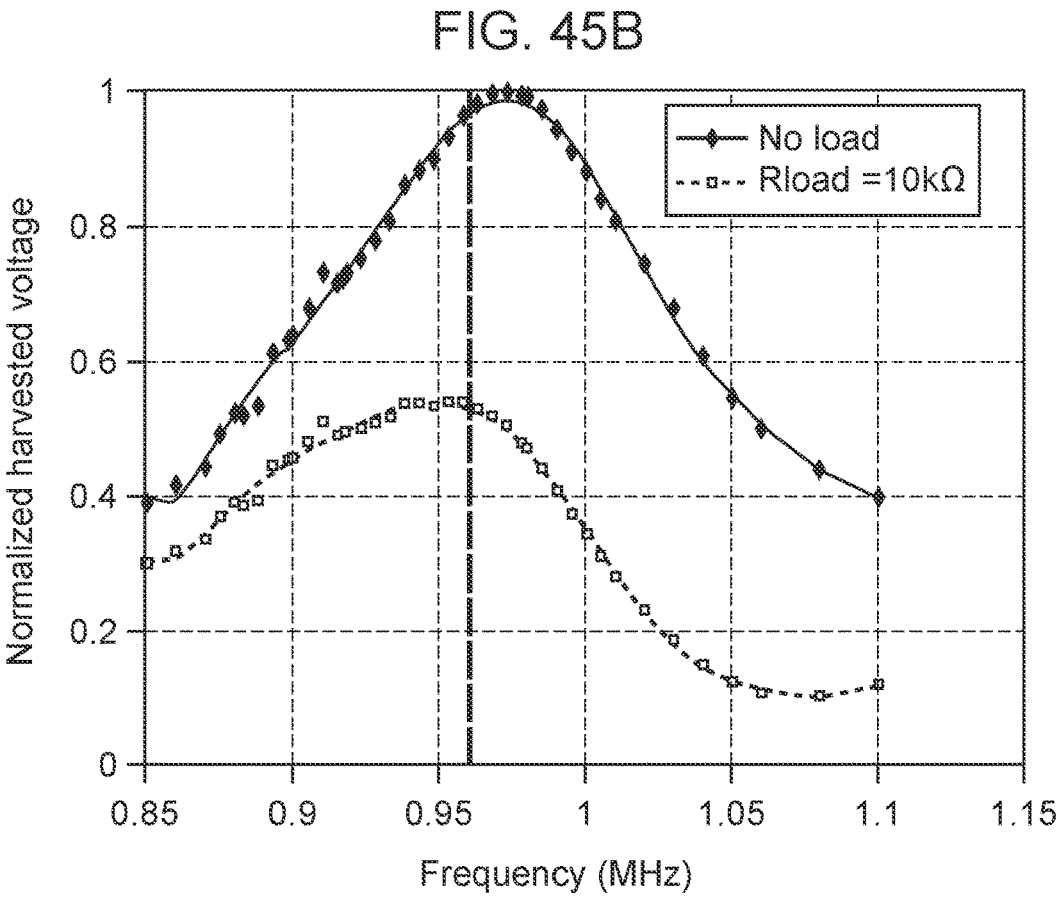
Figure 45C:
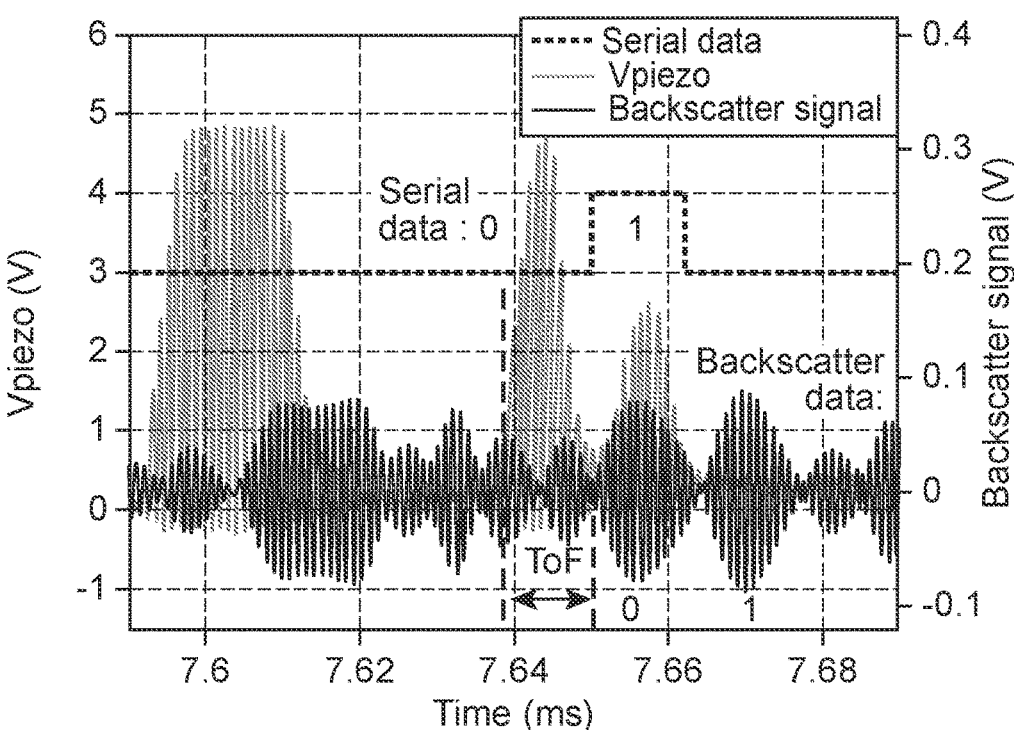
Figure 45D:
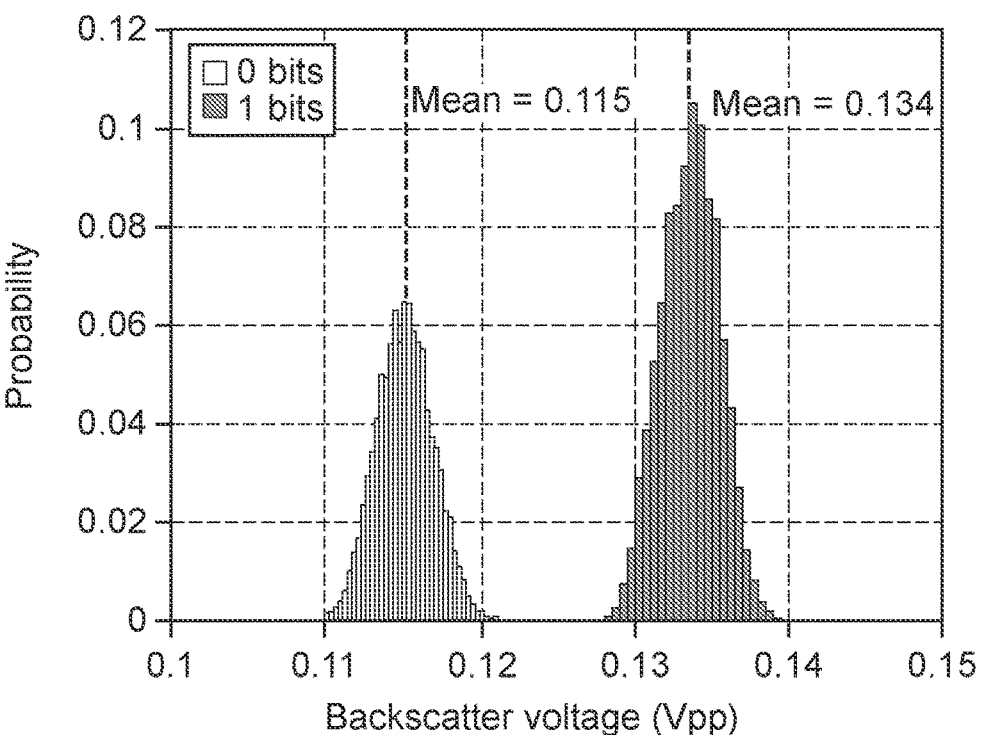

FIG. 44A shows state transitions and the 1 V droop on V$_{RECT}$ during a 64 ms illumination. After illumination, V$_{RECT}$ maintains a voltage higher than 3.5 V for ADC and US Backscattering (FIG. 44B). The electro-optical characterization of the laser diode with a power meter (PM100D, Thorlabs) shows an optical power of 3.4 mW for a 37 mA current and 2.1 V forward voltage resulting in an electrical to optical efficiency of 4.4% (FIG. 44C). To avoid overheating the diode, a PWM controller divides the main clock to generate a 50 kHz pulse with a 50% duty cycle within the integration time shown in previous work [4]. The distribution of the average optical output power for 20 measurements in FIG. 44D shows an average optical power of 3.5 mW (average current of 37.07 mA) and an average electrical efficiency of 66% for the laser driver as V$_{RECT}$ is required to be maintained above 3.5 V for the operation of the IC after illumination.

The impedance and open circuit voltage of the piezoceramic are characterized inside canola oil as shown in FIG. 45. To achieve maximum harvested voltage, the piezoceramic is operated off-resonance at 960 kHz. The spectrum of the harvested voltage is shown for the piezoceramic both off-load and loaded with the equivalent of the IC's input impedance (FIG. 45C). BER for a measurement performed at 2 cm of depth inside canola oil with a modulation depth of 16% is 8.7×10$^{-5}$ for 11.52 kbits (FIG. 45D).

Figure 46:
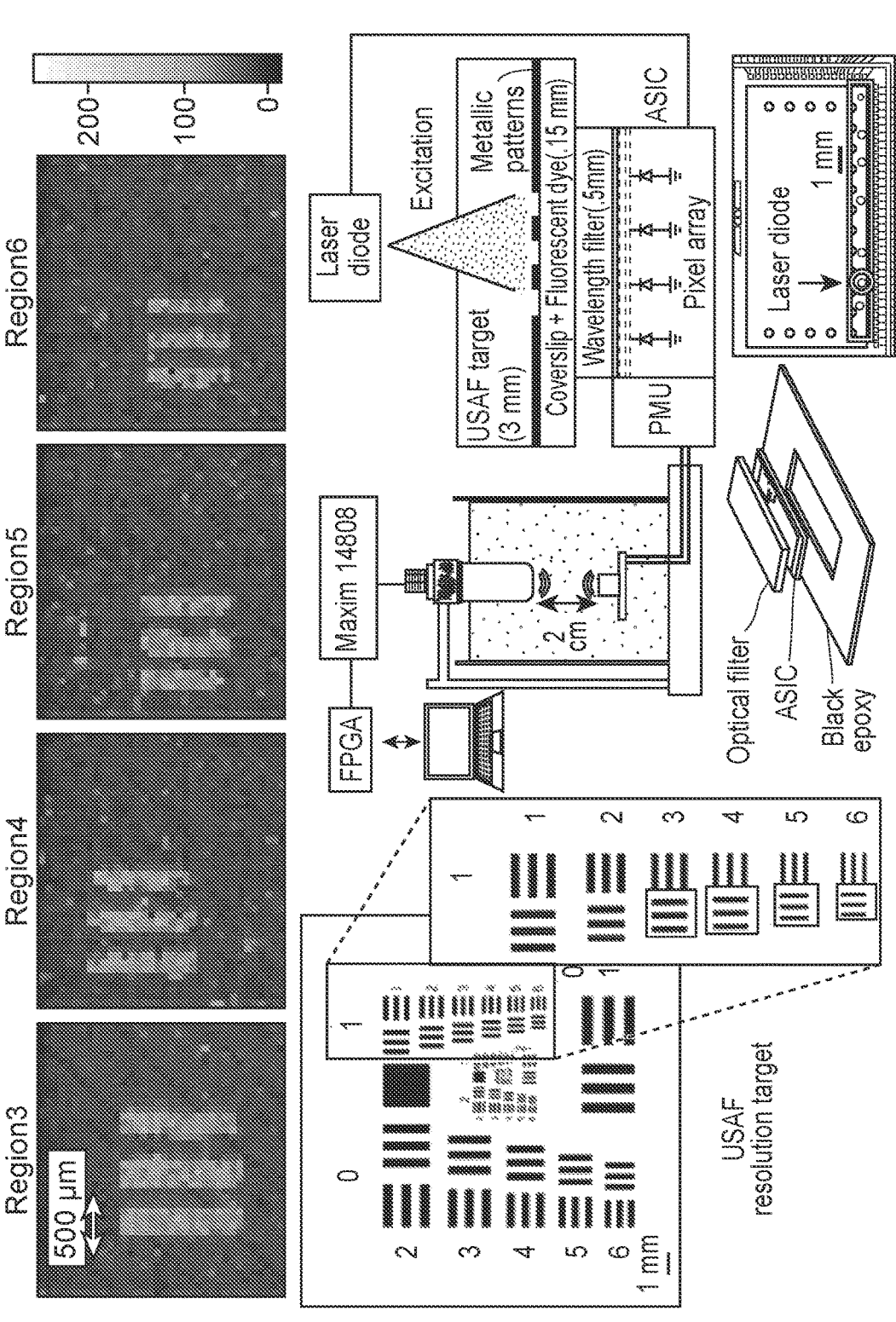
FIG. 46. Backscattered images shown in 8-bit ADC codes and in vitro fluorescence microscopy.

The measurement setup in FIG. 46 consists of the piezoceramic inside a tank of canola oil (0.25 dB/cm/MHz attenuation) connected to the imager. The optical filter is epoxied on the chip and is covered by black epoxy to eliminate any bleed-through from the edges. The on-chip laser driver is connected to the laser diode which illuminates the target from the top. The backscattered images from a Cyanine5.5-NHS fluorophore underneath a USAF resolution target with highlighted corresponding regions are shown in FIG. 46. The images are taken after a 40% duty-cycled 150 s Charging state to ensure safe operation of the US transducer. A 64 ms illumination with a total readout time of 389 ms via US backscatter capture metallic patterns with a single pixel resolution (~55 m). The frame time is sufficient to capture relatively slow movements of cells inside the body.

This this work is compared against recently published implantable imagers shown in the table in FIG. 47 [1,2,5]. To the best of our knowledge, this is the first wireless implantable fluorescence image sensor that transmits 11.52 kbits of data in a single measurement cycle by supplying the 0.26 mW pixel array and the high 78 mW power of the laser diode for a 64 ms illumination interval. The imaging operation is duty-cycled by 0.04% within a 150.5s frame time resulting in a system overall average power of 55 μW per frame.

REFERENCES

[1] T. Kobayashi et al., "Optical communication with brain cells by means of an implanted duplex microdevice with optogenetics and Ca2+ fluoroimaging". Sci Rep 6, (2016).

[2]J. Choi et al., "Fully Integrated Time-Gated 3D Fluorescence Imager for Deep Neural Imaging," in IEEE Transactions on Biomedical Circuits and Systems, Aug. 2020.

[3]E. P. Papageorgiou et al., "Chip-Scale Angle-Selective Imager for In Vivo Microscopic Cancer Detection," TBioCAS, 2020.

[4]R. Rabbani et al., "Towards an Implantable Fluorescence Image Sensor for Real-Time Monitoring of Immune Response in Cancer Therapy", EMBC, 2021.

[5]A. Sawaby et al., "A Wireless Implantable Ultrasound Array Receiver for Thermoacoustic Imaging," VLSI, 2018.

What is claimed is:

1. A fluorescence imager comprising:

a) an imaging array comprising a plurality of photodiodes arrayed on the surface of a chip, wherein each photodiode is coated with at least one layer of filter material that functions as an optical filter;

b) a plurality of light emitting sources to provide excitation light, wherein the plurality of light emitting sources are located on the chip or externally;

c) an on-chip or off-chip energy storage device to supply power for operation of the fluorescence imager;

d) a data storage unit in communication with the imaging array, wherein the data storage unit stores imaging data from the imaging array; and e) an application-specific integrated circuit (ASIC) configured to control voltages and supply power from the on-chip or off-chip energy storage device to the imaging array, the plurality of light emitting sources on the chip, and the data storage unit, wherein power supplied to the plurality of light emitting sources is supplied such that the plurality of light emitting sources are sequentially illuminated.

2. The fluorescence imager of claim 1, wherein the fluorescence imager has no optical lens and has dimensions of less than or equal to 5 mm in length.

3. The fluorescence imager of claim 1, wherein the light emitting sources are micro-laser diodes or light-emitting diodes, wherein each light-emitting diode further comprises an emission filter.

4. The fluorescence imager of claim 1, wherein the on-chip energy storage device or the off-chip energy storage device comprises a battery, a capacitor, a radionuclide, a photovoltaic system, or a radionuclide in combination with a scintillator and photovoltaic energy harvester.

5. The fluorescence imager of claim 1, further comprising a piezoelectric substrate attached to the surface of the chip or a solid support containing the chip, wherein the piezoelectric substrate is configured to receive ultrasound power from an external ultrasound transducer and supply power for operation of the fluorescence imager, wherein electrical energy output from the piezoelectric substrate in response to receiving the ultrasound power is stored in the on-chip energy storage device or the off-chip energy storage device, optionally wherein the piezoelectric substrate is a piezoelectric crystal or piezoelectric ceramic.

6. The fluorescence imager of claim 5, wherein the on-chip or off-chip energy storage device is a capacitor or rechargeable battery that stores electrical energy output from the piezoelectric substrate in response to receiving the ultrasound power, wherein the capacitor or rechargeable battery supplies power to the plurality of light emitting sources on the chip and the imaging array.

7. The fluorescence imager of claim 1, further comprising an on-chip antenna configured to receive radiofrequency

64

(RF) power from an external RF transducer or electromagnetic power inductively transferred to a coil from an external inductive transducer and supply power for operation of the fluorescence imager, wherein electrical energy output from the on-chip antenna in response to receiving the RF or electromagnetic power is stored in the on chip-energy storage device.

8. The fluorescence imager of claim 7 wherein the on-chip energy storage device or the off-chip energy storage device is a capacitor or rechargeable battery that stores electrical energy output from the antenna in response to receiving the RF power or the electromagnetic power, wherein the capacitor or rechargeable battery supplies power to the plurality of light emitting sources on the chip and the imaging array.

9. The fluorescence imager of claim 1, further comprising a data processing unit in communication with the data storage unit, wherein the data storage unit stores processed imaging data from the imaging array.

10. The fluorescence imager claim 1, further comprising a backscattering modulator unit or an active modulator implementing amplitude shift keying (ASK), phase shift keying (PSK), frequency shift keying (FSK), pulse width modulation amplitude shift keying (PWM-ASK), pulse position modulation (PPM) or spectrally efficient quadrature amplitude modulation (QAM), or a combination thereof, in communication with the imaging array.

11. The fluorescence imager of claim 1, further comprising a first wireless communication unit in communication with the data storage unit and an external data receiving device comprising a second wireless communication unit, wherein the first wireless communication unit utilizes a wireless communication protocol using an electromagnetic carrier wave or ultrasound to transfer data from the data storage unit to the external data receiving device comprising the second wireless communication unit, optionally wherein the electromagnetic carrier wave is a radio wave, microwave, or an infrared carrier wave.

12. The fluorescence imager of claim 1, wherein the plurality of light emitting sources located externally are micro-star light sources.

13. The fluorescence imager of claim 1, wherein an external power source supplies power to the plurality of light emitting sources located on-chip or externally.

14. The fluorescence imager of claim 1, wherein said at least one layer of filter material comprises or consists of amorphous silicon, crystalline silicon, gallium phosphide, cadmium selenide, gallium arsenide, or indium phosphide.

15. The fluorescence imager of claim 1, wherein the thickness of the layer of filter material on all the photodiodes is the same.

16. The fluorescence imager of claim 1, wherein the thickness of the layer of filter material is varied on the plurality of photodiodes to allow selection of light at different fluorescence emission wavelengths for multiple fluorophores having different fluorescence emission spectra.

17. The fluorescence imager of claim 1, wherein the fluorophore of interest has a fluorescence emission in the near-infrared or visible region of the electromagnetic spectrum, and the band gap and the thickness of the layer of filter material is chosen to allow selection of near-infrared light or visible light at the fluorescence emission wavelength of the fluorophore.

18. The fluorescence imager of claim 1, wherein the optical filter is an absorption filter or an interference filter, optionally wherein the absorption filter has a band gap and thickness suitable to allow light at a fluorescence emission wavelength of a fluorophore of interest to pass through to the photodiode, and optionally wherein the interference filter is a single bandpass, dual bandpass, triple bandpass, or quadruple bandpass interference filter.

19. The fluorescence imager of claim 18, wherein the interference filter further comprises:

a layer of absorption filter material on top of the interference filter or underneath the interference filter;

one or more layers of material comprising a plurality of angle selective gratings, collimators, or fiber optic plates that blocks light that is not incident within 5° to 30° of an axis perpendicular to the plane of the chip;

one or more layers of material comprising a plurality of fiber optic plates that blocks light that is not incident within 6° of an axis perpendicular to the plane of the chip; or one or more layers of material comprising a plurality of angle selective gratings that blocks light that is not incident within 10° to 15° of an axis perpendicular to the plane of the chip.

20. The fluorescence imager of claim 19, wherein said one or more layers of material comprising a plurality of angle selective gratings, collimators, or fiber optics are on top of the layer of filter material, underneath the layer of filter material, or both on top and underneath the layer of filter material, optionally wherein the layer on top of the layer of filter material blocks light that is not incident within 10°-15° of an axis perpendicular to the plane of the chip, and optionally wherein the layer underneath the layer of filter material blocks light that is not incident within 5°-30° of an axis perpendicular to the plane of the chip.

21. The fluorescence imager of claim 1, further comprising an on-chip clock.

22. The fluorescence imager of claim 1, further comprising a digital state machine that controls stages of operation of the chip, wherein the stages of operation comprise power-up, illumination and imaging, data storage, and transmission of imaging data.

23. The fluorescence imager of claim 22, wherein the transmission of imaging data can be triggered on demand, triggered at preset time intervals, triggered by an external transducer, or guided by an on-chip clock.

24. The fluorescence imager of claim 1, further comprising an edge computing device connected to the data storage unit, wherein the edge computing device receives data from the data storage unit.

25. The fluorescence imager of claim 1, further comprising a solid support, wherein the chip and the off-chip energy storage device or a piezoelectric substrate, or a combination thereof are on the surface of the solid support.

26. A system comprising:

a) the fluorescence imager of claim 1;

b) an external or internal power source; and c) an external data receiving device.

27. The system of claim 26, wherein the external power source is an ultrasound transducer, an electromagnetic (EM) transducer, an inductive transducer, or a radiofrequency (RF) transducer, wherein the external power source is used to charge the internal power source, and optionally wherein the external power source is portable.

28. The system of claim 26, wherein the internal power source comprises a battery, a radionuclide, a photovoltaic system, or a radionuclide in combination with a scintillator and photovoltaic energy harvester.

29. The system of claim 26, further comprising a fluorophore conjugate comprising a fluorophore conjugated to a binding agent that specifically binds to a cellular marker of interest.

30. The system of claim 26, wherein the external data receiving device comprises a wireless communication unit, wherein the wireless communication unit utilizes a wireless communication protocol using an electromagnetic carrier wave or ultrasound to receive data from the internal data storage unit of the fluorescence imager, and optionally wherein the electromagnetic carrier wave is a radio wave, microwave, or an infrared carrier wave.

31. The system of claim 26, wherein the external data receiving device further comprises a processor programmed to process data received from the fluorescence imager and display fluorescence images.

32. The system of claim 26, further comprising a display component, wherein the display component is connected to the external data receiving device.

33. A method of in vivo fluorescence imaging, the method comprising:

a) implanting at least one fluorescence imager according to claim 1 and a plurality of light emitting sources in tissue of a subject, wherein the plurality of light emitting sources is located on the chip or externally;

b) contacting a cell of interest with at least one fluorophore conjugate, wherein the fluorophore conjugate comprises a fluorophore conjugated to a binding agent that selectively binds to a target marker on the cell of interest; and c) providing power to the fluorescence imager, wherein the plurality of light emitting sources located on the chip or externally provides excitation light at an excitation wavelength of the fluorophore, and the imaging array detects fluorescent light emitted from the fluorophore.

34. The method of claim 33, wherein the plurality of light emitting sources are micro-star external light sources.

35. The method of claim 33, wherein the plurality of light emitting sources comprises multiple light sources emitting light at different excitation wavelengths suitable for generating fluorescence from multiple fluorophore conjugates bound to different target markers on cells of interest.

36. The method of claim 33, wherein said providing power comprises providing power from an on-chip battery, a radionuclide, an on-chip photovoltaic system, an on-chip radionuclide in combination with a scintillator and photovoltaic energy harvester, an external ultrasound transducer, an external electromagnetic (EM) transducer, an external inductive transducer, or an external radiofrequency (RF) transducer.

* * * * *